US008158761B2

(12) United States Patent
Wands et al.

(10) Patent No.: US 8,158,761 B2
(45) Date of Patent: Apr. 17, 2012

(54) WNT PROTEINS AND DETECTION AND TREATMENT OF CANCER

(75) Inventors: Jack R. Wands, Providence, RI (US); Miran Kim, North Providence, RI (US)

(73) Assignee: Rhode Island Hospital, Providence, RI (US)

(*) Notice: Subject to any disclaimer, the term of this patent is extended or adjusted under 35 U.S.C. 154(b) by 632 days.

(21) Appl. No.: 11/909,308

(22) PCT Filed: Sep. 21, 2005

(86) PCT No.: PCT/US2005/033775
§ 371 (c)(1),
(2), (4) Date: Aug. 4, 2008

(87) PCT Pub. No.: WO2006/034328
PCT Pub. Date: Mar. 30, 2006

(65) Prior Publication Data
US 2009/0074777 A1    Mar. 19, 2009

Related U.S. Application Data

(60) Provisional application No. 60/612,098, filed on Sep. 21, 2004.

(30) Foreign Application Priority Data

Jan. 5, 2005   (WO) ................ PCT/US2005/000267

(51) Int. Cl.
*C07K 16/00* (2006.01)
(52) U.S. Cl. .................................................. 530/388.1
(58) Field of Classification Search ........................ None
See application file for complete search history.

(56) References Cited

U.S. PATENT DOCUMENTS

| 6,043,053 A | 3/2000 | Barnes et al. |
| 6,924,141 B2 | 8/2005 | Morgan et al. |
| 2003/0165500 A1 | 9/2003 | Rhee et al. |
| 2004/0247593 A1* | 12/2004 | He et al. ................... 424/143.1 |

FOREIGN PATENT DOCUMENTS

| WO | 03/092705 | 11/2003 |
| WO | 2004/032838 | 4/2004 |

OTHER PUBLICATIONS

Zips et al, 2005, In vivo, 19: 1-8.*
Mellman I, 2006, The Scientist, 20(1): 47-56.*
Bodey et al, 2000, Anticancer Res, 20: 2665-2676.*
Lee et al, 1999, J Immunol, 163: 6292-6300.*
Kim et al., "Functional interaction between Wnt3 and Frizzled-7 leads to activation of the Wnt/β-catenin signaling pathway in hepatocellular carcinoma cells," *Journal of Hepatology*, 48:780-791 (2008).
Aberle et al., "Cadherin-Catenin Complex: Protein Interactions and Their Implications for Cadherin Function," *Journal of Cellular Biochemistry*, vol. 61:514-523 (1996).
Anna et al., "Expression of Potential β-catenin targets, cyclin D1, c-Jun, c-Myc, E-cadherin, and EGFR in chemically induced hepatocellular neoplasms from B6C3F1 mice," *Toxicology and Applied Pharmacology*, vol. 190:135-145 (2003).
Anthony, "Hepatocellular carcinoma: an overview," *Histopathology*, vol. 39:109-118 (2001).
Aoki et al., "Oncogenic transformation by β-Catenin: deletion analysis and characterization of selected target genes," *Oncogene*, vol. 21:6983-6991 (2002).
Ban et al., "GSK-3β phosphorylation and alteration of β-catenin in hepatocellular carcinoma," *Cancer Letters*, vol. 199:201-208 (2003).
Bhanot et al., "A new member of the *frizzled* family from *Drosophila* functions as a Wingless receptor," *Nature*, vol. 382:225-230 (1996).
Bièche et al., "Quantitation of *MYC* Gene Expression in Sporadic Breast Tumors with a Real-Time Reverse Transcription-PCR Assay," *Cancer Research*, vol. 59:2759-2765 (1999).
Bradley et al., "The proto-oncogene *int*-1 encodes a secreted protein associated with the extracellular matrix," *The EMBO Journal*, vol. 9:1569-1575 (1990).
Cagatay et al., "p53 Mutation as a source of aberrant β-catenin accumulation in cancer cells," *Oncogene*, vol. 21:7971-7980 (2002).
Calvisi et al., "Activation of β-Catenin during Hepatocarcinogenesis in Transgenic Mouse Models: Relationship to Phenotype and Tumor Grade," *Cancer Research*, vol. 61:2085-2091 (2001).
Calvisi et al., "Disruption of β-Catenin Pathway or Genomic Instability Define Two Distinct Categories of Liver Cancer in Transgenic Mice," *Gastroenterology*, vol. 126:1374-1386 (2004).
Candidus et al., "No Evidence for Mutations in the α- and β-Catenin Genes in Human Gastric and Breast Carcinomas," *Cancer Research*, vol. 56:49-52 (1996).
Cariani et al., "Differential Expression in Insulin-like Growth Factor II mRNA in Human Primary Liver Cancers, Benign Liver Tumors, and Liver Cirrhosis," *Cancer Research*, vol. 48:6844-6849 (1988).
Carloni et al., "The Integrin α6β1, Is Necessary for the Matrix-Dependent Activation of FAK and MAP Kinase and the Migration of Human Hepatocarcinoma Cells," *Hepatology*, vol. 34:42-49 (2001).
Carruba et al., "Truncated Form of β-Catenin and Reduced Expression of Wild-Type Catenins Feature HepG2 Human Liver Cancer Cells," *Annals New York Academy of Sciences*, vol. 886:212-216 (1999).
Caselmann et al., "Hepatitis C virus infection as a major risk factor for hepatocellular carcinoma," *Journal of Hepatology*, vol. 24:61-66 (1996).
Cha et al., "Hepatitis B Virus X Protein Is Essential for the Activation of Wnt/β-Catenin Signaling in Hepatoma Cells," *Hepatology*, vol. 39:1683-1693 (2004).
Chan et al., "Evidence that Armadillo Transduces Wingless by Mediating Nuclear Export or Cytosolic Activation of Pangolin," *Cell*, vol. 111:265-280 (2002).
Cheon et al., "β-Catenin stabilization dysregulates mesenchymal cell proliferation, motility, and invasiveness and causes aggressive fibromatosis and hyperplastic cutaneous wounds," *PNAS*, vol. 99:6973-6978 (2002).
Chung, "The Genetic Basis of Colorectal Cancer: Insights into Critical Pathways of Tumorigenesis," *Gastroenterology*, vol. 119:854-865 (2000).
Clevers, "Axin and hepatocellular carcinomas," *Nature Genetics*, vol. 24:206-208 (2000).

(Continued)

*Primary Examiner* — Sean Aeder
(74) *Attorney, Agent, or Firm* — Fish & Richardson P.C.

(57) ABSTRACT

The present specification provides, inter alia, methods of using Wnt and FZD proteins, genes, FZD and Wnt-specific antibodies and probes in diagnosis and treatment of cancer and for screening test compounds for an ability to treat cancer. Also disclosed are compounds useful for treating cancer such as liver cancer.

12 Claims, 14 Drawing Sheets

OTHER PUBLICATIONS

Davila et al., "Hepatitis C Infection and the Increasing Incidence of Hepatocellular Carcinoma: A Population-Based Study," *Gastroenterology*, vol. 127:1372-1380 (2004).

de La Coste et al., "Somatic mutations of the β-Catenin gene are frequent in mouse and human hepatocellular carcinoma," *Proc. Natl. Acad. Sci. USA*, vol. 95:8847-8851 (1998).

de la Monte et al., "ATP Luminescence-Based Motility-Invasion Assay," *Biotechniques*, vol. 33:98-106 (2002).

De Souza et al., "*M6P/IGF2R* gene is mutated in human hepatocellular carcinomas with loss of heterozygosity," *Nature Genetics*, vol. 11:447-449 (1995).

Devereux et al., "Mutation of β-catenin is an early event in chemically induced mouse hepatocellular carcinogenesis," *Oncogene*, vol. 18: 4726-4733 (1999).

Devereux et al., "*CTNNB1* Mutations and β-Catenin Protein Accumulation in Human Hepatocellular Carcinomas Associated With High Exposure to Aflatoxin B1," *Molecular Carcinogenesis*, vol. 31:68-73 (2001).

Dhoot et al., "Regulation of Wnt Signaling and Embryo Patterning by an Extracellular Sulfatase," *Science*, vol. 293:1663-1666 (2001).

Du et al., "Identification of Distinct Classes and Functional Domains of Wnts through Expression of Wild-Type and Chimeric Proteins in *Xenopus* Embryos," *Molecular and Cell Biology*, vol. 15:2625-2634 (1995).

Dubois et al., "Time-course development of differentiated hepatocarcinoma and lung metastasis in transgenic mice," *Journal of Hepatology*, vol. 13:227-239 (1991).

El-Serag et al., "Rising Incidence of Hepatocellular Carcinoma in the United States," *The New England Journal of Medicine*, vol. 340:745-750 (1999).

Etiemble et al., "Liver-specific expression and high oncogenic efficiency of c-*myc* transgene activated by woodchuck hepatitis virus insertion," *Oncogene*, vol. 9:727-737 (1994).

Fausto et al., "Mouse Liver Tumorigenesis: Models, Mechanisms, and Relevance to Human Disease," *Seminars in Liver Disease*, vol. 19:243-252 (1999).

Feitelson et al., "Genetic mechanisms of hepatocarcinogenesis", *Oncogene*, vol. 21:2593-2604 (2002).

Frith et al., "Tumors of the liver," *Pathology of Tumors in Laboratory Animals.*, V. Turusov and U. Mohn, editors, IARC. Lyon, France, vol. 2:223-270 (1994).

Giles et al., "Caught up in a Wnt storm: Wnt signaling in cancer," *Biochimica et Biophysica Acta*, vol. 1653:1-24 (2003).

Gregorieff et al., "Expression Pattern of Wnt Signaling Components in the Adult Intestine," *Gastroenterology*, vol. 129:626-638 (2005).

Hanahan et al., "The Hallmarks of Cancer," *Cell*, vol. 100:57-70 (2000).

He et al., "Identification of c-*MYC* as a Target of the APC Pathway," *Science*, vol. 281:1509-1512 (1998).

Herrmann et al., "Oncogenic Role and Specificity of Frizzled Receptor Expression in Animal Models of Hepatocellular Carcinoma," *Hepatology*, vol. 38:180A (2003).

Holcombe et al., "Expression of Wnt ligands and Frizzled receptors in colonic mucosa and in colon carcinoma," *J. Clin. Pathol. Mol. Pathol.*, vol. 55:220-226 (2002).

Hommura et al., "Increased Expression of β-Catenin Predicts Better Prognosis in Nonsmall Cell Lung Carcinomas," *Cancer*, vol. 94:752-758 (2002).

Hsu et al., "β-Catenin Mutations Are Associated with a Subset of Low-Stage Hepatocellular Carcinoma Negative for Hepatitis B Virus and with Favorable Prognosis," *American Journal of Pathology*, vol. 157:763-770 (2000).

Hsu et al., "Mutational hotspot in the p53 gene in human hepatocellular carcinomas," *Nature*, vol. 350.:427-428 (1991).

Huang et al., "β-Catenin Mutations Are Frequent in Human Hepatocellular Carcinomas Associated with Hepatitis C virus Infection," *American Journal of Pathology*, vol. 155:1795-1801 (1999).

Idilman et al., "Pathogenesis of hepatitis B and C-induced hepatocellular carcinoma," *Journal of Viral Hepatitis*, vol. 5:285-299 (1998).

Iozzo et al., "Aberrant Expression of the Growth Factor *Wnt-5A* in Human Malignancy," *Cancer Research*, vol. 55:3495-3499 (1995).

Inagawa et al., "Expression and Prognostic Roles of β-Catenin in Hepatocellular Carcinoma: Correlation with Tumor Progression and Postoperative Survival," *Clinical Cancer Research*, vol. 8:450-456 (2002).

Jönsson et al., "Involvement of adenomatous polyposis coli (APC)/β-catenin signalling in human breast cancer," *European Journal of Cancer*, vol. 36:242-248 (2000).

Jones et al., "Secreted Frizzled-related proteins: searching for relationships and patterns," *BioEssays*, vol. 24:811-820 (2002).

Katoh, "Molecular cloning and characterization of human *WNT3*," *International Journal of Oncology*, vol. 19:977-982 (2001).

Kinzler et al., "Lessons from Hereditary Colorectal Cancer," *Cell*, vol. 87:159-170 (1996).

Kirikoshi et al., "Molecular cloning and characterization of human *WNT11*," *International Journal of Molecular Medicine*, vol. 8:651-656 (2001).

Kirikoshi et al., "Up-regulation of *Frizzled-7 (FZD7)* in human gastric cancer," *Int. J. Oncol.*, vol. 19:111-115 (2001).

Kolligs et al., "Neoplastic Transformation of RK3E by Mutant β-Catenin Requires Deregulation of Tcf/Lef Transcription but Not Activation of c-*myc* Expression," *Molecular and Cellular Biology*, vol. 19:5696-5706 (1999).

Korinek et al., "Constitutive Transcriptional Activation by a β-Catenin-Tcf Complex in APC$^{-/-}$Colon Carcinoma," *Science*, vol. 275:1784-1787 (1997).

Kühl et al., "The Wnt/Ca$^{2+}$ pathway: a new vertebrate Wnt signaling pathway takes shape," *Trends in Genet.*, vol. 16:279-283 (2000).

Laurent-Puig et al., "Genetic Alterations Associated With Hepatocellular Carcinomas Define Distinct Pathways of Hepatocarcinogenesis," *Gastroenterology*, vol. 120:1763-1773 (2001).

Legoix et al., "Beta-catenin mutations in hepatocellular carcinoma correlate with a low rate of loss of heterozygosity," *Oncogene*, vol. 18:4044-4046 (1999).

Lejeune et al., "*Wnt5a* Cloning, Expression, and Up-Regulation in Human Primary Breast Cancers," *Clinical Cancer Research*, vol. 1:215-222 (1995).

Liang et al., "Wnt5a Inhibits B cell proliferation and functions as a tumor suppressor in hematopoietic tissue," *Cancer Cell*, vol. 4:349-360 (2003).

Lin et al., "β-Catenin, a novel prognostic marker for breast cancer: Its role in cyclin D1 expression and cancer progression," *PNAS*, vol. 97:4262-4266 (2000).

Lin et al., "Dally cooperates with *Drosophila* Frizzled 2 to transduce Wingless signalling", *Nature*, vol. 400:281-284 (1999).

Lisovsky et al., "Frizzled Receptors Activate a Novel JNK-Dependent Pathway that May Lead to Apoptosis," *Current Biology*, vol. 12:53-58 (2002).

Liu et al., "Phosphorylation of β-Catenin and Epidermal Growth Factor Receptor by Intestinal Trefoil Factor," *Laboratory Investigation*, vol. 77:557-563 (1997).

Maloney et al., "Differential translocation of protein kinase C isozymes by phorbol esters, EGF, and ANG II in rat liver WB cells," *Am. J. Physiol.*, vol. 274:C974-C982 (1998).

Maye et al., "Multiple Mechanisms for Wnt1 1-mediated Repression of the Canonical Wnt Signaling Pathway," *The Journal of Biological Chemistry*, vol. 279:24659-24665 (2004).

Merle et al., "Oncogenic role of the frizzed-7/β-Catenin pathway in hepatocellular carcinoma," *Journal of Hepatology*, vol. 43:854-862 (2005).

Merle et al., "Functional Consequences of Frizzled-7 Receptor Overexpression in Human Hepatocellular Carcinoma," *Gastroenterology*, vol. 127:1110-1122 (2004).

Merle et al., "The Role of Frizzled 7 Expression in the Pathogenesis of Human Hepatocellular Carcinoma," *Journal of Hepatology*, vol. 38(4):589A (2003).

Merle et al., Long-term high-dose interferon-α therapy delays *Hepadnavirus*-related hepatocarcinogenesis in X/*myc* transgenic mice, *Oncogene*, vol. 22:2762-2771 (2003).

Merle et al., "Preliminary results of interferon-α therapy on woodchuck hepatitis virus-induced hepatocarcinogenesis: possible benefit in female transgenic mice," *The Journal of Hepatology*, vol. 34:562-569 (2001).

Mohr et al., "Ethanol Inhibits Hepatocyte Proliferation in Insulin Receptor Substrate 1 Transgenic Mice," *Gastroenterology*, vol. 115:1558-1565 (1998).

Monga et al., "Hepatocyte Growth Factor Induces Wnt-independent Nuclear Translocation of β-Catenin after Met- β-Catenin Dissociation in Hepatocytes," *Cancer Research*, vol. 62:2064-2071 (2002).

Moore et al., "p53 Mutations Are Not Selected for in Simian Virus 40 T-Antigen-Induced Tumors from Transgenic Mice," *Journal of Virology*, vol. 66:641-649 (1992).

Morin, "β-Catenin signaling and cancer," *BioEssays*, vol. 21:1021-1030 (1999).

Morin et al., "Activation of β-Catenin-Tcf Signaling in Colon Cancer by Mutations in β-Catenin or APC," *Science*, vol. 275:1787-1790 (1997).

Müller et al., "Phosphorylation and Free Pool of β-Catenin Are Regulated by Tyrosine Kinases and Tyrosine Phosphatases during Epithelial Cell Migration," *The Journal of Biological Chemistry*, vol. 274:10173-10183 (1999).

Murray et al., "Mortality by Cause for Eight Regions of the World: Global Burden of Disease Study," *Lancet* 349:1269-1276 (1997).

Nagai et al., "Comprehensive allelotyping of human hepatocellular carcinoma," *Oncogene*, vol. 14:2927-2933 (1997).

Nhieu et al., "Nuclear Accumulation of Mutated β-Catenin in Hepatocellular Caracinoma Is Associated with Increased Cell Proliferation," *American Journal of Pathology*, vol. 155:703-710 (1999).

Orford et al., "Exogenous Expression of β-Catenin Regulates Contact Inhibition, Anchorage-independent Growth, Anoikis, and Radiation-induced Cell Cycle Arrest," *The Journal of Cell Biology*, vol. 146:855-867 (1999).

Park et al., "Nuclear localization of β-Catenin is an important prognostic factor in hepatoblastoma," *Journal of Pathology*, vol. 193:483-490 (2001).

Polakis et al., "The Adenomatous Polyposis Coli (APC) Tumor Suppressor," *Biochim. Biophys. Acta.*, vol. 1332:F-127-147 (1997).

Reichsman et al., "Glycosaminoglycans Can Modulate Extracellular Localization of the *wingless* Protein and Promote Signal Transduction," *The Journal of Cell Biology*, vol. 135:819-827 (1996).

Renard et al., "Hepatocellular carcinoma in WHV/N-*myc*2 transgenic mice: oncogenic mutations of β-catenin and synergistic effect of p53 null alleles," *Oncogene*, vol. 19:2678-2686 (2000).

Rimm et al., "Frequent Nuclear/Cytoplasmic Localization of β-Catenin without Exon 3 Mutations in Malignant Melanoma," *American Journal of Pathology*, vol. 154:325-329 (1999).

Roelink et al., "Molecular Cloning and Chromosomal Localization to 17q21 of the Human WNT3 Gene," *Genomics*, vol. 17:790-792 (1993).

Roth et al., "Secreted Frizzled-related proteins inhibit motility and promote growth of human malignant glioma cells," *Oncogene*, vol. 37:4210-4220 (2000).

Satoh et al., "*AXIN1* mutations in hepatocellular carcinomas, and growth suppression in cancer cells by virus-mediated transfer of *AXIN1*," *Nature Genetics*, vol. 24:245-250 (2000).

Satyamoorthy et al., "Insulin-like Growth Factor-1 Induces Survival and Growth of Biologically Early Melanoma Cells through Both the Mitogen-activated Protein Kinase and β-Catenin Pathways," *Cancer Research*, vol. 61:7318-7324 (2001).

Shimizu et al., "Transformation by Wnt Family Proteins Correlates with Regulation of β-Catenin," *Cell Growth & Differentiation*, vol. 8:1349-1358 (1997).

Smolich et al., "*Wnt* Family Proteins Are Secreted and Associated with the Cell Surface," *Molecular Biology of the Cell*, vol. 4:1267-1275 (1993).

Tanaka et al., "A novel frizzled gene identified in human esophageal carcinoma mediates APC/β-catenin signals," *Proc. Natl. Acad. Sci. USA*, vol. 95:10164-10169 (1998).

Terradillos et al., "The hepatitis B virus X gene potentiates c-*myc*-induced liver oncogenesis in transgenic mice," *Oncogene*, vol. 14:395-404 (1997).

Torbenson et al., "Hepatic Adenomas: Analysis of Sex Steroid Receptor Status and the Wnt Signaling Pathway," *Mod. Pathol.*, vol. 15(3):189-196 (2002).

Ueda et al., "Mutations of the β- and γ-catenin genes are uncommon in human lung, breast, kidney, cervical and ovarian carcinomas," *British Journal of Cancer*, vol. 85:64-68 (2001).

Umeda et al., "β-Catenin Mutations Are Absent in Hepatocellular Carcinomas of SV40 T-antigen Transgenic Mice," *Int. J. Oncol.*, vol. 16:1133-1136 (2000).

Van Noort et al., "Wnt Signaling Controls the Phosphorylation Status of β-Catenin," *The Journal of Biological Chemistry*, vol. 277:17901-17905 (2002).

Veeman et al., "Zebrafish Prickle, a Modulator of Noncanonical Wnt/Fz Signaling, Regulates Gastrulation Movements," *Current Biology*, vol. 13:680-685 (2003).

Weeraratna et al., "Wnt5a signaling directly affects cell motility and invasion of metastatic melanoma," *Cancer Cell*, vol. 1:279-288 (2002).

Willert et al., "Wnt proteins are lipid-modified and can act as stem cell growth factors," *Nature*, vol. 423:448-452 (2003).

Wong et al., "β-Catenin Mutation and Overexpression in Hepatocellular Carcinoma: Clinicopathologic and Prognostic Significance," *Cancer*, vol. 92:136-145 (2001).

Yeh et al., "Elevation of Transforming Growth Factor α and Its Relationship to the Epidermal Growth Factor and α-Fetoprotein Levels in Patients with Hepatocellular Carcinoma," *Cancer Research*, vol. 47:896-901 (1987).

Zhang et al., "The Expression of C-MYC-and C-N-Ras in Human Cirrhotic Livers, Hepatocellular Carcinomas and Liver Tissue Surrounding the Tumors," *Oncogene*, vol. 5:909-914 (1990).

Zhang et al., "Deletions of Chromosome 13q, Mutations in *Retinoblastoma 1*, and Retinoblastoma Protein State in Human Hepatocellular Carinoma," *Cancer Research*, vol. 54:4177-4182 (1994).

Zhu et al., "Analysis of Wnt Gene Expression in Prostate Cancer: Mutual Inhibition by WNT11 and the Androgen Receptor," *Cancer Research*, vol. 64:7918-7926 (2004).

Zimonjic et al., "Novel Recurrent Genetic Imbalances in Human Hepatocellular Carcinoma Cell Lines Identified by Comparative Genomic Hybridization," *Hepatology*, vol. 29:1208-1214 (1999).

NCBI Protein database Accession No. BAA34668, Feb. 6, 1999.
NCBI Protein database Accession No. NP_003384, Aug. 23, 2004.
NCBI Protein database Accession No. NP_003498, Aug. 23, 2004.
NCBI Protein database Accession No. NP_004617, Aug. 23, 2004.
NCBI Protein database Accession No. NP_032083, Aug. 25, 2004.
NCBI Protein database Accession No. NP_033545, Aug. 25, 2004.
NCBI Protein database Accession No. NP_033547, Aug. 25, 2004.
NCBI Protein database Accession No. NP_035850, Aug. 25, 2004.
NCBI Protein database Accession No. NP_110380, Aug. 23, 2004.
NCBI Protein database Accession No. Q61091, Mar. 15, 2004.
NCBI Protein database Accession No. Q9H461, Sep. 15, 2003.

Branda et al., "Upregulation of Wnt and Frizzled genes as biomarkers for hepatocellular carcinoma," Hepatology, Williams and Wilkins, Baltimore, MD, US 44(4)Supp.1:514A (2006).

Lustig et al., "The Wnt pathway and its role in tumor development," Journal of Cancer Research and Clinical Oncology, Springer International, Berlin, 129:199-221 (2003).

Vincan, E., "Frizzled/Wnt signaling: the insidious promoter of tumour growth and progression," Frontiers in Bioscience, Frontiers in Bioscience, Albertson, NY, US 9:1023-1034 (2004).

Willert et al., "A transcriptional response to Wnt protein in human embryonic carcinoma cells," BMC Developmental Biology, Biomed Central Ltd., London, GB, 2(1):8 (2002).

Katoh, "*Regulation of W7VT3 and WNT3A* mRNAs in human cancer cell lines NT2, MCF-7, and MKN45", *International Journal of Oncology*, vol. 20:373-377 (2002).

International Search Report and the Written Opinion issued on May 21, 2008, for corresponding PCT application No. PCT/US05/33775; pp. 1-13.

International Search Report and Written Opinion issued on Jul. 14, 2008 for related International Application No. PCT/US05/00267; pp. 1-10.

Office Action, European Application No. 05 812 548.5-2403, dated Dec. 23, 2010, pp. 1-8.

Supplementary Partial Search Report, European Application No. 05 81 2548, dated Oct. 29, 2009; pp. 1-11.

Merle et al., "Functional Consequences of Frizzled-7 Receptor Overexpression in Human Hepatocellular Carcinoma," *Hepatology*, vol. 38, No. 4, Suppl. 1, p. 564A, Abstract 834, Oct. 2003.

Office Action, China Patent Application No. 200580039735.4, Sep. 27, 2010, (pp. 1-12).

Office Action, Japan Patent Application No. 2007-533596; May 30, 2011, (pp. 1-13).

Office Action, Taiwan Patent Application No. 94132486, Jun. 27, 2011, (pp. 1-16).

Office Action, European Patent Office; 05812548.5-2403; mailed Nov. 18, 2011; (3 pages).

\* cited by examiner

Human Frizzled 7

Accession: O75084
Protein name: Frizzled 7 [Precursor]
DEFINITION: frizzled 7; Frizzled, drosophila, homolog of, 7;
frizzled(Drosophila) homolog 7 [Homo sapiens].
ACCESSION   NP_003498

ORIGIN (574 aa)
MRDPGAAVPL SSLGFCALVL ALLGALSAGA GAQPYHGEKG ISVPDHGFCQ PISIPLCTDI
AYNQTILPNL LGHTNQEDAG LEVHQFYPLV KVQCSPELRF FLCSMYAPVC TVLDQAIPPC
RSLCERARQG CEALMNKFGF QWPERLRCEN FPVHGAGEIC VGQNTSDGSG GPGGGPTAYP
TAPYLPDLPF TALPPGASDG KGRPAFPFSC PRQLKVPPYL GYRFLGERDC GAPCEPGRAN
GLMYFKEEER RFARLWVGVW SVLCCASTLF TVLTYLVDMR RFSYPERPII FLSGCYFMVA
VAHVAGFFLE DRAVCVERFS DDGYRTVAQG TKKEGCTILF MVLYFFGMAS SIWWVILSLT
WFLAAGMKWG HEAIEANSQY FHLAAWAVPA VKTITILAMG QVDGDLLNGV CYVGFSSVDA
LRGFVLAPLF VYFFIGTSFL LAGFVSFFRI RTIMKHDGTK TEKLEKLMVR IGVFSVLYTV
PATIVLACYF YEQAFREHWE RTWLLQTCKS YAVPCPPGHF PPMSPDFTVF MIKCLMTMIV
GITTGFWIWS GKTLQSWRRF YHRLSHSSKG ETAV   (SEQ ID NO:1)

Human Frizzled 7 Putative ligand binding site

* Cystein-rich domain (CRD)
CQPISIPLCTDIAYNQTILPNLLGHTNQEDAGLEVHQFYPLVKVQCSPELRFFLCSMYAPVCRSLCERARQGC
EALMNKFGFQWPERLRCENFP (49-152)  (SEQ ID NO:2)

Mouse Frizzled 7

Accession: Q61090
Protein name: Frizzled 7 [Precursor]
DEFINITION: frizzled 7 [Mus musculus].
ACCESSION   NP_032083

ORIGIN (572 aa)
MRGPGTAASH SPLGLCALVL ALLGALPTDT RAQPYHGEKG ISVPDHGFCQ PISIPLCTDI
AYNQTILPNL LGHTNQEDAG LEVHQFYPLV KVQCSPELRF FLCSMYAPVC TVLDQAIPPC
RSLCERARQG CEALMNKFGF QWPERLRCEN FPVHGAGEIC VGQNTSDGSG GAGGSPTAYP
TAPYLPDPPF TAMSPSDGRG RLSFPFSCPR QLKVPPYLGY RFLGERDCGA PCEPGRANGL
MYFKEEERRF ARLWVGVWSV LSCASTLFTV LTYLVDMRRF SYPERPIIFL SGCYFMVAVA
HVAGFLLEDR AVCVERFSDD GYRTVAQGTK KEGCTILFMV LYFFGMASSI WWVILSLTWF
LAAGMKWGHE AIEANSQYFH LAAWAVPAVK TITILAMGQV DGDLLSGVCY VGLSSVDALR
GFVLAPLFVY LFIGTSFLLA GFVSLFRIRT IMKHDGTKTE KLEKLMVRIG VFSVLYTVPA
TIVLACYFYE QAFREHWERT WLLQTCKSYA VPCPPRHFSP MSPDFTVFMI KYLMTMIVGI
TTGFWIWSGK TLQSWRRFYH RLSHSSKGET AV(SEQ ID NO:3)

FIG. 8A

Human Frizzled 8

Accession: Q9H461
Protein name: Frizzled 8 [Precursor]

Origin (694 aa)
```
MEWGYLLEVT SLLAALALLQ RSSGAAAASA KELACQEITV PLCKGIGYNY TYMPNQFNHD
TQDEAGLEVH QFWPLVEIQC SPDLKFFLCS MYTPICLEDY KKPLPPCRSV CERAKAGCAP
LMRQYGFAWP DRMRCDRLPE QGNPDTLCMD YNRTDLTTAA PSPPRRLPPP PPGEQPPSGS
GHGRPPGARP PHRGGGRGGG GGDAAAPPAR GGGGGGKARP PGGGAAPCEP GCQCRAPMVS
VSSERHPLYN RVKTGQIANC ALPCHNPFFS QDERAFTVFW IGLWSVLCFV STFATVSTFL
IDMERFKYPE RPIIFLSACY LFVSVGYLVR LVAGHEKVAC SGGAPGAGGA GGAGGAAAGA
GAAGAGAGGP GGRGEYEELG AVEQHVRYET TGPALCTVVF LLVYFFGMAS SIWWVILSLT
WFLAAGMKWG NEAIAGYSQY FHLAAWLVPS VKSIAVLALS SVDGDPVAGI CYVGNQSLDN
LRGFVLAPLV IYLFIGTMFL LAGFVSLFRI RSVIKQQDGP TKTHKLEKLM IRLGLFTVLY
TVPAAVVVAC LFYEQHNRPR WEATHNCPCL RDLQPDQARR PDYAVFMLKY FMCLVVGITS
GVWVWSGKTL ESWRSLCTRC CWASKGAAVG GGAGATAAGG GGGPGGGGGG GPGGGGGPGG
GGGSLYSDVS TGLTWRSGTA SSVSYPKQMP LSQV(SEQ ID NO:4)
```

Human FZD8 Putative ligand binding site
\* Cystein-rich domain (CRD)
CQEI**TVPLCKGIGYNYTYMPNQFNHDTQDEAGLEVHQFWPLVEIQCSPDLKFFLCSMYTPICLED
YKKPLPPCRSVCERAKAGCAPLMRQYGFAWP**DRMRCDRLP (35-139) ((SEQ ID NO:5)

Mouse Frizzled 8

Accession: Q61091
Protein name: Frizzled 8 [Precursor]

Origin (685 aa)
```
MEWGYLLEVT SLLAALAVLQ RSSGAAAASA KELACQEITV PLCKGIGYNY TYMPNQFNHD
TQDEAGLEVH QFWPLVEIQC SPDLKFFLCS MYTPICLEDY KKPLPPCRSV CERAKAGCAP
LMRQYGFAWP DRMRCDRLPE QGNPDTLCMD YNRTDLTTAA PSPPRRLPPP PPGEQPPSG
SGHSRPPGAR PPHRGGSSRG SGDAAAAPPS RGGKARPPGG GAAPCEPGCQ CRAPMVSVSS
ERHPLYNRVK TGQIANCALP CHNPFFSQDE RAFTVFWIGL WSVLCFVSTF ATVSTFLIDM
ERFKYPERPI IFLSACYLFV SVGYLVRLVA GHEKVACSGG APGAGGRGGA GGAAAAGAGA
AGRGASSPGA RGEYEELGAV EQHVRYETTG PALCTVVFLL VYFFGMASSI WWVILSLTWF
LAAGMKWGNE AIAGYSQYFH LAAWLVPSVK SIAVLALSSV DGDPVAGICY VGNQSLDNLR
GFVLAPLVIY LFIGTMFLLA GFVSLFRIRS VIKQQGGPTK THKLEKLMIR LGLFTVLYTV
PAAVVVACLF YEQHNRPRWE ATHNCPCLRD LQPDQARRPD YAVFMLKYFM CLVVGITSGV
WVWSGKTLES WRALCTRCCW ASKGAAVGAG AGGSGPGGSG PGPGGGGHG GGGGSLYSDV
STGLTWRSGT ASSVSYPKQM PLSQV (SEQ ID NO:6)
```

FIG. 8B

Human Wnt3

Accession P56703
Protein name: Wnt-3 proto-oncogene protein [Precursor]
ACCESSION   NP_110380
Definition: wingless-type MMTV integration site family, member 3; WNT-3 proto-oncogene protein precursor [Homo sapiens]

ORIGIN (355 aa)
MEPHLLGLLL GLLLGGTRVL AGYPIWWSLA LGQQYTSLGS QPLLCGSIPG LVPKQLRFCR
NYIEIMPSVA EGVKLGIQEC QHQFRGRRWN CTTIDDSLAI FGPVLDKATR ESAFVHAIAS
AGVAFAVTRS CAEGTSTICG CDSHHKGPPG EGWKWGGCSE DADFGVLVSR EFADARENRP
DARSAMNKHN NEAGRTTILD HMHLKCKCHG LSGSCEVKTC WWAQPDFRAI GDFLKDKYDS
ASEMVVEKHR ESRGWVETLR AKYSLFKPPT ERDLVYYENS PNFCEPNPET GSFGTRDRTC
NVTSHGIDGC DLLCCGRGHN TRTEKRKEKC HCIFHWCCYV SCQECIRIYD VHTCK(SEQ ID NO:7)

Putative binding motifs

Human Wnt3

* Secreted growth factor protein (motif or domain)
1)   RESAFVHAIASAGVA (110-124) (SEQ ID NO:8)
2)   RSCAEGTSTICGCD (129-142) (SEQ ID NO:9)
3)   WKWGGCSEDADFG (153-165) (SEQ ID NO:10)
4)   CKCHGLSGSCEVKTCW (206-221) (SEQ ID NO:11)
5)   DLVYYENSPNFC (273-284) (SEQ ID NO:12)

Mouse Wnt3

Accession: P17553
Protein name: Wnt-3 proto-oncogene protein [Precursor]
DEFINITION: wingless-related MMTV integration site 3 [Mus musculus]
ACCESSION   NP_033547

ORIGIN (355 aa)
MEPHLLGLLL GLLLSGTRVL AGYPIWWSLA LGQQYTSLAS QPLLCGSIPG LVPKQLRFCR
NYIEIMPSVA EGVKLGIQEC QHQFRGRRWN CTTIDDSLAI FGPVLDKATR ESAFVHAIAS
AGVAFAVTRS CAEGTSTICG CDSHHKGPPG EGWKWGGCSE DADFGVLVSR EFADARENRP
DARSAMNKHN NEAGRTTILD HMHLKCKCHG LSGSCEVKTC WWAQPDFRAI GDFLKDKYDS
ASEMVVEKHR ESRGWVETLR AKYALFKPPT ERDLVYYENS PNFCEPNPET GSFGTRDRTC
NVTSHGIDGC DLLCCGRGHN TRTEKRKEKC HCVFHWCCYV SCQECIRIYD VHTCK(SEQ ID NO:13)

FIG. 8C

Human Wnt8B

Accession: Q93098
Protein name: Wnt-8b protein [Precursor]
DEFINITION: wingless-type MMTV integration site family, member 8B precursor [Homo sapiens].
ACCESSION: NP_003384

ORIGIN (351 aa)
```
MFLSKPSVYI CLFTCVLQLS HSWSVNNFLM TGPKAYLIYS SSVAAGAQSG IEECKYQFAW
DRWNCPERAL QLSSHGGLRS ANRETAFVHA ISSAGVMYTL TRNCSLGDFD NCGCDDSRNG
QLGGQGWLWG GCSDNVGFGE AISKQFVDAL ETGQDARAAM NLHNNEAGRK AVKGTMKRTC
KCHGVSGSCT TQTCWLQLPE FREVGAHLKE KYHAALKVDL LQGAGNSAAA RGAIADTFRS
ISTRELVHLE DSPDYCLENK TLGLLGTEGR ECLRRGRALG RWELRSCRRL CGDCGLAVEE
RRAETVSSCN CKFHWCCAVR CEQCRRRVTK YFCSRAERPR GGAAHKPGRK P (SEQ ID NO:14)
```

Putative binding motifs

Human Wnt8b

* Secreted growth factor protein (motif or domain)
1) RETAFVHAISSAGVM (83-97) (SEQ ID NO:15)
2) RNCSLGDFDNCGCD (102-115) (SEQ ID NO:16)
3) WLWGGCSDNVGFG (127-139) (SEQ ID NO:17)
4) CKCHGVSGSCTTQTCW (180-195) (SEQ ID NO:18)
5) ELVHLEDSPDYC (245-256) (SEQ ID NO:19)

Mouse Wnt8B

Accession: Q9WUD6
Protein name: Wnt-8b protein [Precursor]
DEFINITION: wingless related MMTV integration site 8b [Mus musculus].
ACCESSION NP_035850

ORIGIN (350 aa)
```
MFLMKPVCVL LVTCVLHRSH AWSVNNFLMT GPKAYLVYSS SVAAGAQSGI EECKYQFAWD
RWNCPERALQ LSSHGGLRSA NRETAFVHAI SSAGVMYTLT RNCSLGDFDN CGCDDSRNGQ
LGGQGWLWGG CSDNVGFGEA ISKQFVDALE TGQDARAAMN LHNNEAGRKA VKGTMKRTCK
CHGVSGSCTT QTCWLQLPEF REVGAHLKEK YHAALKVDLL QGAGNSAAGR GAIADTFRSI
STRELVHLED SPDYCLENKT LGLLGTEGRE CLRRGRALGR WERRSCRRLC GDCGLAVEER
RAETVSSCNC KFHWCCAVRC EQCRRRVTKY FCSRAERPPR GAAHKPGKNS(SEQ ID NO:20)
```

FIG. 8D

Human Wnt 11

Accession: O96014
Protein name: Wnt-11 protein [Precursor]
DEFINITION: wingless-type MMTV integration site family, member 11 precursor [Homo sapiens]
ACCESSION   NP_004617

ORIGIN (354 aa)
MRARPQVCEA LLFALALQTG VCYGIKWLAL SKTPSALALN QTQHCKQLEG LVSAQVQLCR
SNLELMHTVV HAAREVMKAC RRAFADMRWN CSSIELAPNY LLDLERGTRE SAFVYALSAA
AISHAIARAC TSGDLPGCSC GPVPGEPPGP GNRWGGCADN LSYGLLMGAK FSDAPMKVKK
TGSQANKLMR LHNSEVGRQA LRASLEMKCK CHGVSGSCSI RTCWKGLQEL QDVAADLKTR
YLSATKVVHR PMGTRKHLVP KDLDIRPVKD SELVYLQSSP DFCMKNEKVG SHGTQDRQCN
KTSNGSDSCD LMCCGRGYNP YTDRVVERCH CKYHWCCYVT CRRCERTVER YVCK (SEQ ID NO:21)

Putative binding motifs

Human Wnt11

* Secreted growth factor protein (motif or domain)
1)   RESAFVYALSAAAIS (109-123) (SEQ ID NO:22)
2)   RACTSGDLPGCSCG (128-141) (SEQ ID NO:23)
3)   NRWGGCADNLSYG (152-164) (SEQ ID NO:24)
4)   CKCHGVSGSCSIRTCW (209-224) (SEQ ID NO:25)
5)   ELVYLQSSPDFC (272-283) (SEQ ID NO:26)

Mouse Wnt 11

Accession: P48615
Protein name: Wnt-11 protein [Precursor]
DEFINITION: wingless-related MMTV integration site 11 [Mus musculus].
ACCESSION   NP_033545

ORIGIN (354 aa)
MRARPQVCEA LLFALALHTG VCYGIKWLAL SKTPAALALN QTQHCKQLEG LVSAQVQLCR
SNLELMRTIV HAARGAMKAC RRAFADMRWN CSSIELAPNY LLDLERGTRE SAFVYALSAA
TISHTIARAC TSGDLPGCSC GPVPGEPPGP GNRWGGCADN LSYGLLMGAK FSDAPMKVKK
TGSQANKLMR LHNSEVGRQA LRASLETKCK CHGVSGSCSI RTCWKGLQEL QDVAADLKTR
YLSATKVVHR PMGTRKHLVP KDLDIRPVKD SELVYLQSSP DFCMKNEKVG SHGTQDRQCN
KTSNGSDSCD LMCCGRGYNP YTDRVVERCH CKYHWCCYVT CRRCERTVER YVCK (SEQ ID NO:27)

FIG. 8E

SEQUENCE LISTING

<160> NUMBER OF SEQ ID NOS: 85

<210> SEQ ID NO 1
<211> LENGTH: 574
<212> TYPE: PRT
<213> ORGANISM: Homo sapiens

<400> SEQUENCE: 1

```
Met Arg Asp Pro Gly Ala Ala Val Pro Leu Ser Ser Leu Gly Phe Cys
 1               5                  10                  15

Ala Leu Val Leu Ala Leu Leu Gly Ala Leu Ser Ala Gly Ala Gly Ala
             20                  25                  30

Gln Pro Tyr His Gly Glu Lys Gly Ile Ser Val Pro Asp His Gly Phe
         35                  40                  45

Cys Gln Pro Ile Ser Ile Pro Leu Cys Thr Asp Ile Ala Tyr Asn Gln
     50                  55                  60

Thr Ile Leu Pro Asn Leu Leu Gly His Thr Asn Gln Glu Asp Ala Gly
 65                  70                  75                  80

Leu Glu Val His Gln Phe Tyr Pro Leu Val Lys Val Gln Cys Ser Pro
                 85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Lys Gly Arg Pro Ala Phe Pro Phe
        195                 200                 205
```

```
Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu Trp
            245                 250                 255

Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
        275                 280                 285

Ile Ile Phe Leu Ser Gly Cys Tyr Phe Met Val Ala Val Ala His Val
    290                 295                 300

Ala Gly Phe Phe Leu Glu Asp Arg Ala Val Cys Val Glu Arg Phe Ser
305                 310                 315                 320

Asp Asp Gly Tyr Arg Thr Val Ala Gln Gly Thr Lys Lys Glu Gly Cys
                325                 330                 335

Thr Ile Leu Phe Met Val Leu Tyr Phe Phe Gly Met Ala Ser Ser Ile
            340                 345                 350

Trp Trp Val Ile Leu Ser Leu Thr Trp Phe Leu Ala Ala Gly Met Lys
            355                 360                 365

Trp Gly His Glu Ala Ile Glu Ala Asn Ser Gln Tyr Phe His Leu Ala
    370                 375                 380

Ala Trp Ala Val Pro Ala Val Lys Thr Ile Thr Ile Leu Ala Met Gly
385                 390                 395                 400

Gln Val Asp Gly Asp Leu Leu Asn Gly Val Cys Tyr Val Gly Phe Ser
                405                 410                 415

Ser Val Asp Ala Leu Arg Gly Phe Val Leu Ala Pro Leu Phe Val Tyr
            420                 425                 430

Phe Phe Ile Gly Thr Ser Phe Leu Leu Ala Gly Phe Val Ser Phe Phe
        435                 440                 445

Arg Ile Arg Thr Ile Met Lys His Asp Gly Thr Lys Thr Glu Lys Leu
    450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                485                 490                 495

Glu His Trp Glu Arg Thr Trp Leu Leu Gln Thr Cys Lys Ser Tyr Ala
            500                 505                 510

Val Pro Cys Pro Pro Gly His Phe Pro Pro Met Ser Pro Asp Phe Thr
        515                 520                 525

Val Phe Met Ile Lys Cys Leu Met Thr Met Ile Val Gly Ile Thr Thr
530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
                565                 570

<210> SEQ ID NO 2
<211> LENGTH: 94
<212> TYPE: PRT
<213> ORGANISM: Homo sapiens

<400> SEQUENCE: 2

Cys Gln Pro Ile Ser Ile Pro Leu Cys Thr Asp Ile Ala Tyr Asn Gln
1               5                   10                  15
```

```
Thr Ile Leu Pro Asn Leu Leu Gly His Thr Asn Gln Glu Asp Ala Gly
             20                  25                  30

Leu Glu Val His Gln Phe Tyr Pro Leu Val Lys Val Gln Cys Ser Pro
         35                  40                  45

Glu Leu Arg Phe Phe Leu Cys Ser Met Tyr Ala Pro Val Cys Arg Ser
 50                  55                  60

Leu Cys Glu Arg Ala Arg Gln Gly Cys Glu Ala Leu Met Asn Lys Phe
 65                  70                  75                  80

Gly Phe Gln Trp Pro Glu Arg Leu Arg Cys Glu Asn Phe Pro
                 85                  90

<210> SEQ ID NO 3
<211> LENGTH: 572
<212> TYPE: PRT
<213> ORGANISM: Mus musculus

<400> SEQUENCE: 3

Met Arg Gly Pro Gly Thr Ala Ala Ser His Ser Pro Leu Gly Leu Cys
 1               5                  10                  15

Ala Leu Val Leu Ala Leu Leu Gly Ala Leu Pro Thr Asp Thr Arg Ala
             20                  25                  30

Gln Pro Tyr His Gly Glu Lys Gly Ile Ser Val Pro Asp His Gly Phe
         35                  40                  45

Cys Gln Pro Ile Ser Ile Pro Leu Cys Thr Asp Ile Ala Tyr Asn Gln
 50                  55                  60

Thr Ile Leu Pro Asn Leu Leu Gly His Thr Asn Gln Glu Asp Ala Gly
 65                  70                  75                  80

Leu Glu Val His Gln Phe Tyr Pro Leu Val Lys Val Gln Cys Ser Pro
             85                  90                  95

Glu Leu Arg Phe Phe Leu Cys Ser Met Tyr Ala Pro Val Cys Thr Val
             100                 105                 110

Leu Asp Gln Ala Ile Pro Pro Cys Arg Ser Leu Cys Glu Arg Ala Arg
         115                 120                 125

Gln Gly Cys Glu Ala Leu Met Asn Lys Phe Gly Phe Gln Trp Pro Glu
 130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Ala Gly Gly Ser Pro
                 165                 170                 175

Thr Ala Tyr Pro Thr Ala Pro Tyr Leu Pro Asp Pro Phe Thr Ala
             180                 185                 190

Met Ser Pro Ser Asp Gly Arg Gly Arg Leu Ser Phe Pro Phe Ser Cys
             195                 200                 205

Pro Arg Gln Leu Lys Val Pro Pro Tyr Leu Gly Tyr Arg Phe Leu Gly
 210                 215                 220

Glu Arg Asp Cys Gly Ala Pro Cys Glu Pro Gly Arg Ala Asn Gly Leu
225                 230                 235                 240

Met Tyr Phe Lys Glu Glu Glu Arg Arg Phe Ala Arg Leu Trp Val Gly
                 245                 250                 255

Val Trp Ser Val Leu Ser Cys Ala Ser Thr Leu Phe Thr Val Leu Thr
             260                 265                 270

Tyr Leu Val Asp Met Arg Arg Phe Ser Tyr Pro Glu Arg Pro Ile Ile
         275                 280                 285

Phe Leu Ser Gly Cys Tyr Phe Met Val Ala Val Ala His Val Ala Gly
 290                 295                 300
```

Phe Leu Leu Glu Asp Arg Ala Val Cys Val Glu Arg Phe Ser Asp Asp
305                 310                 315                 320

Gly Tyr Arg Thr Val Ala Gln Gly Thr Lys Glu Gly Cys Thr Ile
                325                 330                 335

Leu Phe Met Val Leu Tyr Phe Phe Gly Met Ala Ser Ile Trp Trp
            340                 345                 350

Val Ile Leu Ser Leu Thr Trp Phe Leu Ala Ala Gly Met Lys Trp Gly
355                 360                 365

His Glu Ala Ile Glu Ala Asn Ser Gln Tyr Phe His Leu Ala Ala Trp
        370                 375                 380

Ala Val Pro Ala Val Lys Thr Ile Thr Ile Leu Ala Met Gly Gln Val
385                 390                 395                 400

Asp Gly Asp Leu Leu Ser Gly Val Cys Tyr Val Gly Leu Ser Ser Val
                405                 410                 415

Asp Ala Leu Arg Gly Phe Val Leu Ala Pro Leu Phe Val Tyr Leu Phe
            420                 425                 430

Ile Gly Thr Ser Phe Leu Leu Ala Gly Phe Val Ser Leu Phe Arg Ile
        435                 440                 445

Arg Thr Ile Met Lys His Asp Gly Thr Lys Thr Glu Lys Leu Glu Lys
450                 455                 460

Leu Met Val Arg Ile Gly Val Phe Ser Val Leu Tyr Thr Val Pro Ala
465                 470                 475                 480

Thr Ile Val Leu Ala Cys Tyr Phe Tyr Glu Gln Ala Phe Arg Glu His
                485                 490                 495

Trp Glu Arg Thr Trp Leu Leu Gln Thr Cys Lys Ser Tyr Ala Val Pro
            500                 505                 510

Cys Pro Pro Arg His Phe Ser Pro Met Ser Pro Asp Phe Thr Val Phe
        515                 520                 525

Met Ile Lys Tyr Leu Met Thr Met Ile Val Gly Ile Thr Thr Gly Phe
530                 535                 540

Trp Ile Trp Ser Gly Lys Thr Leu Gln Ser Trp Arg Arg Phe Tyr His
545                 550                 555                 560

Arg Leu Ser His Ser Ser Lys Gly Glu Thr Ala Val
                565                 570

<210> SEQ ID NO 4
<211> LENGTH: 694
<212> TYPE: PRT
<213> ORGANISM: Homo sapiens

<400> SEQUENCE: 4

Met Glu Trp Gly Tyr Leu Leu Glu Val Thr Ser Leu Leu Ala Ala Leu
1               5                   10                  15

Ala Leu Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60

Ala Gly Leu Glu Val His Gln Phe Trp Pro Leu Val Glu Ile Gln Cys
65                  70                  75                  80

Ser Pro Asp Leu Lys Phe Phe Leu Cys Ser Met Tyr Thr Pro Ile Cys
                85                  90                  95

Leu Glu Asp Tyr Lys Lys Pro Leu Pro Pro Cys Arg Ser Val Cys Glu
            100                 105                 110

```
Arg Ala Lys Ala Gly Cys Ala Pro Leu Met Arg Gln Tyr Gly Phe Ala
            115                 120                 125

Trp Pro Asp Arg Met Arg Cys Asp Arg Leu Pro Glu Gln Gly Asn Pro
130                 135                 140

Asp Thr Leu Cys Met Asp Tyr Asn Arg Thr Asp Leu Thr Thr Ala Ala
145                 150                 155                 160

Pro Ser Pro Pro Arg Arg Leu Pro Pro Pro Pro Gly Glu Gln Pro
                165                 170                 175

Pro Ser Gly Ser Gly His Gly Arg Pro Pro Gly Ala Arg Pro Pro His
            180                 185                 190

Arg Gly Gly Gly Arg Gly Gly Gly Gly Asp Ala Ala Ala Pro Pro
            195                 200                 205

Ala Arg Gly Gly Gly Gly Gly Lys Ala Arg Pro Pro Gly Gly Gly
210                 215                 220

Ala Ala Pro Cys Glu Pro Gly Cys Gln Cys Arg Ala Pro Met Val Ser
225                 230                 235                 240

Val Ser Ser Glu Arg His Pro Leu Tyr Asn Arg Val Lys Thr Gly Gln
                245                 250                 255

Ile Ala Asn Cys Ala Leu Pro Cys His Asn Pro Phe Phe Ser Gln Asp
            260                 265                 270

Glu Arg Ala Phe Thr Val Phe Trp Ile Gly Leu Trp Ser Val Leu Cys
            275                 280                 285

Phe Val Ser Thr Phe Ala Thr Val Ser Thr Phe Leu Ile Asp Met Glu
290                 295                 300

Arg Phe Lys Tyr Pro Glu Arg Pro Ile Ile Phe Leu Ser Ala Cys Tyr
305                 310                 315                 320

Leu Phe Val Ser Val Gly Tyr Leu Val Arg Leu Val Ala Gly His Glu
                325                 330                 335

Lys Val Ala Cys Ser Gly Gly Ala Pro Gly Ala Gly Ala Gly Gly
            340                 345                 350

Ala Gly Gly Ala Ala Ala Gly Ala Gly Ala Gly Ala Gly Ala Gly
            355                 360                 365

Gly Pro Gly Gly Arg Gly Glu Tyr Glu Glu Leu Gly Ala Val Glu Gln
370                 375                 380

His Val Arg Tyr Glu Thr Thr Gly Pro Ala Leu Cys Thr Val Phe
385                 390                 395                 400

Leu Leu Val Tyr Phe Phe Gly Met Ala Ser Ser Ile Trp Trp Val Ile
                405                 410                 415

Leu Ser Leu Thr Trp Phe Leu Ala Ala Gly Met Lys Trp Gly Asn Glu
            420                 425                 430

Ala Ile Ala Gly Tyr Ser Gln Tyr Phe His Leu Ala Ala Trp Leu Val
            435                 440                 445

Pro Ser Val Lys Ser Ile Ala Val Leu Ala Leu Ser Ser Val Asp Gly
450                 455                 460

Asp Pro Val Ala Gly Ile Cys Tyr Val Gly Asn Gln Ser Leu Asp Asn
465                 470                 475                 480

Leu Arg Gly Phe Val Leu Ala Pro Leu Val Ile Tyr Leu Phe Ile Gly
                485                 490                 495

Thr Met Phe Leu Leu Ala Gly Phe Val Ser Leu Phe Arg Ile Arg Ser
            500                 505                 510

Val Ile Lys Gln Gln Asp Gly Pro Thr Lys Thr His Lys Leu Glu Lys
            515                 520                 525

Leu Met Ile Arg Leu Gly Leu Phe Thr Val Leu Tyr Thr Val Pro Ala
530                 535                 540
```

```
Ala Val Val Ala Cys Leu Phe Tyr Glu Gln His Asn Arg Pro Arg
545                 550                 555                 560

Trp Glu Ala Thr His Asn Cys Pro Cys Leu Arg Asp Leu Gln Pro Asp
            565                 570                 575

Gln Ala Arg Arg Pro Asp Tyr Ala Val Phe Met Leu Lys Tyr Phe Met
        580                 585                 590

Cys Leu Val Val Gly Ile Thr Ser Gly Val Trp Val Ser Gly Lys
        595                 600                 605

Thr Leu Glu Ser Trp Arg Ser Leu Cys Thr Arg Cys Cys Trp Ala Ser
    610                 615                 620

Lys Gly Ala Ala Val Gly Gly Ala Gly Ala Thr Ala Ala Gly Gly
625                 630                 635                 640

Gly Gly Gly Pro Gly Gly Gly Gly Gly Pro Gly Gly Gly Gly
                645                 650                 655

Gly Pro Gly Gly Gly Gly Ser Leu Tyr Ser Asp Val Ser Thr Gly
            660                 665                 670

Leu Thr Trp Arg Ser Gly Thr Ala Ser Ser Val Ser Tyr Pro Lys Gln
        675                 680                 685

Met Pro Leu Ser Gln Val
        690

<210> SEQ ID NO 5
<211> LENGTH: 105
<212> TYPE: PRT
<213> ORGANISM: Homo sapiens

<400> SEQUENCE: 5

Cys Gln Glu Ile Thr Val Pro Leu Cys Lys Gly Ile Gly Tyr Asn Tyr
1               5                   10                  15

Thr Tyr Met Pro Asn Gln Phe Asn His Asp Thr Gln Asp Glu Ala Gly
            20                  25                  30

Leu Glu Val His Gln Phe Trp Pro Leu Val Glu Ile Gln Cys Ser Pro
        35                  40                  45

Asp Leu Lys Phe Phe Leu Cys Ser Met Tyr Thr Pro Ile Cys Leu Glu
    50                  55                  60

Asp Tyr Lys Lys Pro Leu Pro Pro Cys Arg Ser Val Cys Glu Arg Ala
65                  70                  75                  80

Lys Ala Gly Cys Ala Pro Leu Met Arg Gln Tyr Gly Phe Ala Trp Pro
                85                  90                  95

Asp Arg Met Arg Cys Asp Arg Leu Pro
            100                 105

<210> SEQ ID NO 6
<211> LENGTH: 685
<212> TYPE: PRT
<213> ORGANISM: Mus musculus

<400> SEQUENCE: 6

Met Glu Trp Gly Tyr Leu Leu Glu Val Thr Ser Leu Leu Ala Ala Leu
1               5                   10                  15

Ala Val Leu Gln Arg Ser Ser Gly Ala Ala Ala Ser Ala Lys Glu
            20                  25                  30

Leu Ala Cys Gln Glu Ile Thr Val Pro Leu Cys Lys Gly Ile Gly Tyr
        35                  40                  45

Asn Tyr Thr Tyr Met Pro Asn Gln Phe Asn His Asp Thr Gln Asp Glu
    50                  55                  60
```

```
Ala Gly Leu Glu Val His Gln Phe Trp Pro Leu Val Glu Ile Gln Cys
 65                  70                  75                  80

Ser Pro Asp Leu Lys Phe Phe Leu Cys Ser Met Tyr Thr Pro Ile Cys
                 85                  90                  95

Leu Glu Asp Tyr Lys Lys Pro Leu Pro Pro Cys Arg Ser Val Cys Glu
            100                 105                 110

Arg Ala Lys Ala Gly Cys Ala Pro Leu Met Arg Gln Tyr Gly Phe Ala
        115                 120                 125

Trp Pro Asp Arg Met Arg Cys Asp Arg Leu Pro Glu Gln Gly Asn Pro
    130                 135                 140

Asp Thr Leu Cys Met Asp Tyr Asn Arg Thr Asp Leu Thr Ala Ala
145                 150                 155                 160

Pro Ser Pro Pro Arg Arg Leu Pro Pro Pro Pro Pro Gly Glu Gln
                165                 170                 175

Pro Pro Ser Gly Ser Gly His Ser Arg Pro Pro Gly Ala Arg Pro Pro
                180                 185                 190

His Arg Gly Gly Ser Ser Arg Gly Ser Gly Asp Ala Ala Ala Ala Pro
            195                 200                 205

Pro Ser Arg Gly Gly Lys Ala Arg Pro Gly Gly Ala Ala Pro
        210                 215                 220

Cys Glu Pro Gly Cys Gln Cys Arg Ala Pro Met Val Ser Val Ser Ser
225                 230                 235                 240

Glu Arg His Pro Leu Tyr Asn Arg Val Lys Thr Gly Gln Ile Ala Asn
                245                 250                 255

Cys Ala Leu Pro Cys His Asn Pro Phe Phe Ser Gln Asp Glu Arg Ala
            260                 265                 270

Phe Thr Val Phe Trp Ile Gly Leu Trp Ser Val Leu Cys Phe Val Ser
        275                 280                 285

Thr Phe Ala Thr Val Ser Thr Phe Leu Ile Asp Met Glu Arg Phe Lys
    290                 295                 300

Tyr Pro Glu Arg Pro Ile Ile Phe Leu Ser Ala Cys Tyr Leu Phe Val
305                 310                 315                 320

Ser Val Gly Tyr Leu Val Arg Leu Val Ala Gly His Glu Lys Val Ala
                325                 330                 335

Cys Ser Gly Gly Ala Pro Gly Ala Gly Gly Arg Gly Ala Gly Gly
            340                 345                 350

Ala Ala Ala Ala Gly Ala Gly Ala Ala Gly Arg Gly Ala Ser Ser Pro
        355                 360                 365

Gly Ala Arg Gly Glu Tyr Glu Glu Leu Gly Ala Val Glu Gln His Val
    370                 375                 380

Arg Tyr Glu Thr Thr Gly Pro Ala Leu Cys Thr Val Val Phe Leu Leu
385                 390                 395                 400

Val Tyr Phe Phe Gly Met Ala Ser Ser Ile Trp Trp Val Ile Leu Ser
                405                 410                 415

Leu Thr Trp Phe Leu Ala Ala Gly Met Lys Trp Gly Asn Glu Ala Ile
            420                 425                 430

Ala Gly Tyr Ser Gln Tyr Phe His Leu Ala Ala Trp Leu Val Pro Ser
        435                 440                 445

Val Lys Ser Ile Ala Val Leu Ala Leu Ser Ser Val Asp Gly Asp Pro
    450                 455                 460

Val Ala Gly Ile Cys Tyr Val Gly Asn Gln Ser Leu Asp Asn Leu Arg
465                 470                 475                 480

Gly Phe Val Leu Ala Pro Leu Val Ile Tyr Leu Phe Ile Gly Thr Met
                485                 490                 495
```

```
Phe Leu Leu Ala Gly Phe Val Ser Leu Phe Arg Ile Arg Ser Val Ile
                500                 505                 510
Lys Gln Gln Gly Gly Pro Thr Lys Thr His Lys Leu Glu Lys Leu Met
            515                 520                 525
Ile Arg Leu Gly Leu Phe Thr Val Leu Tyr Thr Val Pro Ala Ala Val
        530                 535                 540
Val Val Ala Cys Leu Phe Tyr Glu Gln His Asn Arg Pro Arg Trp Glu
545                 550                 555                 560
Ala Thr His Asn Cys Pro Cys Leu Arg Asp Leu Gln Pro Asp Gln Ala
                565                 570                 575
Arg Arg Pro Asp Tyr Ala Val Phe Met Leu Lys Tyr Phe Met Cys Leu
            580                 585                 590
Val Val Gly Ile Thr Ser Gly Val Trp Val Trp Ser Gly Lys Thr Leu
        595                 600                 605
Glu Ser Trp Arg Ala Leu Cys Thr Arg Cys Cys Trp Ala Ser Lys Gly
610                 615                 620
Ala Ala Val Gly Ala Gly Gly Ser Gly Pro Gly Gly Ser Gly
625                 630                 635                 640
Pro Gly Pro Gly Gly Gly Gly His Gly Gly Gly Gly Ser Leu
                645                 650                 655
Tyr Ser Asp Val Ser Thr Gly Leu Thr Trp Arg Ser Gly Thr Ala Ser
            660                 665                 670
Ser Val Ser Tyr Pro Lys Gln Met Pro Leu Ser Gln Val
        675                 680                 685

<210> SEQ ID NO 7
<211> LENGTH: 355
<212> TYPE: PRT
<213> ORGANISM: Homo sapiens

<400> SEQUENCE: 7

Met Glu Pro His Leu Leu Gly Leu Leu Leu Gly Leu Leu Leu Gly Gly
1               5                   10                  15
Thr Arg Val Leu Ala Gly Tyr Pro Ile Trp Trp Ser Leu Ala Leu Gly
            20                  25                  30
Gln Gln Tyr Thr Ser Leu Gly Ser Gln Pro Leu Leu Cys Gly Ser Ile
        35                  40                  45
Pro Gly Leu Val Pro Lys Gln Leu Arg Phe Cys Arg Asn Tyr Ile Glu
    50                  55                  60
Ile Met Pro Ser Val Ala Glu Gly Val Lys Leu Gly Ile Gln Glu Cys
65                  70                  75                  80
Gln His Gln Phe Arg Gly Arg Arg Trp Asn Cys Thr Thr Ile Asp Asp
                85                  90                  95
Ser Leu Ala Ile Phe Gly Pro Val Leu Asp Lys Ala Thr Arg Glu Ser
            100                 105                 110
Ala Phe Val His Ala Ile Ala Ser Ala Gly Val Ala Phe Ala Val Thr
        115                 120                 125
Arg Ser Cys Ala Glu Gly Thr Ser Thr Ile Cys Gly Cys Asp Ser His
    130                 135                 140
His Lys Gly Pro Pro Gly Glu Gly Trp Lys Trp Gly Gly Cys Ser Glu
145                 150                 155                 160
Asp Ala Asp Phe Gly Val Leu Val Ser Arg Glu Phe Ala Asp Ala Arg
                165                 170                 175
Glu Asn Arg Pro Asp Ala Arg Ser Ala Met Asn Lys His Asn Asn Glu
            180                 185                 190
```

```
Ala Gly Arg Thr Thr Ile Leu Asp His Met His Leu Lys Cys Lys Cys
            195                 200                 205

His Gly Leu Ser Gly Ser Cys Glu Val Lys Thr Cys Trp Trp Ala Gln
        210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ser Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285

Glu Thr Gly Ser Phe Gly Thr Arg Asp Arg Thr Cys Asn Val Thr Ser
            290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Ile Phe His Trp
                325                 330                 335

Cys Cys Tyr Val Ser Cys Gln Glu Cys Ile Arg Ile Tyr Asp Val His
            340                 345                 350

Thr Cys Lys
        355

<210> SEQ ID NO 8
<211> LENGTH: 15
<212> TYPE: PRT
<213> ORGANISM: Homo sapiens

<400> SEQUENCE: 8

Arg Glu Ser Ala Phe Val His Ala Ile Ala Ser Ala Gly Val Ala
1               5                  10                  15

<210> SEQ ID NO 9
<211> LENGTH: 14
<212> TYPE: PRT
<213> ORGANISM: Homo sapiens

<400> SEQUENCE: 9

Arg Ser Cys Ala Glu Gly Thr Ser Thr Ile Cys Gly Cys Asp
1               5                   10

<210> SEQ ID NO 10
<211> LENGTH: 13
<212> TYPE: PRT
<213> ORGANISM: Homo sapiens

<400> SEQUENCE: 10

Trp Lys Trp Gly Gly Cys Ser Glu Asp Ala Asp Phe Gly
1               5                   10

<210> SEQ ID NO 11
<211> LENGTH: 16
<212> TYPE: PRT
<213> ORGANISM: Homo sapiens

<400> SEQUENCE: 11

Cys Lys Cys His Gly Leu Ser Gly Ser Cys Glu Val Lys Thr Cys Trp
1               5                   10                  15

<210> SEQ ID NO 12
```

```
<211> LENGTH: 12
<212> TYPE: PRT
<213> ORGANISM: Homo sapiens

<400> SEQUENCE: 12

Asp Leu Val Tyr Tyr Glu Asn Ser Pro Asn Phe Cys
 1               5                  10

<210> SEQ ID NO 13
<211> LENGTH: 355
<212> TYPE: PRT
<213> ORGANISM: Mus musculus

<400> SEQUENCE: 13

Met Glu Pro His Leu Leu Gly Leu Leu Leu Gly Leu Leu Ser Gly
 1               5                  10                  15

Thr Arg Val Leu Ala Gly Tyr Pro Ile Trp Trp Ser Leu Ala Leu Gly
                 20                  25                  30

Gln Gln Tyr Thr Ser Leu Ala Ser Gln Pro Leu Leu Cys Gly Ser Ile
             35                  40                  45

Pro Gly Leu Val Pro Lys Gln Leu Arg Phe Cys Arg Asn Tyr Ile Glu
 50                  55                  60

Ile Met Pro Ser Val Ala Glu Gly Val Lys Leu Gly Ile Gln Glu Cys
 65                  70                  75                  80

Gln His Gln Phe Arg Gly Arg Arg Trp Asn Cys Thr Thr Ile Asp Asp
                 85                  90                  95

Ser Leu Ala Ile Phe Gly Pro Val Leu Asp Lys Ala Thr Arg Glu Ser
            100                 105                 110

Ala Phe Val His Ala Ile Ala Ser Ala Gly Val Ala Phe Ala Val Thr
            115                 120                 125

Arg Ser Cys Ala Glu Gly Thr Ser Thr Ile Cys Gly Cys Asp Ser His
130                 135                 140

His Lys Gly Pro Pro Gly Glu Gly Trp Lys Trp Gly Gly Cys Ser Glu
145                 150                 155                 160

Asp Ala Asp Phe Gly Val Leu Val Ser Arg Glu Phe Ala Asp Ala Arg
                165                 170                 175

Glu Asn Arg Pro Asp Ala Arg Ser Ala Met Asn Lys His Asn Asn Glu
            180                 185                 190

Ala Gly Arg Thr Thr Ile Leu Asp His Met His Leu Lys Cys Lys Cys
            195                 200                 205

His Gly Leu Ser Gly Ser Cys Glu Val Lys Thr Cys Trp Trp Ala Gln
        210                 215                 220

Pro Asp Phe Arg Ala Ile Gly Asp Phe Leu Lys Asp Lys Tyr Asp Ser
225                 230                 235                 240

Ala Ser Glu Met Val Val Glu Lys His Arg Glu Ser Arg Gly Trp Val
                245                 250                 255

Glu Thr Leu Arg Ala Lys Tyr Ala Leu Phe Lys Pro Pro Thr Glu Arg
            260                 265                 270

Asp Leu Val Tyr Tyr Glu Asn Ser Pro Asn Phe Cys Glu Pro Asn Pro
        275                 280                 285

Glu Thr Gly Ser Phe Gly Thr Arg Asp Arg Thr Cys Asn Val Thr Ser
    290                 295                 300

His Gly Ile Asp Gly Cys Asp Leu Leu Cys Cys Gly Arg Gly His Asn
305                 310                 315                 320

Thr Arg Thr Glu Lys Arg Lys Glu Lys Cys His Cys Val Phe His Trp
                325                 330                 335
```

```
Cys Cys Tyr Val Ser Cys Gln Glu Cys Ile Arg Ile Tyr Asp Val His
                340                 345                 350
Thr Cys Lys
        355

<210> SEQ ID NO 14
<211> LENGTH: 351
<212> TYPE: PRT
<213> ORGANISM: Homo sapiens

<400> SEQUENCE: 14

Met Phe Leu Ser Lys Pro Ser Val Tyr Ile Cys Leu Phe Thr Cys Val
  1               5                  10                  15

Leu Gln Leu Ser His Ser Trp Ser Val Asn Asn Phe Leu Met Thr Gly
                20                  25                  30

Pro Lys Ala Tyr Leu Ile Tyr Ser Ser Val Ala Ala Gly Ala Gln
            35                  40                  45

Ser Gly Ile Glu Glu Cys Lys Tyr Gln Phe Ala Trp Asp Arg Trp Asn
 50                  55                  60

Cys Pro Glu Arg Ala Leu Gln Leu Ser Ser His Gly Gly Leu Arg Ser
 65                  70                  75                  80

Ala Asn Arg Glu Thr Ala Phe Val His Ala Ile Ser Ser Ala Gly Val
                85                  90                  95

Met Tyr Thr Leu Thr Arg Asn Cys Ser Leu Gly Asp Phe Asp Asn Cys
                100                 105                 110

Gly Cys Asp Asp Ser Arg Asn Gly Gln Leu Gly Gly Gln Gly Trp Leu
            115                 120                 125

Trp Gly Gly Cys Ser Asp Asn Val Gly Phe Gly Glu Ala Ile Ser Lys
130                 135                 140

Gln Phe Val Asp Ala Leu Glu Thr Gly Gln Asp Ala Arg Ala Ala Met
145                 150                 155                 160

Asn Leu His Asn Asn Glu Ala Gly Arg Lys Ala Val Lys Gly Thr Met
                165                 170                 175

Lys Arg Thr Cys Lys Cys His Gly Val Ser Gly Ser Cys Thr Thr Gln
            180                 185                 190

Thr Cys Trp Leu Gln Leu Pro Glu Phe Arg Glu Val Gly Ala His Leu
        195                 200                 205

Lys Glu Lys Tyr His Ala Ala Leu Lys Val Asp Leu Leu Gln Gly Ala
    210                 215                 220

Gly Asn Ser Ala Ala Arg Gly Ala Ile Ala Asp Thr Phe Arg Ser
225                 230                 235                 240

Ile Ser Thr Arg Glu Leu Val His Leu Glu Asp Ser Pro Asp Tyr Cys
                245                 250                 255

Leu Glu Asn Lys Thr Leu Gly Leu Leu Gly Thr Gly Arg Glu Cys
            260                 265                 270

Leu Arg Arg Gly Arg Ala Leu Gly Arg Trp Glu Leu Arg Ser Cys Arg
        275                 280                 285

Arg Leu Cys Gly Asp Cys Gly Leu Ala Val Glu Glu Arg Arg Ala Glu
    290                 295                 300

Thr Val Ser Ser Cys Asn Cys Lys Phe His Trp Cys Cys Ala Val Arg
305                 310                 315                 320

Cys Glu Gln Cys Arg Arg Val Thr Lys Tyr Phe Cys Ser Arg Ala
                325                 330                 335

Glu Arg Pro Arg Gly Gly Ala Ala His Lys Pro Gly Arg Lys Pro
            340                 345                 350
```

```
<210> SEQ ID NO 15
<211> LENGTH: 15
<212> TYPE: PRT
<213> ORGANISM: Homo sapiens

<400> SEQUENCE: 15

Arg Glu Thr Ala Phe Val His Ala Ile Ser Ser Ala Gly Val Met
 1               5                  10                  15

<210> SEQ ID NO 16
<211> LENGTH: 14
<212> TYPE: PRT
<213> ORGANISM: Homo sapiens

<400> SEQUENCE: 16

Arg Asn Cys Ser Leu Gly Asp Phe Asp Asn Cys Gly Cys Asp
 1               5                  10

<210> SEQ ID NO 17
<211> LENGTH: 13
<212> TYPE: PRT
<213> ORGANISM: Homo sapiens

<400> SEQUENCE: 17

Trp Leu Trp Gly Gly Cys Ser Asp Asn Val Gly Phe Gly
 1               5                  10

<210> SEQ ID NO 18
<211> LENGTH: 16
<212> TYPE: PRT
<213> ORGANISM: Homo sapiens

<400> SEQUENCE: 18

Cys Lys Cys His Gly Val Ser Gly Ser Cys Thr Thr Gln Thr Cys Trp
 1               5                  10                  15

<210> SEQ ID NO 19
<211> LENGTH: 12
<212> TYPE: PRT
<213> ORGANISM: Homo sapiens

<400> SEQUENCE: 19

Glu Leu Val His Leu Glu Asp Ser Pro Asp Tyr Cys
 1               5                  10

<210> SEQ ID NO 20
<211> LENGTH: 350
<212> TYPE: PRT
<213> ORGANISM: Mus musculus

<400> SEQUENCE: 20

Met Phe Leu Met Lys Pro Val Cys Val Leu Leu Val Thr Cys Val Leu
 1               5                  10                  15

His Arg Ser His Ala Trp Ser Val Asn Asn Phe Leu Met Thr Gly Pro
                20                  25                  30

Lys Ala Tyr Leu Val Tyr Ser Ser Val Ala Ala Gly Ala Gln Ser
            35                  40                  45

Gly Ile Glu Glu Cys Lys Tyr Gln Phe Ala Trp Asp Arg Trp Asn Cys
    50                  55                  60

Pro Glu Arg Ala Leu Gln Leu Ser Ser His Gly Gly Leu Arg Ser Ala
65                  70                  75                  80

Asn Arg Glu Thr Ala Phe Val His Ala Ile Ser Ser Ala Gly Val Met
                85                  90                  95
```

```
Tyr Thr Leu Thr Arg Asn Cys Ser Leu Gly Asp Phe Asp Asn Cys Gly
            100                 105                 110

Cys Asp Asp Ser Arg Asn Gly Gln Leu Gly Gly Gln Gly Trp Leu Trp
            115                 120                 125

Gly Gly Cys Ser Asp Asn Val Gly Phe Gly Glu Ala Ile Ser Lys Gln
130                 135                 140

Phe Val Asp Ala Leu Glu Thr Gly Gln Asp Ala Arg Ala Ala Met Asn
145                 150                 155                 160

Leu His Asn Asn Glu Ala Gly Arg Lys Ala Val Lys Gly Thr Met Lys
                165                 170                 175

Arg Thr Cys Lys Cys His Gly Val Ser Gly Ser Cys Thr Thr Gln Thr
                180                 185                 190

Cys Trp Leu Gln Leu Pro Glu Phe Arg Glu Val Gly Ala His Leu Lys
            195                 200                 205

Glu Lys Tyr His Ala Ala Leu Lys Val Asp Leu Leu Gln Gly Ala Gly
            210                 215                 220

Asn Ser Ala Ala Gly Arg Gly Ala Ile Ala Asp Thr Phe Arg Ser Ile
225                 230                 235                 240

Ser Thr Arg Glu Leu Val His Leu Glu Asp Ser Pro Asp Tyr Cys Leu
                245                 250                 255

Glu Asn Lys Thr Leu Gly Leu Leu Gly Thr Glu Gly Arg Glu Cys Leu
                260                 265                 270

Arg Arg Gly Arg Ala Leu Gly Arg Trp Glu Arg Arg Ser Cys Arg Arg
            275                 280                 285

Leu Cys Gly Asp Cys Gly Leu Ala Val Glu Glu Arg Arg Ala Glu Thr
            290                 295                 300

Val Ser Ser Cys Asn Cys Lys Phe His Trp Cys Cys Ala Val Arg Cys
305                 310                 315                 320

Glu Gln Cys Arg Arg Val Thr Lys Tyr Phe Cys Ser Arg Ala Glu
                325                 330                 335

Arg Pro Pro Arg Gly Ala Ala His Lys Pro Gly Lys Asn Ser
            340                 345                 350

<210> SEQ ID NO 21
<211> LENGTH: 354
<212> TYPE: PRT
<213> ORGANISM: Homo sapiens

<400> SEQUENCE: 21

Met Arg Ala Arg Pro Gln Val Cys Glu Ala Leu Leu Phe Ala Leu Ala
  1               5                  10                  15

Leu Gln Thr Gly Val Cys Tyr Gly Ile Lys Trp Leu Ala Leu Ser Lys
                 20                  25                  30

Thr Pro Ser Ala Leu Ala Leu Asn Gln Thr Gln His Cys Lys Gln Leu
             35                  40                  45

Glu Gly Leu Val Ser Ala Gln Val Gln Leu Cys Arg Ser Asn Leu Glu
         50                  55                  60

Leu Met His Thr Val Val His Ala Ala Arg Glu Val Met Lys Ala Cys
 65                  70                  75                  80

Arg Arg Ala Phe Ala Asp Met Arg Trp Asn Cys Ser Ser Ile Glu Leu
                 85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Ile Ser His Ala Ile Ala Arg
            115                 120                 125
```

Ala Cys Thr Ser Gly Asp Leu Pro Gly Cys Ser Cys Gly Pro Val Pro
    130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Met Lys
        195                 200                 205

Cys Lys Cys His Gly Val Ser Gly Ser Cys Ser Ile Arg Thr Cys Trp
    210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
        275                 280                 285

Val Gly Ser His Gly Thr Gln Asp Arg Gln Cys Asn Lys Thr Ser Asn
    290                 295                 300

Gly Ser Asp Ser Cys Asp Leu Met Cys Cys Gly Arg Gly Tyr Asn Pro
305                 310                 315                 320

Tyr Thr Asp Arg Val Val Glu Arg Cys His Cys Lys Tyr His Trp Cys
                325                 330                 335

Cys Tyr Val Thr Cys Arg Arg Cys Glu Arg Thr Val Glu Arg Tyr Val
            340                 345                 350

Cys Lys

<210> SEQ ID NO 22
<211> LENGTH: 15
<212> TYPE: PRT
<213> ORGANISM: Homo sapiens

<400> SEQUENCE: 22

Arg Glu Ser Ala Phe Val Tyr Ala Leu Ser Ala Ala Ile Ser
1               5                   10                  15

<210> SEQ ID NO 23
<211> LENGTH: 14
<212> TYPE: PRT
<213> ORGANISM: Homo sapiens

<400> SEQUENCE: 23

Arg Ala Cys Thr Ser Gly Asp Leu Pro Gly Cys Ser Cys Gly
1               5                   10

<210> SEQ ID NO 24
<211> LENGTH: 13
<212> TYPE: PRT
<213> ORGANISM: Homo sapiens

<400> SEQUENCE: 24

Asn Arg Trp Gly Gly Cys Ala Asp Asn Leu Ser Tyr Gly
1               5                   10

<210> SEQ ID NO 25

```
<211> LENGTH: 16
<212> TYPE: PRT
<213> ORGANISM: Homo sapiens

<400> SEQUENCE: 25

Cys Lys Cys His Gly Val Ser Gly Ser Cys Ser Ile Arg Thr Cys Trp
 1               5                  10                  15

<210> SEQ ID NO 26
<211> LENGTH: 12
<212> TYPE: PRT
<213> ORGANISM: Homo sapiens

<400> SEQUENCE: 26

Glu Leu Val Tyr Leu Gln Ser Ser Pro Asp Phe Cys
 1               5                  10

<210> SEQ ID NO 27
<211> LENGTH: 354
<212> TYPE: PRT
<213> ORGANISM: Mus musculus

<400> SEQUENCE: 27

Met Arg Ala Arg Pro Gln Val Cys Glu Ala Leu Leu Phe Ala Leu Ala
 1               5                  10                  15

Leu His Thr Gly Val Cys Tyr Gly Ile Lys Trp Leu Ala Leu Ser Lys
                20                  25                  30

Thr Pro Ala Ala Leu Ala Leu Asn Gln Thr Gln His Cys Lys Gln Leu
            35                  40                  45

Glu Gly Leu Val Ser Ala Gln Val Gln Leu Cys Arg Ser Asn Leu Glu
        50                  55                  60

Leu Met Arg Thr Ile Val His Ala Ala Arg Gly Ala Met Lys Ala Cys
 65                  70                  75                  80

Arg Arg Ala Phe Ala Asp Met Arg Trp Asn Cys Ser Ser Ile Glu Leu
                85                  90                  95

Ala Pro Asn Tyr Leu Leu Asp Leu Glu Arg Gly Thr Arg Glu Ser Ala
            100                 105                 110

Phe Val Tyr Ala Leu Ser Ala Ala Thr Ile Ser His Thr Ile Ala Arg
        115                 120                 125

Ala Cys Thr Ser Gly Asp Leu Pro Gly Cys Ser Cys Gly Pro Val Pro
130                 135                 140

Gly Glu Pro Pro Gly Pro Gly Asn Arg Trp Gly Gly Cys Ala Asp Asn
145                 150                 155                 160

Leu Ser Tyr Gly Leu Leu Met Gly Ala Lys Phe Ser Asp Ala Pro Met
                165                 170                 175

Lys Val Lys Lys Thr Gly Ser Gln Ala Asn Lys Leu Met Arg Leu His
            180                 185                 190

Asn Ser Glu Val Gly Arg Gln Ala Leu Arg Ala Ser Leu Glu Thr Lys
        195                 200                 205

Cys Lys Cys His Gly Val Ser Gly Ser Cys Ser Ile Arg Thr Cys Trp
210                 215                 220

Lys Gly Leu Gln Glu Leu Gln Asp Val Ala Ala Asp Leu Lys Thr Arg
225                 230                 235                 240

Tyr Leu Ser Ala Thr Lys Val Val His Arg Pro Met Gly Thr Arg Lys
                245                 250                 255

His Leu Val Pro Lys Asp Leu Asp Ile Arg Pro Val Lys Asp Ser Glu
            260                 265                 270

Leu Val Tyr Leu Gln Ser Ser Pro Asp Phe Cys Met Lys Asn Glu Lys
```

```
            275                 280                 285
Val Gly Ser His Gly Thr Gln Asp Arg Gln Cys Asn Lys Thr Ser Asn
        290                 295                 300

Gly Ser Asp Ser Cys Asp Leu Met Cys Cys Gly Arg Gly Tyr Asn Pro
305                 310                 315                 320

Tyr Thr Asp Arg Val Val Glu Arg Cys His Cys Lys Tyr His Trp Cys
                325                 330                 335

Cys Tyr Val Thr Cys Arg Arg Cys Glu Arg Thr Val Glu Arg Tyr Val
            340                 345                 350

Cys Lys

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
gaaatcccat caccatcttc cag                                         23

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
atgagtcctt ccacgatacc aaag                                        24

<210> SEQ ID NO 30
<211> LENGTH: 19
<212> TYPE: DNA
<213> ORGANISM: Artificial Sequence
<220> FEATURE:
<223> OTHER INFORMATION: Primer

<400> SEQUENCE: 30
tgttgcctgg ctgggtttc                                              19

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ctgtaagcag gttcgtggag                                             20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gtggatgcaa aggaaaggaa                                             20

<210> SEQ ID NO 33
<211> LENGTH: 20
<212> TYPE: DNA
```

```
<213> ORGANISM: Artificial Sequence
<220> FEATURE:
<223> OTHER INFORMATION: Primer

<400> SEQUENCE: 33
agccagcatg tcctgagagt                                              20

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
acccaagatg gtgccaactt c                                            21

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
cacaaccgtc tgttcctttt gatg                                         24

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
ggagtgtatt cgcatctacg acg                                          23

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
cgagttgggt ctgggtcatt tac                                          23

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
ccccactcgg atacttctta ctcc                                         24

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
ctcctggatg ccaatcttga tg                                           22
```

```
<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tttgtggatg tgcgggagag                                              20

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
atctgtgtgc ggcttgaact g                                            21

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
acacctcttt ccaaacaggc c                                            21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ggattgttaa actcaactct c                                            21

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
ggagcgagag aagaactttg cc                                           22

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
gaagcagcac cagtggaact tg                                           22

<210> SEQ ID NO 46
<211> LENGTH: 27
<212> TYPE: DNA
<213> ORGANISM: Artificial Sequence
<220> FEATURE:
<223> OTHER INFORMATION: Primer
```

```
<400> SEQUENCE: 46
cttggttatg gaccctaccc aggcatc                                          27

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
cactgcagca gctcgcccat agaa                                             24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
gctgcctggg ccacctcttt ctca                                             24

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
cccggtggta caggccttgc ttct                                             24

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
tcaacgagtg ccagtaccag                                                  20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ccctcggctt ggttgtagta                                                  20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tccagtttgc ttgggaacgc                                                  20

<210> SEQ ID NO 53
<211> LENGTH: 21
<212> TYPE: DNA
```

<213> ORGANISM: Artificial Sequence
<220> FEATURE:
<223> OTHER INFORMATION: Primer

<400> SEQUENCE: 53
ccatcacagc cacagttttc g          21

<210> SEQ ID NO 54
<211> LENGTH: 25
<212> TYPE: DNA
<213> ORGANISM: Artificial Sequence
<220> FEATURE:
<223> OTHER INFORMATION: Primer

<400> SEQUENCE: 54
catctgtctt ttcacctgtg tcctc          25

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
aatgctgtct cccgattggc          20

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
tctgggtgct cctgttcttc ctac          24

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
attggtgttg gcattcgtgg          20

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
actgtcccga ggcaagagtt tc          22

<210> SEQ ID NO 59
<211> LENGTH: 21
<212> TYPE: DNA
<213> ORGANISM: Artificial Sequence
<220> FEATURE:
<223> OTHER INFORMATION: Primer

<400> SEQUENCE: 59
gcatttccgc ttcaggtttt c          21

```
<210> SEQ ID NO 60
<211> LENGTH: 22
<212> TYPE: DNA
<213> ORGANISM: Artificial Sequence
<220> FEATURE:
<223> OTHER INFORMATION: Primer

<400> SEQUENCE: 60
tgctgacctc aagacccgat ac                                              22

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
tgtcgcttcc gttggatgtc                                                 20

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
tgccagttcc agttccgctt tg                                              22

<210> SEQ ID NO 63
<211> LENGTH: 21
<212> TYPE: DNA
<213> ORGANISM: Artificial Sequence
<220> FEATURE:
<223> OTHER INFORMATION: Primer

<400> SEQUENCE: 63
ttcacaccca cgaggttgtt g                                               21

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
tgagtgccag tttcagttcc g                                               21

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
cttgtttcct ctcttggacc cc                                              22

<210> SEQ ID NO 66
<211> LENGTH: 23
<212> TYPE: DNA
<213> ORGANISM: Artificial Sequence
<220> FEATURE:
<223> OTHER INFORMATION: Primer
```

<400> SEQUENCE: 66
ctgctccgat gatgtccagt atg                                    23

<210> SEQ ID NO 67
<211> LENGTH: 22
<212> TYPE: DNA
<213> ORGANISM: Artificial Sequence
<220> FEATURE:
<223> OTHER INFORMATION: Primer

<400> SEQUENCE: 67
cattctctgc cttgtgtccc tg                                     22

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
acttcggcgt gttagtgtcc                                        20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
catttgaggt gcatgtggtc                                        20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
ttccgatgct cctatgaagg                                        20

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
agacacccca tggcacttac                                        20

<210> SEQ ID NO 72
<211> LENGTH: 19
<212> TYPE: DNA
<213> ORGANISM: Artificial Sequence
<220> FEATURE:
<223> OTHER INFORMATION: Primer

<400> SEQUENCE: 72
gccgcttcta ccacagact                                         19

<210> SEQ ID NO 73
<211> LENGTH: 19
<212> TYPE: DNA

```
<213> ORGANISM: Artificial Sequence
<220> FEATURE:
<223> OTHER INFORMATION: Primer

<400> SEQUENCE: 73
ttcataccgc agtctcccc                                                    19

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
ggacacggac aggattgaca                                                   20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
acccacggaa tcgagaaaga                                                   20

<210> SEQ ID NO 76
<211> LENGTH: 32
<212> TYPE: DNA
<213> ORGANISM: Artificial Sequence
<220> FEATURE:
<223> OTHER INFORMATION: Primer

<400> SEQUENCE: 76
tagttaagct taccatggag ccccacctgc tc                                     32

<210> SEQ ID NO 77
<211> LENGTH: 36
<212> TYPE: DNA
<213> ORGANISM: Artificial Sequence
<220> FEATURE:
<223> OTHER INFORMATION: Primer

<400> SEQUENCE: 77
gcagctgacg tagcagcacc agtggaagat gcagtg                                 36

<210> SEQ ID NO 78
<211> LENGTH: 36
<212> TYPE: DNA
<213> ORGANISM: Artificial Sequence
<220> FEATURE:
<223> OTHER INFORMATION: Primer

<400> SEQUENCE: 78
gtagatgcga atacactcct ggcagctgac gtagca                                 36

<210> SEQ ID NO 79
<211> LENGTH: 44
<212> TYPE: DNA
<213> ORGANISM: Artificial Sequence
<220> FEATURE:
<223> OTHER INFORMATION: Primer

<400> SEQUENCE: 79
tgcttgaatt ccttgcaggt gtgcacgtcg tagatgcgaa taca                        44
```

```
<210> SEQ ID NO 80
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 80

Leu Arg Ala Lys Tyr Ser Leu Phe Lys Pro Pro Thr Glu Arg Asp Leu
 1               5                  10                  15

<210> SEQ ID NO 81
<211> LENGTH: 19
<212> TYPE: RNA
<213> ORGANISM: Artificial Sequence
<220> FEATURE:
<223> OTHER INFORMATION: Synthetically generated siRNA

<400> SEQUENCE: 81
ggaaaaaugc cacugcauc                                              19

<210> SEQ ID NO 82
<211> LENGTH: 19
<212> TYPE: RNA
<213> ORGANISM: Artificial Sequence
<220> FEATURE:
<223> OTHER INFORMATION: Synthetically generated siRNA

<400> SEQUENCE: 82
ggaguguauu cgcaucuac                                              19

<210> SEQ ID NO 83
<211> LENGTH: 19
<212> TYPE: RNA
<213> ORGANISM: Artificial Sequence
<220> FEATURE:
<223> OTHER INFORMATION: Synthetically generated siRNA

<400> SEQUENCE: 83
ggcuuaucuu ugcacaugu                                              19

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
gatttgatgg agttggacat gg                                          22

<210> SEQ ID NO 85
<211> LENGTH: 22
<212> TYPE: DNA
<213> ORGANISM: Artificial Sequence
<220> FEATURE:
<223> OTHER INFORMATION: Primer

<400> SEQUENCE: 85
tgttcttgag tgaaggactg ag                                          22
```

WNT PROTEINS AND DETECTION AND TREATMENT OF CANCER

CROSS-REFERENCE TO RELATED APPLICATIONS

This application is the National Stage of International Application No. PCT/US2005/033775 filed on Sep. 21, 2005, which is a continuation-in-part of International Application No. PCT/US05/000267, filed Jan. 5, 2005, which claims the benefit of U.S. Provisional Application No. 60/612,098, filed Sep. 21, 2004. The contents of all applications are hereby incorporated by reference in their entirety.

STATEMENT AS TO FEDERALLY SPONSORED RESEARCH

This invention was made with Government support under National Institutes of Health Grant Nos. CA035711 and AA002666. The Government has certain rights in this invention.

TECHNICAL FIELD

This invention relates to detection and treatment of liver cancer.

BACKGROUND

Hepatocellular carcinoma (HCC) is the major primary malignant tumor of the liver. Although viral etiological factors have been identified, the molecular mechanisms that contribute to tumor progression during hepatocarcinogenesis remain largely unknown. The Frizzled family of proteins is composed of ten or more seven-transmembrane proteins that act as receptors for Wnt proteins. The Wnt/Frizzled signaling network influences diverse biological processes ranging from cell fate determination to cell motility and proliferation.

β-catenin is a multifactorial protein with a role in cell-cell adhesion that involves strengthening the linkage of cadherin and α-catenin to the actin cytoskeleton. In the absence of Wnt/Frizzled signaling, β-catenin is phosphorylated by interactions with glycogen synthase kinase (GSK)-3β, and forms a complex with axin and the adenomatous polyposis coli protein (APC). Subsequently β-catenin is targeted for degradation by the ubiquitinproteasome system. In contrast, binding of a Wnt ligand to its Frizzled receptor stabilizes intracellular β-catenin through the inhibition of GSK-3β enzymatic activity. Subsequently, β-catenin translocates into the nucleus in association with high mobility group domain factors such as Tcf/Lef. This complex is associated with transcriptional up-regulation of growth regulatory and cell migration related genes.

SUMMARY

The present invention is based, in part, on the discovery that Wnt 3, 8b and 11 are ligands for Frizzled 7, which is commonly overexpressed at the mRNA and protein level in HCC, for example, in hepatitis B virus (HBV) related HCC. Liver cancer cells that overexpress Frizzled 7 exhibit enhanced cell motility and migration. Overexpression appears to be an early event during the multi-step process of hepatocyte transformation, and therefore Frizzled 7 and Wnt 3, 8b and 11 are novel molecular targets for therapy of liver cancer.

Accordingly, in one aspect, the invention provides a method for identifying an anti-cancer agent. The method includes selecting a test compound that binds to a polypeptide comprising the amino acid sequence of a Wnt 3, Wnt 8b or Wnt 11 protein or a FZD-binding fragment thereof; and optionally determining whether the test compound is capable of (i) reducing Wnt/FZD 7 signaling in a cell, (ii) reducing liver cancer cell motility, reducing β-catenin accumulation in a liver cancer cell; or (iv) treating liver cancer in vitro or in vivo; wherein a test compound that is capable of at least one of (i) to (iv) is an anti-cancer agent. In some embodiments, selecting a test compound can include providing a polypeptide comprising the amino acid sequence of a Wnt 3, Wnt 8b or Wnt 11 polypeptide or a FZD-binding fragment thereof, contacting the polypeptide with a test compound, detecting binding between the polypeptide and the test compound; and selecting the test compound if it binds to the polypeptide. The polypeptide to which a test compound binds can be a (i) naturally occurring polypeptide, a (ii) recombinant polypeptide, (iii) a polypeptide expressed on the surface of a cell or (iv) an isolated polypeptide. Where the polypeptide includes the amino acid sequence of a Wnt 3 protein, the polypeptide can include any one of SEQ ID NO: 8 to 12. Where the polypeptide includes the amino acid sequence of a Wnt 8b protein, the polypeptide can include any one of SEQ ID NO: 15 to 19. Where the polypeptide includes the amino acid sequence of a Wnt 11 protein, the polypeptide can include any one of SEQ ID NO: 22 to 26. In certain embodiments, the polypeptide includes any one of SEQ ID NO:7 to 27 and at least one non-Wnt sequence. The test compound can be selected from the group consisting of polypeptides, ribonucleic acids, small molecules (e.g., small organic molecules), and deoxyribonucleic acids.

Anti-cancer agents identified by the methods of identifying a cancer agent described herein include, but are not limited to, an anti-Wnt antibody, e.g., a monoclonal antibody, FZD7 receptors, Wnt-binding fragments of FZD7 receptors, and other Wnt-binding compounds. Anti-cancer agents identified by these methods can be used in the treatment of cancer, e.g., liver cancer. Additionally, an anti-cancer agent identified by these methods can be used to manufacture a medicament for treating liver cancer or reducing the motility of liver cancer cells in a patient.

In another aspect, the invention includes a method of identifying a candidate anti-cancer agent. The method includes (a) providing a first polypeptide that: (i) comprises a FZD polypeptide (e.g., a FZD 7 polypeptide) or a fragment thereof; and (ii) displays Wnt (e.g., Wnt 3, 8b or 11)-binding ability; (b) providing a second polypeptide that: (i) comprises a Wnt polypeptide (e.g., a Wnt 3, 8b or 11 polypeptide) or a fragment thereof; and (ii) displays FZD (e.g., FZD 7) binding ability; (c) contacting the first and second polypeptides in the presence of a test compound; and (d) comparing the level of binding between the first and second polypeptides in the presence of the test compound with the level of binding in the absence of the test compound, wherein a reduced level of binding in the presence of the test compound than in its absence indicates that the test compound is a candidate anti-cancer agent. The method can further include: (e) determining whether the candidate anti-cancer agent is capable of: (i) reducing Wnt/FZD 7 signaling in a cell; (ii) reducing cancer cell motility; (iii) reducing β-catenin accumulation in a cancer cell; or (iv) treating cancer in vitro or in vivo; wherein a candidate that is capable of at least one of (i) to (iv) is an anti-cancer agent. The test compound can be selected from the group consisting of polypeptides, ribonucleic acids, small molecules (e.g., small organic molecules), and deoxyribonucleic acids. The Wnt polypeptide can include, e.g., SEQ ID NO:8 to 12, 15 to 19, and/or 22 to 26. The FZD polypeptide can include, e.g., SEQ ID NO:1, 2 and/or 3.

In certain embodiments, the first polypeptide is a first fusion protein comprising a FZD polypeptide (e.g., FZD 7 polypeptide) fused to (i) a transcription activation domain of a transcription factor or (ii) a DNA-binding domain of a transcription factor; the second polypeptide is a second fusion protein comprising a Wnt polypeptide (e.g., a Wnt 3, 8b, or 11 polypeptide) fused to (i) a transcription activation domain of a transcription factor or (ii) a DNA-binding domain of a transcription factor, wherein the Wnt polypeptide is fused to a domain different from that fused to the Wnt polypeptide; and binding of the first and second polypeptides is detected as reconstitution of a transcription factor.

Anti-cancer agents (and/or candidate anticancer agents) identified by the methods described herein can be used in the treatment of cancer, for example, liver cancer. Additionally, anti-cancer agents (and/or candidate anticancer agents) identified by the methods described herein can be used in the manufacture of a medicament for treating cancer, for example, liver cancer.

In still another aspect, the invention provides a method of determining whether a cell (e.g., a liver cell) is, or is at risk for becoming, a cancer cell. The method includes (a) providing a test cell (e.g., a liver cell); (b) determining whether the cell's level of FZD7 and/or Wnt3 expression is higher, and/or FZD8 and/or Wnt11 expression is lower, than that of a control cell; and (c) classifying the test cell as (i) a cancer cell or (ii) at risk for becoming a cancer cell, if the test cell's level of FZD7 and/or Wnt3 expression is higher, and/or the test cell's level of FZD8 and/or Wnt11 expression is lower, than that of the control cell. Where the method includes determining the cell's level of FZD7 and/or Wnt3 expression, the method can further include: (c) determining whether the test cell's level of FZD8 and/or Wnt11 expression is lower than that of a control cell, wherein a lower level of expression of FZD8 and/or Wnt11 indicates that the test cell is, or is at risk for becoming, a cancer cell. Where the method includes determining the cell's level of FZD8 and/or Wnt11 expression, the method can further include: (c) determining whether the test cell's level of FZD7 and/or Wnt3 expression is higher than that of a control cell, wherein a higher level of expression of FZD7 and/or Wnt3 indicates that the test cell is, or is at risk for becoming, a cancer cell.

In a further aspect, the invention provides a method of determining whether a patient is suffering from or at risk for cancer, e.g., whether a test tissue sample comes from a patient that is suffering from or at risk for cancer. The method can include: providing a test tissue sample (e.g., a liver tissue such as tumerous or peritumorous liver tissue) obtained from a patient, and (b) determining whether the level of FZD7 and/or Wnt3 expression is higher, and/or whether the level of FZD8 and/or Wnt11 expression is lower, in the test tissue sample than that in a comparable tissue sample obtained from a healthy individual, wherein a higher level of expression of FZD7 and/or Wnt3 and/or a lower level of expression of FZD8 and/or Wnt11 in the test tissue sample is an indication that the sample is from a patient suffering from or at risk for cancer. Where the method includes determining the level of FZD7 and/or Wnt3 expression, the method can further include: (c) determining whether the level of FZD8 and/or Wnt11 expression in the test tissue sample is lower than that in a tissue sample obtained from a healthy individual, wherein a lower level of expression of FZD8 and/or Wnt11 is an indication that the sample comes from a patient is suffering from or at risk for cancer. Where the method includes determining the level of FZD8 and/or Wnt11 expression, the method can further include: (c) determining whether the level of FZD7 and/or Wnt3 expression in the test tissue sample is higher than that in a tissue sample obtained from a healthy individual, wherein a higher level of expression of FZD7 and/or Wnt3 is an indication that the patient is suffering from or at risk for cancer.

In any of the methods described herein, determining the level of FZD7, FZD8, Wnt3 or Wnt11 expression can include determining the amount of FZD7, FZD8, Wnt3 or Wnt11 mRNA in the cell, e.g., using a Northern blot assay or an RT-PCR assay. In other embodiments, determining the level of expression can include determining the amount of FZD7, FZD8, Wnt3 or Wnt11 protein in the cell, e.g., using an anti-Wnt antibody, e.g., an antibody that binds to SEQ ID NOS:7 or 80.

In still another aspect, the invention includes a method of treating cancer (e.g., liver cancer) in a patient. The method includes administering to the patient an effective amount of a compound that reduces Wnt/FZD7 signaling in FZD7-expressing cells of the patient and that is optionally non-lethal to the FZD7-expressing cells. In one embodiment, the compound is a compound that reduces FZD7 and/or Wnt3 expression in the patient and/or increases Wnt11 expression in the patient. In another embodiment, the compound is a compound that binds Wnt 3, Wnt 8b, Wnt 11, FZD7 or FZD8 in the patient. The compound can be, e.g., an antisense oligonucleotide, a double stranded RNA (dsRNA) that includes a nucleotide sequence that hybridizes under physiological conditions to a Wnt nucleotide sequence, an isolated FZD7 receptor or a Wnt3 binding fragment thereof, a genetic construct encoding a Wnt polypeptide (e.g., a Wnt11 polypeptide) or truncated form of FZD7 (e.g., a form of FZD7 lacks FZD7's intracellular and/or transmembrane domain), and/or an anti-FZD and/or anti-Wnt antibody (e.g., anti-Wnt3 antibody). The compound can be administered by any route, e.g., by administration to the patient's liver. In certain embodiments, the compound is an antibody that binds to SEQ ID NO:7 or 80. In other embodiments, the compound is a siRNA comprising SEQ ID NO:81, 82 or 83.

In yet another aspect, the invention includes a method of reducing motility of a cancer cell (e.g., a liver cancer cell). The method includes administering to the cell an effective amount of a compound capable of reducing Wnt/FZD7 signaling in the cell and which is optionally non-lethal to the cell. In one embodiment, the compound is a compound that reduces FZD7 and/or Wnt3 expression in the patient and/or increases Wnt11 expression in the patient. In another embodiment, the compound is a compound that binds Wnt 3, Wnt 8b, Wnt 11, FZD7 or FZD8 in the patient. The compound can be, e.g., an antisense oligonucleotide, a double stranded RNA (dsRNA) that includes a nucleotide sequence that hybridizes under physiological conditions to a Wnt nucleotide sequence, an isolated FZD7 receptor or a Wnt3 binding fragment thereof, a genetic construct encoding a Wnt polypeptide (e.g., a Wnt11 polypeptide) or truncated form of FZD7 (e.g., a form of FZD7 lacks FZD7's intracellular and/or transmembrane domain), and/or an anti-FZD and/or anti-Wnt antibody (e.g., anti-Wnt3 antibody). The compound can be administered by any route, e.g., by administration to the patient's liver. In certain embodiments, the compound is an antibody that binds to SEQ ID NO:7 or 80. In other embodiments, the compound is a siRNA comprising SEQ ID NO:81, 82 or 83.

In another aspect, the invention includes the use of a compound that reduces Wnt/FZD7 signaling in FZD7-expressing cells in the manufacture of (i) a medicament for the treatment of liver cancer or (ii) a medicament that reduces the motility of liver cancer cells. Optionally, the medicament is non-lethal to FZD7 expressing cells. In one embodiment, the compound is a compound that reduces FZD7 and/or Wnt3 expression in the patient and/or increases Wnt11 expression in the patient. In another embodiment, the compound is a compound that binds Wnt 3, Wnt 8b, Wnt 11, FZD7 or FZD8 in the patient. The compound can be, e.g., an antisense oligonucleotide, a double stranded RNA (dsRNA) that includes a nucleotide sequence that hybridizes under physiological conditions to a Wnt nucleotide sequence, an isolated FZD7 receptor or a Wnt3 binding fragment thereof, a genetic construct encoding a Wnt polypeptide (e.g., a Wnt11 polypeptide) or truncated form of FZD7 (e.g., a form of FZD7 lacks FZD7's intracellular and/or transmembrane domain), and/or an anti-FZD and/or anti-Wnt antibody (e.g., anti-Wnt3 antibody).

In certain aspects, the invention includes an anti-Wnt antibody, e.g., an anti-Wnt3 antibody, e.g., an antibody that binds to SEQ ID NO:7 or the amino acid sequence LRAKYSLFKPPTERDL (SEQ ID NO:80). The antibody can be included in a pharmaceutical composition suitable for administration to a patient.

In other aspects, the invention includes the use of any of the compounds described herein in the preparation of a pharmaceutical composition for the treatment or prevention of a condition described herein, e.g., cancer, e.g., liver cancer. The composition can be used in a method for treating cancer and/or for reducing motility of a cancer cell in accordance with the methods described herein. The composition can be in any form described herein, e.g., a liquid or solid composition. In certain embodiments, the compound is an antibody, e.g., an anti-Wnt antibody, e.g., an antibody that binds to SEQ ID NO:7 or the amino acid sequence LRAKYSLFKPPTERDL (SEQ ID NO:80). In other embodiments, the compound is an siRNA, e.g., an siRNA comprising the nucleic acid sequence WNT3-1: 5'-GGAAAAAUGCCACUGCAUC-3' (SEQ ID NO:81), WNT3-2: 5'-GGAGUGUAUUCGCAUCUAC-3' (SEQ ID NO:82), and/or WNT3-3: 5'-GGCUUAUCUUUGCACAUGU-3' (SEQ ID NO:83)).

Also included within the invention are nucleic acids described herein (e.g., a primer described in Table 1, below) that are useful for detecting Wnt proteins.

Unless otherwise defined, all technical and scientific terms used herein have the same meaning as commonly understood by one of ordinary skill in the art to which this invention belongs. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

DESCRIPTION OF DRAWINGS

FIG. 4A: Negative control. FIG. 4B: β-catenin stained peritumoral tissues. The hepatocytes showed typical membranous staining. FIG. 4C: β-catenin stained HCC tissues, which display nuclear accumulation of β-catenin Note the nuclear staining as well as the increased cytoplasmic staining of β-catenin. FIG. 4D: HCC tissues, which display no nuclear or cytoplasmic accumulation of β-catenin.

FIG. 6B is representative of this effect in Huh7 cells.

FIGS. 8A-8E illustrate exemplary FZD7, FZD8, Wnt3, Wnt 8b and Wnt 11 human and mouse amino acid sequences, including putative binding motifs.

DETAILED DESCRIPTION

Figure 1A:
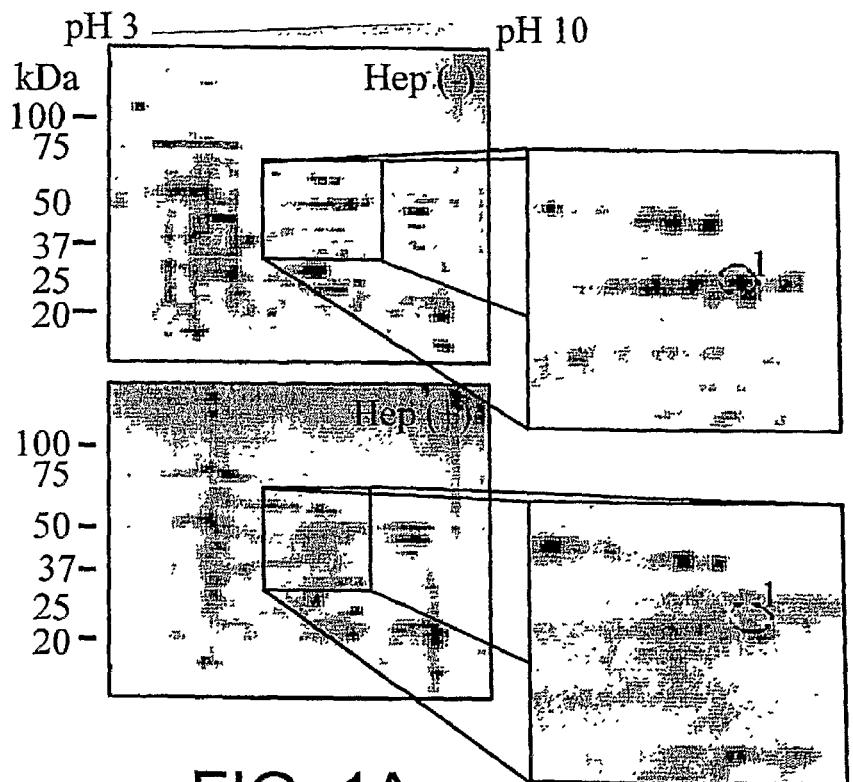
FIG. 1A is a set of pictures of silver-stained two-dimensional SDS-PAGE gels illustrating a pattern of fractionated heparan sulfate proteoglycans (HSPGs) from Huh7 cells following heparin treatment (Hep+) or no treatment (Hep−) of the Huh7 cells. The 0.25 M NaCl fractions from heparin affinity chromatography were separated onto first-dimensional pH 3-10 nonlinear IPG gels and second-dimensional 4-12% gradient NuPAGE gels. A protein spot (circled; hereinafter referred to as "spot 1") from the heparin-untreated fraction showed increased expression.

This invention is based, at least in part, on the discovery that particular Frizzled (FZD) proteins, e.g., FZD 7 and 8, are associated with certain cancers, such as liver cancer, and that Wnt 3, 8b and 11 are FZD 7 ligands. Accordingly, the present specification provides, inter alia, methods of using Wnt and FZD proteins, genes, FZD-specific antibodies and probes in diagnosis and treatment of cancer and for screening test compounds for an ability to treat cancer. Also disclosed are compounds useful for treating cancer such as liver cancer.

I. Nucleic Acids, Proteins, Vectors, and Host Cells

The terms "Frizzled," "FZD," "Frizzled protein" and "Frizzled receptor" refer to a family of mammalian proteins related to the *Drosophila* Frizzled genes, which play a role in the development of tissue polarity. The Frizzled family comprises at least 10 mammalian genes. Exemplary human Frizzled receptors include Frizzled 1, Frizzled 2, Frizzled 3, Frizzled 4, Frizzled 5, Frizzled 6, Frizzled 7, Frizzled 8, Frizzled 9 and Frizzled 10. Frizzled receptors are involved in a dynamic model of transmembrane signal transduction analogous to G-protein-coupled receptors with amino-terminal ligand binding domains.

The terms "Wnt protein," "Wnt ligand" and "Wnt" refer to a family of mammalian proteins related to the *Drosophila* segment polarity gene, wingless. In humans, the Wnt family of genes typically encode 38 to 43 kDa cysteine rich glycoproteins having hydrophobic signal sequence and a conserved asparagine-linked oligosaccharide consensus sequence (see e.g., Shimizu et al., Cell Growth Differ 8:1349-1358 (1997)). The Wnt family contains at least 19 mammalian members. Exemplary Wnt proteins include Wnt-1, Wnt-2, Wnt-2b (also known as Wnt-13), Wnt-3, Wnt-3A, Wnt-4, Wnt-5A, Wnt-5B, Wnt-6, Wnt-7A, Wnt-7B, Wnt-8A, Wnt-8B, Wnt-10A, Wnt-10B, Wnt-11, Wnt 14, Wnt 15, and Wnt 16.

In addition to Wnt ligands, a family of secreted Frizzled-related proteins (sFRPs) has been isolated. sFRPs appear to function as soluble endogenous modulators of Wnt signaling by competing with the membrane-spanning Frizzled receptors for the binding of secreted Wnt ligands. sFRPs can either antagonize Wnt function by binding the protein and blocking access to its cell surface signaling receptor, or they can enhance Wnt activity by facilitating the presentation of ligand to the Frizzled receptors.

The term "Wnt/FZD signaling pathway" refers to an intracellular signal transduction pathway that is initiated by an interaction between a Frizzled receptor, e.g., FZD 7, and one or more of its ligands, e.g., a Wnt protein, e.g., Wnt 3, 8b or 11. Typically, a Wnt/FZD interaction involves binding of a Wnt protein, e.g., Wnt 3, 8b or 11, to a Frizzled receptor, e.g., FZD 7, leading to activation of a signal transduction pathway. In some instances, activation of the Wnt/Frizzled signaling pathway will lead to induction of downstream-Wnt and/or FZD-inducible genes. A "downstream Wnt/FZD regulated gene product" is a protein or RNA that is regulated (e.g., up- or down-regulated) as a result of signaling by a Wnt/FZD signaling pathway.

The invention includes the use of certain FZD and Wnt nucleic acids. For example, the present invention includes the use of certain FZD 7 and 8 nucleic acids, such as those that encode the amino acid sequences of the exemplary human and mouse FZD 7 (SEQ ID NOs:1 and 3, respectively) and 8 (SEQ ID NO:4 and 6, respectively) receptors set forth in FIGS. 8A to 8E. As another example, the invention includes the use of certain Wnt 3, 8b, and 11 nucleic acids, such as those that encode the amino acid sequences of the exemplary human and mouse Wnt 3 (SEQ ID NOs:7 and 13, respectively), 8b (SEQ ID NOs:14 and 20, respectively), and 11 (SEQ ID NOs:21 and 27, respectively) proteins set forth in FIGS. 8A to 8E.

Also included within the present invention are the use of certain fragments of FZD and Wnt nucleic acids, e.g., a fragment of a nucleic acid sequence that encodes SEQ ID NOs:1, 3, 4, 6, 7, 13, 14, 20, 21, or 27. Fragments of FZD or Wnt nucleic acids encode at least one useful fragment of a FZD or Wnt polypeptide (e.g., a human or rodent polypeptide), respectively, such as a binding domain (e.g., a CRD domain) or other useful fragment. For example, a useful fragment of a FZD nucleic acid may encode a fragment of a FZD receptor having binding activity, e.g., a fragment corresponding to SEQ ID NO:3 or 5. As another example, a useful fragment of an Wnt nucleic acid may encode a fragment of a Wnt polypeptide having binding activity, e.g., a fragment corresponding to any one or more of SEQ ID NOs:8 to 12, 15 to 19 and 22 to 26.

FZD and Wnt nucleic acids described herein include both RNA and DNA, including genomic DNA and synthetic (e.g., chemically synthesized) DNA. Nucleic acids can be double-stranded or single-stranded. Where single-stranded, the nucleic acid can be a sense strand or an antisense strand. Nucleic acids can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a nucleic acid the structure of which is not identical to that of any naturally occurring nucleic acid or to that of any spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells; and (iii) cell clones, e.g., as these occur in a DNA library such as a cDNA or genomic DNA library.

In some embodiments, the invention includes the use of nucleic acid sequences that are substantially homologous to a FZD or Wnt nucleic acid. A nucleic acid sequence that is "substantially homologous" to a FZD or Wnt nucleic acid is at least 75% homologous to FZD or Wnt nucleic acid sequences that encode any one of SEQ ID NOs:1 to 27. For example, substantially homologous nucleic acid sequences can be at least about 80%, 85%, 90%, 95%, 98%, or at least about 99% homologous to sequences that encode SEQ ID NOs:1 to 27. For purposes of comparison of nucleic acids, the length of the reference nucleic acid sequence will be at least 50 nucleotides, but can be longer, e.g., at least 60 nucleotides, or more nucleotides.

As used herein, "percent homology" of two amino acid sequences or two nucleic acid sequences is determined using the algorithm of Karlin and Altschul (1990) *Proc. Nat'l Acad. Sci. USA* 87:2264-2268, modified as in Karlin and Altschul (1993) *Proc. Nat'l Acad. Sci. USA* 90:5873-5877. Such an algorithm is incorporated into the NBLAST and XBLAST programs of Altschul, et al. (1990); *J. Mol. Biol.* 215:403-410. BLAST nucleotide searches are performed with the NBLAST program, score=100, wordlength=12 to obtain nucleotide sequences homologous to FZD or Wnt nucleic acid molecules used in the invention. BLAST protein searches are performed with the XBLAST program, score=50, wordlength=3 to obtain amino acid sequences homologous to a reference polypeptide. To obtain gapped alignments for comparison purposes, Gapped BLAST is utilized as described in Altschul et al., (1997) *Nucleic Acids Res.* 25:3389-3402. When utilizing BLAST and Gapped BLAST programs, the default parameters of the respective programs (e.g., XBLAST and NBLAST) are used. See the World Wide Web at address ncbi.nlm.nih.gov.

The invention also includes the use of nucleic acids that hybridize under stringent hybridization conditions (as defined herein) to all or a portion of nucleotide sequences that encode any of SEQ ID NOs:1 to 27, or to a complement of such nucleic acid sequences. The hybridizing portion of the hybridizing nucleic acids is typically at least 15 (e.g., 20, 25, 30, or 50) nucleotides in length. The hybridizing portion of the hybridizing nucleic acid is at least about 75% (e.g., at least 80%, 90%, 95% or 98%) identical to the sequence of a portion or all of a nucleic acid encoding an FZD or Wnt polypeptide, or to its complement. Hybridizing nucleic acids of the type described herein can be used, for example, as a cloning probe, a primer (e.g., a PCR primer), or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. IF sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al.

(eds.), 1995, Current Protocols in Molecular Biology, (John Wiley & Sons, N.Y.) at Unit 2.10.

Nucleic acids that hybridize to nucleotide sequence that encode any of SEQ ID NOs:1 to 27 are considered "antisense oligonucleotides."

Also included in the invention are genetic constructs (e.g., vectors and plasmids) that include a FZD and/or Wnt nucleic acid described herein, operably linked to a transcription and/or translation sequence to enable expression, e.g., expression vectors. A selected nucleic acid, e.g., a DNA molecule encoding a FZD or Wnt polypeptide, is "operably linked" to another nucleic acid molecule, e.g., a promoter, when it is positioned in such a way that the other molecule can direct transcription and/or translation of the selected nucleic acid. For example, the selected nucleic acid can be positioned adjacent to the other nucleic acid molecule.

Also included in the invention are various engineered cells which contain a FZD and/or Wnt nucleic acid described herein. For example, the invention includes transformed host cells, i.e., cells into which (or into an ancestor of which) has been introduced, by means of recombinant DNA techniques, a nucleic acid encoding a FZD and/or Wnt polypeptide. Both prokaryotic and eukaryotic cells are included, e.g., mammalian cells (e.g., liver cells), fungi, and bacteria (such as *Escherichia coli*), and the like. An engineered cell exemplary of the type included in the invention is a liver cell that overexpresses a FZD 7 transgene.

A cell that "overexpresses FZD" is a cancer cell and/or transgenic cell in which expression of a particular FZD protein, such as FZD 7 and/or 8, is at least about 1.5 times, e.g., at least about 2, 3, 4 or 5 times, the level of expression in a non-cancer cell or non-transgenic cell, respectively, from the same tissue type. In some embodiments, FZD expression in a cell can be compared to expression in a non-cancer or non-transgenic cell of a different tissue-type or a panel of non-cancer or non-transgenic cells of a different tissue type. In addition, expression of one type of FZD protein (e.g., FZD 7) can be compared to other FZD proteins in the same cell. Methods for determining the level of expression of a particular gene are well known in the art. Such methods include, but are not limited to, RT-PCR, real time PCR and use of antibodies against the gene products.

The use of certain FZD and Wnt polypeptides are also included within the present invention. Examples of FZD polypeptides used in the present invention are human and mouse FZD polypeptides, such as those shown in SEQ ID NOs:1 and 3, respectively, and SEQ ID NOs:4 and 6, respectively. Examples of Wnt polypeptides used in the present invention are human and mouse Wnt 3, 8b and 11 polypeptides, such as those shown in SEQ ID NOs:7, 13, 14, 20, 21 and 27. Also included used in the present invention are certain fragments of FZD and Wnt polypeptides, e.g., fragments of SEQ ID NOs:1, 3, 4, 6, 7, 13, 14, 20, 21 and 27. Fragments of FZD and Wnt polypeptides may include at least one binding domain, or other useful portion of a full-length FZD and Wnt polypeptide. For example, useful fragments of FZD and Wnt polypeptides include, but are not limited to, fragments having binding activity (e.g., SEQ ID NOs: 2, 5, 8 to 12, 15 to 19, and 22 to 26).

The terms "protein" and "polypeptide" both refer to any chain of amino acids, regardless of length or post-translational modification (e.g., glycosylation or phosphorylation). Thus, the terms "Frizzled protein," "Wnt protein," "Frizzled polypeptide," and "Wnt polypeptide" include full-length naturally occurring isolated proteins, as well as recombinantly or synthetically produced polypeptides that correspond to the full-length naturally occurring proteins, or to a fragment of the full-length naturally occurring or synthetic polypeptide.

As discussed above, the terms "Frizzled polypeptide," and "Wnt polypeptide" include biologically active fragments of naturally occurring or synthetic FZD and Wnt polypeptides, respectively. Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid that encodes the polypeptide. Expression of such mutagenized DNA can produce polypeptide fragments. Digestion with "end-nibbling" endonucleases can generate DNAs that encode an array of fragments. DNAs that encode fragments of a protein can also be generated, e.g., by random shearing, restriction digestion, chemical synthesis of oligonucleotides, amplification of DNA using the polymerase chain reaction, or a combination of the above-discussed methods. Fragments can also be chemically synthesized using techniques known in the art, e.g., conventional Merrifield solid phase FMOC or t-Boc chemistry.

A purified or isolated compound is a composition that is at least 60% by weight the compound of interest, e.g., a FZD polypeptide, Wnt polypeptide, or antibody. For example, the preparation can be at least 75% (e.g., at least 90%, 95%, or even 99%) by weight the compound of interest. Purity can be measured by any appropriate method known in the art, e.g., column chromatography, polyacrylamide gel electrophoresis, or HPLC analysis.

In certain embodiments, FZD and Wnt polypeptides include sequences substantially identical to all or portions of a naturally occurring FZD and Wnt polypeptides. Polypeptides "substantially homologous" to the FZD and Wnt polypeptide sequences described herein have an amino acid sequence that is at least 65% (e.g., at least 75%, 80%, 85%, 90%, 95% or 99%, e.g., 100%), homologous to an amino acid sequence represented by SEQ ID NOs:1 to 27 (measured as described herein). For purposes of comparison, the length of the reference FZD and Wnt polypeptide sequence can be at least 16 amino acids, e.g., at least 20 or 25 amino acids.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The invention also includes the use of fusion proteins (and nucleic acids that encode such fusion proteins) in which a portion of a FZD (e.g., FZD 7 and/or 8) or Wnt (e.g., Wnt 3, 8b and/or 11) polypeptide is fused to an unrelated polypeptide (e.g., a marker polypeptide or a fusion partner) to create a fusion protein. For example, the polypeptide can be fused to a hexa-histidine tag or a FLAG tag to facilitate purification of bacterially expressed polypeptides or to a hemagglutinin tag or a FLAG tag to facilitate purification of polypeptides expressed in eukaryotic cells. The invention also includes, for example, the use of isolated polypeptides (and the nucleic acids that encode these polypeptides) that include a first portion and a second portion, wherein the first portion includes, e.g., a FZD or Wnt polypeptide, and the second portion includes an unrelated polypeptide, e.g., an immunoglobulin constant (Fc) region or a detectable marker.

The fusion partner can be, for example, a polypeptide that facilitates secretion, e.g., a secretory sequence. Such a fused polypeptide is typically referred to as a preprotein. The secretory sequence can be cleaved by the host cell to form the mature protein. Also within the invention are nucleic acids that encode a FZD and/or Wnt polypeptide fused to a polypeptide sequence to produce an inactive preprotein. Preproteins can be converted into the active form of the protein by removal of the inactivating sequence.

II. Methods for Detecting Cancer

Without being bound by theory, it appears that various FZD proteins, e.g., FZD 7 and 8, and FZD ligands, e.g., Wnt3 and 11, are important in cancer, e.g., liver cancer. In particular, hepatocytes appear to overexpress FZD 7 and Wnt3 early during the process of transformation, e.g., prior to the development of HCC. Similarly, such cells often underexpress FZD 8 and/or Wnt 11. It appears that Wnt 3, 8b and 11 are FZD 7 ligands.

Accordingly, the present invention provides methods of detecting cancer cells, facilitating the diagnosis of the presence and severity (e.g., tumor grade, tumor burden, and the like) of cancer in a patient, facilitating a determination of the prognosis of a patient and assessing the responsiveness of the patient to therapy (e.g., by providing a measure of therapeutic effect through, for example, assessing tumor burden during or following a chemotherapeutic regimen).

Detection can be based on detection of a polynucleotide (e.g., a FZD 7, FZD 8, Wnt 3 and/or Wnt 11 polynucleotide) that is differentially expressed in a cancer cell (e.g., as compared to a non-cancer cell) and/or detection of a polypeptide (e.g., a FZD 7 FZD 8, Wnt 3 and/or Wnt 11 polypeptide) encoded by a polynucleotide that is differentially expressed in a cancer cell. The detection methods of the invention can be conducted in vitro or in vivo, on a biological sample, e.g., isolated cells and/or whole tissues.

A "biological sample" as used herein is a sample of biological tissue or fluid that contains nucleic acids or polypeptides, e.g., a FZD 7 protein, polynucleotide or transcript. Such samples include, but are not limited to, tissue obtained from, e.g., liver, lung, lymph nodes, colon, stomach, pancreas, bile duct, small bowel and/or esophagus. Biological samples may also include sections of tissues such as biopsy and autopsy samples, frozen sections taken for histologic purposes, blood, plasma, serum, sputum, stool, tears, mucus, bile, saliva, lymph, hair, skin, etc. Biological samples also include explants and primary and/or transformed cell cultures derived from patient tissues. A biological sample is typically obtained from a eukaryotic organism, e.g., a primate such as a chimpanzee or human; cow; horse; goat; sheep; dog; cat; a rodent, e.g., guinea pig, rat or mouse; rabbit; bird; reptile; or fish. A sample is usually provided by removing a sample of cells from an animal, but can also be accomplished by providing previously isolated cells (e.g., isolated by another person, at another time and/or for another purpose), or by performing the methods of the invention in vivo. Archival tissues, having treatment or outcome history, can be used.

In some embodiments, methods are provided for detecting a cancer cell by detecting expression in the cell of a transcript (e.g., a FZD 7, FZD 8, Wnt3 and/or Wnt11 transcript) that is differentially expressed in a cancer cell. Any of a variety of known methods can be used for detection including but not limited to, detection of a transcript by hybridization of mRNA with an appropriate hybridization probe; detection of a transcript by a polymerase chain reaction using specific oligonucleotide primers; and in situ hybridization using an appropriate hybridization probe. The methods can be used to detect and/or measure mRNA levels of a gene that is differentially expressed in a cancer cell. In some embodiments, the methods comprise: a) contacting a sample with a polynucleotide that corresponds to a differentially expressed gene described herein under conditions that allow hybridization; and b) detecting hybridization, if any.

Detection of differential hybridization, when compared to a suitable control, is an indication of the presence in the sample of a polynucleotide that is differentially expressed in a cancer cell. Appropriate controls include, for example, a sample that is not a cancer cell, a sample that is known not to contain a polynucleotide that is differentially expressed in a cancer cell, and use of a labeled polynucleotide of the same "sense" as the polynucleotide that is differentially expressed in the cancer cell. Conditions that allow hybridization are known in the art and have been described in more detail above. Detection can also be accomplished by any known method, including, but not limited to, in situ hybridization, PCR (polymerase chain reaction) and/or RT-PCR (reverse transcription-PCR), or combinations of known techniques. A variety of labels and labeling methods for polynucleotides are known in the art and can be used in the assay methods of the invention. Specificity of hybridization can be determined by comparison to appropriate controls.

Polynucleotides generally comprising at least 10 nt, at least 12 nt or at least 15 contiguous nucleotides of a polynucleotide described herein, such as those having the sequence as depicted herein, can be used for a variety of purposes, such as probes or PCR primers for detection and/or measurement of transcription levels of a polynucleotide that is differentially expressed in a cancer cell. As will be appreciated by the skilled artisan, the probe can be detectably labeled and contacted with, for example, an array comprising immobilized polynucleotides obtained from a test sample (e.g., mRNA). Alternatively, the probe can be immobilized on an array and the test sample detectably labeled. The use of these and other variations of the methods of the invention are well within the skill in the art and are within the scope of the invention.

Nucleotide probes can be used to detect expression of a gene corresponding to the provided polynucleotide. In Northern blots, mRNA is separated electrophoretically and contacted with a probe. A probe is detected as hybridizing to an mRNA species of a particular size. The amount of hybridization can be quantified to determine relative amounts of expression. Probes can be used for in situ hybridization to cells to detect expression. Probes can also be used in vivo for diagnostic detection of hybridizing sequences. Probes can be labeled with a radioactive isotope or other types of detectable labels, e.g., chromophores, fluorophores and/or enzymes. Other examples of nucleotide hybridization assays are described in WO92/02526 and U.S. Pat. No. 5,124,246.

PCR is another means for detecting small amounts of target nucleic acids (see, e.g., Mullis et al., Meth. Enzymol. (1987) 155:335; U.S. Pat. No. 4,683,195; and U.S. Pat. No. 4,683, 202). Two primer oligonucleotides that hybridize with the target nucleic acids can be used to prime the reaction. The primers can be composed of sequence within or 3' and 5' to the polynucleotides described herein. After amplification of the target by standard PCR methods, the amplified target nucleic acids can be detected by methods known in the art, e.g., Southern blot. mRNA or cDNA can also be detected by traditional blotting techniques (e.g., Southern blot, Northern blot, etc.) described in Sambrook et al., "Molecular Cloning: A Laboratory Manual" (New York, Cold Spring Harbor Laboratory, 1989) (e.g., without PCR amplification). In general, mRNA or cDNA generated from mRNA using a polymerase enzyme can be purified and separated using gel electrophoresis, and transferred to a solid support, such as nitrocellulose. The solid support can be exposed to a labeled probe and washed to remove any unhybridized probe. Duplexes containing the labeled probe can then be detected.

Methods using PCR amplification can be performed on the DNA from one or more cells. The use of the polymerase chain reaction is described in Saiki et al. (1985) Science 239:487, and a review of techniques may be found in Sambrook et al., "Molecular Cloning: A Laboratory Manual" (New York, Cold Spring Harbor Laboratory, 1989; pp. 14.2-14.33). A detectable label may be included in the amplification reaction. Suitable detectable labels include fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4,4',5',7,7'-hexachlorofluorescein (HEX), 5-carboxyfluorescein (5-FAM) or N,N,N',N'-tetramethyl-6-carboxyrho-damine (TAMRA)), radioactive labels, (e.g., $^{32}$P, $^{35}$S, $^{3}$H, etc.), and the like. The label may be a two stage system, where the polynucleotide is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In one embodiment, expression level is assessed by using real time PCR. RNA is isolated from a sample of interest. PCR primers are designed to amplify the specific gene of interest. PCR product accumulation is measured using a dual-labeled fluorogenic oligonucleotide probe. The probe is labeled with two different fluorescent dyes, the 5' terminus reporter dye and the 3' terminus quenching dye. The oligonucleotide probe is selected to be homologous to an internal target sequence present in the PCR amplicon. When the probe is intact, energy transfer occurs between the two fluorophores, and the fluorescent emission is quenched. During the extension phase of PCR, the probe is cleaved by 5' nuclease activity of Taq polymerase. Therefore, the reporter is no longer in proximity to the quencher, and the increase in emission intensity is measured. An exemplary method for detecting FZD expression using real time PCR is provided in the Examples section, below. The primers can also be used in other methods, for example RT-PCR. This assay provides a quantitative measure of nucleic acid.

In other embodiments, methods are provided for detecting a cancer cell by detecting expression of a protein (e.g., a FZD 7, FZD 8, Wnt3 and/or Wnt11 protein) that is differentially expressed by the cell. Any of a variety of known methods can be used for detection, including but not limited to methods that employ binding compounds, e.g., antibodies or antigen binding fragments thereof, e.g., as is useful in ELISA and/or Western blotting methods. Such antibodies can be polyclonal or monoclonal and can be labeled with a detectable marker (e.g., fluorophore, chromophore or isotope, etc). Where appropriate, the compound can be attached to a solid support such as a bead, plate, filter, resin, etc. Determination of formation of the compound/target complex can be effected by contacting the complex with a further compound (e.g., a secondary antibody) that specifically binds the first compound (or complex). Like the first compound, the further compound can be attached to a solid support and/or can be labeled with a detectable marker.

The materials needed to perform the detection methods described herein can be provided as part of a kit. Thus, the invention further provides kits for detecting the presence and/or a level of a polynucleotide that is differentially expressed in a cancer cell (e.g., by detection of an mRNA encoded by the differentially expressed gene of interest), and/or a polypeptide encoded thereby, in a biological sample. Procedures using these kits can be performed by clinical laboratories, experimental laboratories, medical practitioners or private individuals. The kits of the invention for detecting a polypeptide encoded by a polynucleotide that is differentially expressed in a cancer cell may comprise a moiety, such as an antibody, that specifically binds the polypeptide. The kits of the invention used for detecting a polynucleotide that is differentially expressed in a cancer cell may comprise a moiety that specifically hybridizes to such a polynucleotide. The kit may optionally provide additional components that are useful in the procedure including, e.g., buffers, developing reagents, labels, reacting surfaces, means for detection, control samples, standards, instructions, and interpretive information.

The present invention further relates to methods of detecting/diagnosing a neoplastic or preneoplastic condition in a mammal (for example, a human). "Diagnosis" as used herein generally includes determination of a patient's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

One exemplary detection/diagnostic method includes: (a) obtaining from a mammal (e.g., a human) a biological sample (e.g., liver tissue), (b) detecting in the sample the presence of a FZD 7, FZD 8, Wnt 3 and/or Wnt 11 gene product (e.g., protein or mRNA), and (c) comparing the amount of FZD 7, FZD 8, Wnt 3 and/or Wnt 11 gene product present with that in a control sample. In accordance with this method, the presence in the sample of elevated levels of FZD 7 and/or Wnt 3 gene product and/or reduced levels of FZD 8 and/or Wnt 11 gene product indicates that the subject has a neoplastic or preneoplastic condition, e.g., liver cancer or a risk for developing liver cancer.

The identification of elevated levels of FZD 7 and/or Wnt 3 protein and/or reduced levels of FZD 8 and/or Wnt 11 protein in accordance with the present invention makes possible the identification of patients that are likely to benefit from specialized therapy. For example, a biological sample from a post primary therapy subject (e.g., subject having undergone surgery) can be screened for the presence of elevated levels of FZD 7 and/or Wnt 3 and/or reduced levels of FZD 8 and/or Wnt 11 protein, such levels being indicative of residual tumor tissue. Similarly, tissue surrounding the cut site of a surgically removed tumor (e.g., peritumorous tissue) can be examined (e.g., by immunofluorescence), the presence of elevated levels of FZD 7 and/or Wnt 3 and/or reduced levels of FZD 8 and/or Wnt 11 (relative to the surrounding tissue) being indicative of potential development of disease in this tissue or incomplete removal of the tumor. The ability to identify such patients makes it possible to tailor therapy to the needs of the particular patient. Subjects undergoing non-surgical therapy, e.g., chemotherapy or radiation therapy, can also be monitored, the presence in samples from such subjects of elevated levels of FZD 7 and/or Wnt 3 and/or reduced levels of FZD 8 and/or Wnt 11 being indicative of the need for continued treatment. Skilled practitioners will also appreciate that staging of cancer (e.g., liver cancer) for purposes of optimizing treatment regimens can be performed using the methods described herein.

III. Methods for Identifying Compounds Capable of Treating Cancer

The invention provides methods for screening test compounds for an ability to treat cancer, e.g., liver cancer. A "test compound" as described herein is any compound that can be screened using the methods described herein. For example, a test compound can be, e.g., a small organic or inorganic molecule (M.W. less than 1,000 Da). Alternatively or in addition, the test compound can be a polypeptide (e.g., a polypeptide having a random or predetermined amino acid sequence or a naturally-occurring or synthetic polypeptide) or a nucleic acid, such as a DNA or RNA molecule. A test compound can be naturally occurring (e.g., an herb or a natural product), or synthetic, or can include both natural and synthetic components. A test compound can have a formula weight of less than about 10,000 grams per mole, less than 5,000 grams per mole, less than 1,000 grams per mole, or less than about 500 grams per mole. The test compound can be, for example, any organic or inorganic compound (e.g., heteroorganic or organometallic compound), an amino acid, amino acid analog, polypeptide, peptidomimetic (e.g., peptoid), oligopeptide (e.g., from about 5 to about 25 amino acids in length, preferably from about 10 to 20 or 12 to 18 amino acids in length, preferably 12, 15, or 18 amino acids in length), nucleotide, nucleotide analog, polynucleotide, polynucleotide analog, ribonucleic acid, deoxyribonucleic acid, antisense oligonucleotide, ribozyme, saccharide, lipid (e.g., a sphingolipid), and/or a fatty acid, or any combination thereof.

The terms "antagonist" or "inhibitor" of Wnt/FZD signaling (e.g., Wnt/FZD 7 signaling) refer to compounds that, e.g., bind to Wnt proteins (e.g., Wnt 3, 8, and/or 11) and/or FZD receptors (e.g., FZD 7) and/or partially or totally block or inhibit Wnt/FZD signaling (e.g., Wnt/FZD 7 signaling) as measured in known assays for Wnt/FZD signaling (e.g., measurement of β-catenin levels, oncogene expression controlled by Tcf and Lef transcription factors or other downstream Wnt/Frizzled regulated gene products). Inhibitors include, e.g., antibodies directed against Wnt or FZD proteins (one example of an anti-Wnt3 antibody is described in the Examples section, below), modified versions of Wnt or FZD proteins, naturally occurring and synthetic ligands, antagonists, agonists, antibodies, small chemical molecules, and the like. Assays for detecting inhibitors or antagonists are described in more detail below.

Libraries of Test Compounds

In certain embodiments, screens of the present invention utilize libraries of test compounds. A "library" is a collection of compounds (e.g., as a mixture or as physically separated individual compounds) synthesized from various combinations of one or more starting components. At least some of the compounds must differ from at least some of the other compounds in the library. A library can include, e.g., 5, 10, 50, 100, 1000, or even 10,000, 50,000, or 100,000, or more different compounds (i.e., not simply multiple copies of the same compounds, although some compounds in the library may be duplicated or represented more than once). Each of the different compounds will be present in an amount such that its presence can be determined by some means, e.g., can be isolated, analyzed, and/or detected with a receptor or suitable probe. The actual quantity of each different compound needed so that its presence can be determined will vary due to the actual procedures used and may change as the technologies for isolation, detection, and analysis advance. When the compounds are present in a mixture in substantially equimolar amounts, for example, an amount of 100 picomoles of each compound can often be detected. Libraries can include both libraries of individual compounds (e.g., present substantially as a single type of compound-per-well, made via parallel synthesis or the pool and split pool method) and mixtures containing substantially equimolar amounts of each desired compound (i.e., wherein no single compound dominates). Either library format can allow identification of an active compound discovered in an assay.

Test compounds can be screened individually or in parallel. An example of parallel screening is a high throughput drug screen of large libraries of chemicals. Such libraries of candidate compounds can be generated or purchased, e.g., from Chembridge Corp., San Diego, Calif. Alternatively, prior experimentation and anecdotal evidence can suggest a class or category of compounds of enhanced potential. A library can be designed and synthesized to cover such a class of chemicals.

The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy can result in a library of peptides, e.g., modulators, which can be used to prepare a library of test compounds of the invention. In another illustrative synthesis, a "diversomer library" is created by the method of Hobbs DeWitt et al (*Proc. Natl. Acad. Sci. U.S.A.* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J. Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening libraries of test compounds are described above.

Screening Methods

The invention provides methods for identifying compounds capable of treating cancer, e.g., liver cancer. Although applicants do not intend to be bound by any particular theory as to the biological mechanism involved, such compounds are thought to modulate specifically (1) Wnt/FZD signaling (e.g., by binding to FZD 7, Wnt 3, Wnt 8b and/or Wnt 11 polypeptides and/or reducing (e.g., preventing) Wnt/FZD-mediated transcription) and/or (2) expression of FZD 7, FZD 8, Wnt3 and/or Wnt11.

In certain aspects of the present invention, screening for such compounds is accomplished by (i) identifying from a group of test compounds those that bind to a FZD 7, Wnt 3, Wnt 8b and/or Wnt 11 polypeptide, modulate (i.e., increase or decrease) an interaction between FZD 7 and its ligand (e.g., Wnt 3, Wnt 8b and/or Wnt 11) and/or modulate (i.e., increase or decrease) transcription and/or translation of FZD 7, FZD 8, Wnt3, Wnt 8b and/or Wnt11; and, optionally, (ii) further testing such compounds for their ability to modulate Wnt/FZD signaling, reduce cancer cell motility, reduce β-catenin accumulation in cancer cells and/or to treat cancer in vitro or in vivo. Test compounds that bind to FZD 7, Wnt 3, Wnt 8b and/or Wnt 11 polypeptides, modulate an interaction between FZD 7 and its ligand (e.g., Wnt 3, Wnt 8b and/or Wnt 11), or modulate transcription and/or translation of FZD 7, FZD 8, Wnt3, Wnt 8b, and/or Wnt11, are referred to herein as "candidate anti-cancer agents." Candidate anti-cancer agents further tested and found to be capable of modulating in vitro or in vivo Wnt/FZD signaling, reducing cancer cell motility, reduce β-catenin accumulation in cancer cells and/or treating cancer are considered "anti-cancer agents." In the screening methods of the present invention, candidate anti-cancer agents can be, but do not necessarily have to be, tested to determine whether they are anti-cancer agents. Assays of the present invention may be carried out in biological samples, whole cell preparations and/or ex vivo cell-free systems.

In one aspect, the invention includes methods for screening test compounds to identify compounds that bind to FZD polypeptides, e.g., FZD 7 polypeptides, and/or to Wnt polypeptides, e.g., Wnt 3, 8b and/or 11 polypeptides. Binding of a test compound to a FZD or Wnt polypeptide can be detected, for example, in vitro by reversibly or irreversibly immobilizing the test compound(s) or the Wnt or FZD polypeptide on a substrate, e.g., the surface of a well of a 96-well polystyrene microtitre plate. Methods for immobilizing polypeptides and other small molecules are well known in the art. For example, microtitre plates can be coated with a FZD or Wnt polypeptide by adding the polypeptide in a solution (typically, at a concentration of 0.05 to 1 mg/ml in a volume of 1-100 μl) to each well, and incubating the plates at room temperature to 37° C. for a given amount of time, e.g., for 0.1 to 36 hours. Polypeptides not bound to the plate can be removed by shaking excess solution from the plate, and then washing the plate (once or repeatedly) with water or a buffer. Typically, the polypeptide is in water or a buffer. The plate can then be washed with a buffer that lacks the bound polypeptide. To block the free protein-binding sites on the plates, plates can be blocked with a protein that is unrelated to the bound polypeptide. For example, 300 μl of bovine serum albuminutes (BSA) at a concentration of 2 mg/ml in Tris-HCl can be used. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a particle, e.g., beaded agarose or beaded sepharose, can be used as the substrate. Test compounds can then be added to the coated plate and allowed to bind to the FZD or Wnt polypeptide (e.g., at 37° C. for 0.5-12 hours). The plate can then be rinsed as described above. Skilled practitioners will appreciate that many variations of this method are possible. For example, the method can include coating a substrate with a test compound and adding Wnt or FZD polypeptides to the substrate-bound compound.

Binding of FZD or Wnt to a second compound, e.g., a test compound described above or to a binding partner (e.g., FZD 7 to Wnt 3, 8b and/or 11; discussed in further detail below), can be detected by any of a variety of art-known methods. For example, an antibody that specifically binds to a FZD or Wnt polypeptide (i.e., an anti-FZD antibody or an anti-Wnt antibody, e.g., a polyclonal anti-Wnt3 antibody described in the Examples section) can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds to the Fc portion of the anti-FZD or anti-Wnt antibody). In an alternative detection method, the FZD or Wnt polypeptide is labeled (e.g., with a radioisotope, fluorophore, chromophore, or the like), and the label is detected. In still another method, a FZD or Wnt polypeptide is produced as a fusion protein with a protein that can be detected optically, e.g., green fluorescent protein (which can be detected under UV light). In an alternative method, the polypeptide is produced as a fusion protein with an enzyme having a detectable enzymatic activity, such as horseradish peroxidase, alkaline phosphatase, β-galactosidase, or glucose oxidase. Genes encoding all of these enzymes have been cloned and are available for use by skilled practitioners. If desired, the fusion protein can include an antigen or epitope that can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various methods for identifying polypeptides (e.g., test polypeptides) that bind to FZD or Wnt polypeptides, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., Proc. Natl. Acad. Sci. USA, 93:10315-10320, 1996; and White, *Proc. Natl. Acad. Sci. USA*, 93:10001-10003, 1996). Generally, two-hybrid methods involve reconstitution of two separable domains of a transcription factor. One fusion protein includes the FZD or Wnt polypeptide fused to either a transactivator domain or DNA binding domain of a transcription factor (e.g., of Ga14). The other fusion protein contains a test polypeptide or a binding partner for the polypeptide included in the first fusion protein, fused to either the DNA binding domain or a transactivator domain of a transcription factor. Binding of the FZD or Wnt polypeptide to the test polypeptide or binding partner reconstitutes the transcription factor. Reconstitution of the transcription factor can be detected by detecting expression of a gene (i.e., a reporter gene) that is operably linked to a DNA sequence that is bound by the DNA binding domain of the transcription factor Kits for practicing various two-hybrid methods are commercially available (e.g., from Clontech; Palo Alto, Calif.).

In another aspect, the invention includes methods for screening test compounds to identify a compound that modulates a protein-protein interaction between FZD and Wnt polypeptides. A method useful for high throughput screening of compounds capable of modulating protein-protein interactions between transcriptional regulators is described in Lepourcelet et al., Cancer Cell 5: 91-102 (2004), which is incorporated herein by reference in its entirety. Typically, a first compound is provided. The first compound is a FZD (e.g., FZD 7) or Wnt (e.g., Wnt 3, 8b, or 11) polypeptide or biologically active fragment thereof. A second compound is provided that is different from the first compound and is labeled. The second compound is a FZD (e.g., FZD 7) or Wnt (e.g., Wnt 3, 8b, or 11) polypeptide or biologically active fragment thereof. A test compound is provided. The first compound, second compound and test compound are contacted with each other. The amount of label bound to the first compound is then determined. A change in protein-protein interaction between the first compound and the second compound as assessed by label bound is indicative of the usefulness of the test compound in modulating a protein-protein interaction between the FZD and Wnt polypeptide.

In certain embodiments, the first compound provided is attached to a solid support. Solid supports include, e.g., resins (e.g., agarose and beads) and multiwell plates. In certain embodiments, the method includes a washing step after the contacting step, so as to separate bound and unbound label.

In certain embodiments, a plurality of test compounds is contacted with the first compound and second compound. The different test compounds can be contacted with the other compounds in groups or separately. In certain embodiments, each of the test compounds is contacted with both the first compound and the second compound in an individual well. For example, the method can screen libraries of test compounds. Libraries of test compounds are discussed in detail above. Libraries can include, e.g., natural products, organic chemicals, peptides, and/or modified peptides, including, e.g., D-amino acids, unconventional amino acids, and N-substituted amino acids. Typically, the libraries are in a form compatible with screening in multiwell plates, e.g., 96-well plates. The assay is particularly useful for automated execution in a multiwell format in which many of the steps are controlled by computer and carried out by robotic equipment. The libraries can also be used in other formats, e.g., synthetic chemical libraries affixed to a solid support and available for release into microdroplets.

In certain embodiments, the first compound is a FZD 7 polypeptide or fragment thereof and the second compound is a Wnt polypeptide, such as Wnt 3, 8b, or 11, or fragment thereof. In other embodiments, the first compound is a Wnt polypeptide, such as Wnt 3, 8b, or 11 polypeptide or fragment thereof, and the second compound is a FZD 7 polypeptide or fragment thereof. The solid support to which the first compound is attached can be, e.g., sepharose beads, SPA beads (microspheres that incorporate a scintillant) or a multiwell plate. SPA beads can be used when the assay is performed without a washing step, e.g., in a scintillation proximity assay. Sepharose beads can be used when the assay is performed with a washing step. The second compound can be labeled with any label that will allow its detection, e.g., a radiolabel, a fluorescent agent, biotin, a peptide tag, or an enzyme fragment. The second compound can also be radiolabeled, e.g., with $^{125}I$ or $^{3}H$.

In certain embodiments, the enzymatic activity of an enzyme chemically conjugated to, or expressed as a fusion protein with, the first or second compound, is used to detect bound protein. A binding assay in which a standard immunological method is used to detect bound protein is also included. In certain other embodiments, the interaction of Wnt and FZD polypeptides or fragments thereof is detected by fluorescence resonance energy transfer (FRET) between a donor fluorophore covalently linked to a FZD or Wnt polypeptide (e.g., a fluorescent group chemically conjugated to FZD or Wnt, or a variant of green fluorescent protein (GFP) expressed as an FZD or Wnt-GFP chimeric protein) and an acceptor fluorophore covalently linked to a substrate protein, where there is suitable overlap of the donor emission spectrum and the acceptor excitation spectrum to give efficient nonradiative energy transfer when the fluorophores are brought into close proximity through the protein-protein interaction of FZD and Wnt polypeptides.

In other embodiments, the protein-protein interaction is detected by reconstituting domains of an enzyme, e.g., beta-galactosidase (see Rossi et al, Proc. Natl. Acad. Sci. USA 94:8405-8410 (1997)).

In still other embodiments, the protein-protein interaction is assessed by fluorescence ratio imaging (Bacskai et al, Science 260:222-226 (1993)) of suitable chimeric constructs of FZD and Wnt polypeptides in cells, or by variants of the two-hybrid assay (Fearon et al, Proc Natl Acad Sci USA 89:7958-7962 (1992); Takacs et al, Proc Natl Acad Sci USA 90:10375-10379 (1993); Vidal et al, Proc Natl Acad Sci USA 93:10321-10326 (1996)) employing suitable constructs of FZD and Wnt polypeptides and tailored for a high throughput assay to detect compounds that inhibit the FZD/Wnt interaction. These embodiments have the advantage that the cell permeability of the test compounds is assured.

For example, in one assay, a FZD or Wnt polypeptide or fragment thereof is adsorbed to ELISA plates. The FZD or Wnt polypeptides are then exposed to test compounds, followed by a glutathione-S-transferase (GST)-binding partner fusion protein, e.g., a GST-FZD or -Wnt polypeptide fusion protein. Bound protein is detected with goat anti-GST antibody, alkaline phosphatase (AP)-coupled anti-goat IgG, and AP substrate. Compounds that interfere with protein-protein interactions yield reduced AP signals in the ELISA plates.

In still another aspect, the invention provides methods of identifying test compounds that modulate (e.g., increase or decrease) expression of a FZD and/or Wnt polypeptide. The method includes contacting a FZD and/or Wnt nucleic acid with a test compound and then measuring expression of the encoded FZD and/or Wnt polypeptide. In a related aspect, the invention features a method of identifying compounds that modulate (e.g., increase or decrease) the expression of FZD and/or Wnt polypeptides by measuring expression of a FZD polypeptide in the presence of the test compound or after the addition of the test compound in: (a) a cell line into which has been incorporated a recombinant construct including the FZD and/or Wnt nucleic acid sequence or fragment or an allelic variation thereof; or (b) a cell population or cell line that naturally selectively expresses FZD and/or Wnt, and then measuring the expression of the FZD and/or Wnt protein.

Since the FZD and Wnt nucleic acids described herein have been identified, they can be cloned into various host cells (e.g., mammalian cells, insect cells, bacteria or fungi) for carrying out such assays in whole cells.

In certain embodiments, an isolated nucleic acid molecule encoding a FZD and/or Wnt polypeptide is used to identify a compound that modulates (e.g., increases or decreases) the expression of FZD and/or Wnt in vivo (e.g., in a FZD and/or Wnt-producing cell). In such embodiments, cells that express a FZD (e.g., FZD 7 and/or 8) and/or Wnt (e.g., Wnt3, Wnt8b or Wnt11) are cultured, exposed to a test compound (or a mixture of test compounds), and the level of FZD and/or Wnt expression is compared with the level of FZD and/or Wnt expression or activity in cells that are otherwise identical but that have not been exposed to the test compound(s). Standard quantitative assays of gene expression can be used.

Expression of FZD and Wnt can be measured using art-known methods, for example, by Northern blot PCR analysis or RNAse protection analyses using a nucleic acid molecule of the invention as a probe. Other examples include enzyme-linked immunosorbent assay (ELISA), radioimmunoassay (RIA) and fluorescent activated cell sorting (FACS). The level of expression in the presence of the test molecule, compared with the level of expression in its absence, will indicate whether or not the test compound modulates the expression of a FZD and/or Wnt polypeptide.

In still another aspect, the invention provides methods of screening test compounds utilizing cell systems that are sensitive to perturbation of one or several transcriptional/translational components.

In certain embodiments, the methods include identifying candidate compounds that interfere with steps in FZD and/or Wnt translational accuracy, such as maintaining a proper reading frame during translation and terminating translation at a stop codon. This method involves constructing cells in which a detectable reporter polypeptide can only be produced if the normal process of staying in one reading frame or of terminating translation at a stop codon has been disrupted. This method further involves contacting the cell with a test compound to examine whether it increases or decreases the production of the reporter polypeptide.

In other embodiments, the cell system is a cell-free extract and the method involves measuring transcription or translation in vitro. Conditions are selected so that transcription or translation of the reporter is increased or decreased by the addition of a transcription modifier or a translation modifier to the cell extract.

One method for identifying candidate compounds relies upon a transcription-responsive gene product. This method involves constructing a cell in which the production of a reporter molecule changes (i.e., increases or decreases) under conditions in which cell transcription of a FZD and/or Wnt nucleic acid changes (i.e., increases or decreases). Specifically, the reporter molecule is encoded by a nucleic acid transcriptionally linked to a sequence constructed and arranged to cause a relative change in the production of the reporter molecule when transcription of a FZD and/or Wnt nucleic acid changes. A gene sequence encoding the reporter may, for example, be fused to part or all of the gene encoding the transcription-responsive gene product and/or to part or all of the genetic elements that control the production of the gene product. Alternatively, the transcription-responsive gene product may stimulate transcription of the gene encoding the reporter, either directly or indirectly. The method further involves contacting the cell with a test compound, and determining whether the test compound increases or decreases the production of the reporter molecule in the cell.

Alternatively, the method for identifying candidate compounds can rely upon a translation-responsive gene product. This method involves constructing a cell in which cell translation of a FZD and/or Wnt nucleic acid changes (i.e., increases or decreases). Specifically, the reporter molecule is encoded by nucleic acid translationally linked to a sequence constructed and arranged to cause a relative increase or decrease in the production of the reporter molecule when transcription of a FZD and/or Wnt nucleic acid changes. A gene sequence encoding the reporter may, for example, be fused to part or all of the gene encoding the translation-responsive gene product and/or to part or all of the genetic elements that control the production of the gene product. Alternatively, the translation-responsive gene product may stimulate translation of the gene encoding the reporter, either directly or indirectly. The method further involves contacting the cell with a test compound, and determining whether the test compound increases or decreases the production of the first reporter molecule in the cell.

For these and any method described herein, a wide variety of reporters may be used, with typical reporters providing conveniently detectable signals (e.g., by spectroscopy). By way of example, a reporter gene may encode an enzyme that catalyses a reaction that alters light absorption properties.

Examples of reporter molecules include but are not limited to β-galactosidase, invertase, green fluorescent protein, luciferase, chloramphenicol acetyltransferase, beta-glucuronidase, exo-glucanase, glucoamylase and radiolabeled reporters. For example, the production of the reporter molecule can be measured by the enzymatic activity of the reporter gene product, such as β-galactosidase.

Any of the methods described herein can be used for high throughput screening of numerous test compounds to identify candidate anti-cancer agents. By high-throughput screening is meant that the method can be used to screen a large number of candidate compounds relatively easily and quickly.

Having identified a test compound as a candidate anti-cancer agent, the compound can be further tested in vivo or in vitro using techniques known in the art to confirm whether it is an anti-cancer agent, i.e., to determine whether it can modulate Wnt/FZD signaling; cancer cell motility; and/or FZD and/or Wnt expression in vitro (e.g., using isolated cells or cell-free systems) or in vivo (e.g., using an animal, e.g., rodent, model system) if desired.

In vitro testing of a candidate compound can be accomplished by means known to those in the art, such as assays involving the use of cells, e.g., wild type, cancerous and/or transgenic liver cells. Exemplary assays for monitoring Wnt/FZD signaling, FZD and Wnt expression and cancer cell motility, as well as useful cells that can be used in such assays, are described in the Examples section, below.

Alternatively or in addition, in vivo testing of candidate compounds can be performed by means known to those in the art. For example, the candidate compound(s) can be administered to a mammal, such as a rodent (e.g., mouse) or rabbit. Such animal model systems are art-accepted for testing potential pharmaceutical agents to determine their therapeutic efficacy in patients, e.g., human patients. Animals that are particularly useful for in vivo testing are wild type animals or non-wild type animals (e.g., mice) that over-produce FZD and/or Wnt polypeptides, e.g., animals that overexpress a FZD or Wnt transgene (e.g., a FZD 7 or Wnt3 transgene) and/or that display reduced production of FZD 8 and/or Wnt11 polypeptides. Other animals that are useful for in vivo testing are animals bred to develop liver cancer. Certain particularly useful transgenic mice that develop liver cancer are described in the Examples section and are included in the present invention.

In a typical in vivo assay, an animal (e.g., a wild type or transgenic mouse) is administered, by any route deemed appropriate (e.g., by injection), a dose of a candidate compound. Conventional methods and criteria can then be used to monitor animals for the desired activity. If needed, the results obtained in the presence of the candidate compound can be compared with results in control animals that are not treated with the test compound.

Medicinal Chemistry

Once a compound (or agent) of interest has been identified, standard principles of medicinal chemistry can be used to produce derivatives of the compound for further rounds of testing. Derivatives can be screened for improved pharmacological properties, for example, efficacy, pharmaco-kinetics, stability, solubility, and clearance. The moieties responsible for a compound's activity in the assays described above can be delineated by examination of structure-activity relationships (SAR) as is commonly practiced in the art. A person of ordinary skill in pharmaceutical chemistry could modify moieties on a candidate compound or agent and measure the effects of the modification on the efficacy of the compound or agent to thereby produce derivatives with increased potency. For an example, see Nagarajan et al. (1988) *J. Antibiot.* 41: 1430-8. Furthermore, if the biochemical target of the compound (or agent) is known or determined, the structure of the target and the compound can inform the design and optimization of derivatives. Molecular modeling software is commercially available (e.g., Molecular Simulations, Inc.) for this purpose.

IV. Antibodies

The invention features purified or isolated antibodies that bind, e.g., specifically bind, to a FZD and/or Wnt polypeptide, i.e., anti-FZD and anti-Wnt antibodies. An antibody "specifically binds" to a particular antigen, e.g., a FZD 7 and/or 8 polypeptide, when it binds to that antigen, but recognizes and binds to a lesser extent (e.g., does not recognize and bind) to other molecules in a sample. Antibodies of the invention include monoclonal antibodies, polyclonal antibodies, humanized or chimeric antibodies, single chain antibodies, Fab fragments, F(ab')$_2$ fragments, and molecules produced using a Fab expression library.

An example of a type of antibody included in the present invention is the polyclonal anti-Wnt3 antibody described in the Examples section, below. Methods for producing polyclonal antibodies are well known to those of skill in the art.

As used herein, the term "antibody" refers to a protein comprising at least one, e.g., two, heavy (H) chain variable regions (abbreviated herein as VH), and at least one, e.g., two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) *J. Mol. Biol.* 196:901-917). Each VH and VL is composed of three CDR's and four FRs, arranged from amino-terminus to carboxy-terminus in the following order: FR1, CDR1, FR2, CDR2, FR3, CDR3, FR4.

An anti-FZD or -Wnt antibody can further include a heavy and light chain constant region, to thereby form a heavy and light immunoglobulin chain, respectively. The antibody can be a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2, and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

A "FZD binding fragment" and "Wnt binding fragment" of an antibody refers to one or more fragments of a full-length antibody that retain the ability to specifically bind to FZD or Wnt polypeptides, respectively, or to portions thereof. Examples of polypeptide binding fragments of an antibody include, but are not limited to: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are encoded by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al (1988) *Proc. Natl. Acad. Sci. USA* 85:5879-5883). Such single chain antibodies are also encompassed within the terms "FZD binding fragment" and "Wnt binding fragment" of an antibody. These antibody fragments can be obtained using conventional techniques known to those with skill in the art.

To produce antibodies, polypeptides (or antigenic fragments (e.g., fragments of a polypeptide that appear likely to be antigenic by criteria such as high frequency of charged residues) or analogs of such polypeptides), e.g., those produced by recombinant or peptide synthetic techniques (see, e.g., *Solid Phase Peptide Synthesis*, supra; Ausubel et al., supra), can be used. In general, the polypeptides can be coupled to a carrier protein, such as KLH, as described in Ausubel et al., supra, mixed with an adjuvant, and injected into a host mammal. A "carrier" is a substance that confers stability on, and/or aids or enhances the transport or immunogenicity of, an associated molecule. For example, FZD or Wnt proteins, or fragments thereof, can be generated using standard techniques of PCR, and can be cloned into a pGEX expression vector (Ausubel et al., supra). Fusion proteins can be expressed in *E. coli* and purified using a glutathione agarose affinity matrix as described in Ausubel et al., supra.

Typically, various host animals are injected with FZD and/ or Wnt polypeptides. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Such procedures result in the production of polyclonal antibodies, i.e., heterogeneous populations of antibody molecules derived from the sera of the immunized animals. Antibodies can be purified from blood obtained from the host animal, for example, by affinity chromatography methods in which FZD and/or Wnt polypeptide antigens are immobilized on a resin.

The present invention also includes anti-FZD and anti-Wnt monoclonal antibodies. Monoclonal antibodies (mAbs), which are homogeneous populations of antibodies specific for a particular antigen, can be prepared using FZD or Wnt polypeptides and standard hybridoma technology (see, e.g., Kohler et al., *Nature*, 256:495, 1975; Kohler et al., *Eur. J. Immunol*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

Typically, monoclonal antibodies are produced using any technique that provides for the production of antibody molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77-96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies can be tested for recognition, e.g., specific recognition, of FZD or Wnt polypeptides in an immunoassay, such as a Western blot or immunoprecipitation analysis using standard techniques, e.g., as described in Ausubel et al., supra. Antibodies that specifically bind to FZD or Wnt polypeptides (e.g., FZD 7, FZD 8, Wnt 3, Wnt 8b and/or Wnt 11) are useful in the invention. For example, such antibodies can be used in an immunoassay to detect the polypeptide in a sample, e.g., a tissue sample, and/or to modulate FZD/Wnt signaling (e.g., to treat cancer, e.g., liver cancer).

Alternatively or in addition, a monoclonal antibody can be produced recombinantly, e.g., produced by phage display or by combinatorial methods as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J.* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 2:1373-1377; Hoogenboom et al. (1991) *Nuc Acid Res* 19:4133-4137; and Barbas et al. (1991) *PNAS* 88:7978-7982.

Anti-FZD and -Wnt antibodies can be fully human antibodies (e.g., an antibody made in a mouse which has been genetically engineered to produce an antibody from a human immunoglobulin sequence), or non-human antibodies, e.g., rodent (mouse or rat), rabbit, horse, cow, goat, primate (e.g., monkey), camel, donkey, pig, or bird antibodies.

An anti-FZD and anti-Wnt antibody can be one in which the variable region, or a portion thereof, e.g., the CDRs, is generated in a non-human organism, e.g., a rat or mouse. The anti-FZD and anti-Wnt antibody can also be, for example, chimeric, CDR-grafted, or humanized antibodies. The anti-FZD and anti-Wnt antibody can also be generated in a non-human organism, e.g., a rat or mouse, and then modified, e.g., in the variable framework or constant region, to decrease antigenicity in a human.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies specific for a FZD or Wnt polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies (or fragments thereof) that specifically bind to a FZD and/or Wnt polypeptide can be used, for example, to detect expression of FZD and/or Wnt in various tissues of a patient. For example, a FZD 7 and/or 8 polypeptide can be detected in conventional immunoassays of biological tissues or extracts. Examples of suitable assays include, without limitation, Western blotting, ELISAs, radioimmunoassays, and the like.

V. Pharmaceutical Compositions

Any pharmaceutically active compound, agent, nucleic acid, polypeptide, or antibody (all of which can be referred to herein as "active compounds"), can be incorporated into pharmaceutical compositions. Such compositions typically include the active compound and a pharmaceutically acceptable carrier. A "pharmaceutically acceptable carrier" can include solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition can be formulated to be compatible with its intended route of administration. Examples of routes of administration include enteral (e.g., oral or rectal) and parenteral, e.g., intravenous (e.g., into the portal vein of the liver), intradermal, subcutaneous, transdermal, transmucosal, and pulmonary administration. Administration may be directly into the liver, e.g., by injection or by topical administration during surgery. Solutions or suspensions used for injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol and sodium chloride. Prolonged absorption of the injectable compositions can be achieved by including an agent which delays absorption, e.g., aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories (e.g., with conventional suppository bases such as cocoa butter and other glycerides). For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It may be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds which exhibit high therapeutic indices are preferred. While compounds that exhibit toxic side effects may be used, care should be taken to design a delivery system that targets such compounds to the site of affected tissue, e.g., liver, in order to minimize potential damage to healthy cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The terms "effective amount" and "effective to treat," as used herein, refer to an amount or concentration of a compound described herein utilized for a period of time (including acute or chronic administration and periodic or continuous administration) that is effective within the context of its administration for causing an intended effect or physiological outcome. For compounds described herein, an effective amount, e.g., of a polypeptide (i.e., an effective dosage), ranges from about 0.001 to 500 mg/kg body weight, e.g. about 0.01 to 50 mg/kg body weight, e.g. about 0.1 to 20 mg/kg body weight. The polypeptide can be administered one time per week for between about 1 to 10 weeks, e.g. between 2 to 8 weeks, about 3 to 7 weeks, or for about 4, 5, or 6 weeks. The skilled artisan will appreciate that certain factors influence the dosage and timing required to effectively treat a patient, including but not limited to the type of patient to be treated, the severity of the disease or disorder, previous treatments, the general health and/or age of the patient, and other diseases present. Moreover, treatment of a patient with a therapeutically effective amount of a compound can include a single treatment or, preferably, can include a series of treatments.

With respect to antibodies, partially human antibodies and fully human antibodies have a longer half-life within the human body than other antibodies. Accordingly, lower dosages and less frequent administration are possible. Modifications such as lipidation can be used to stabilize antibodies and to enhance uptake and tissue penetration. A method for lipidation of antibodies is described by Cruikshank et al. ((1997) *J Acquired Immune Deficiency Syndromes and Human Retrovirology* 14:193).

If the compound is a small molecule, exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) to modulate expression or activity of a FZD or Wnt polypeptide or nucleic acid, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules (e.g., FZD 7, FZD 8, Wnt 3, Wnt8b and/or Wnt 11 DNA) can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system. Exemplary constructs that can potentially be used in gene therapy methods are described in the Examples section, below.

The pharmaceutical compositions can be included in a container, pack, or dispenser together with instructions for administration.

VI. Cancer and Treatments Therefor

The term "cancer" refers to animal cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, cancer of the small intestine, and cancer of the esophagus. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "hapatocellular carcinoma" (HCC) refers to cancer that arises from hepatocytes, the major cell type of the liver.

The term "patient" is used throughout the specification to describe an animal, human or non-human, rodent or non-rodent, to whom treatment according to the methods of the present invention is provided. Veterinary and human clinical applications are contemplated. The term "patient" includes, but is not limited to, birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs. The term "treat(ment)," is used herein to denote delaying the onset of, inhibiting, alleviating the effects of, or prolonging the life of a patient suffering from, a condition, e.g., cancer.

Cancers that may be treated using the methods and compositions of the present invention include, but are not limited to, cancers of the liver, stomach, colon, rectum, mouth/pharynx, esophagus, larynx, pancreas, lung, small bowel, and bile ducts, among others.

Individuals considered at risk for developing cancer may benefit particularly from the invention, primarily because prophylactic treatment can begin before there is any evidence of a tumor. Individuals "at risk" include, e.g., individuals exposed to carcinogens, e.g., by consumption, e.g., by inhalation and/or ingestion, at levels that have been shown statistically to promote cancer in susceptible individuals. Also included are individuals exposed to a virus, e.g., a hepatitis virus, e.g., hepatitis B virus (HBV). Also included are individuals at risk due to exposure to ultraviolet radiation, or their environment, occupation, and/or heredity, as well as those who show signs of a precancerous condition. Similarly, individuals in very early stages of cancer or development of metastases (i.e., only one or a few aberrant cells are present in the individual's body or at a particular site in an individual's tissue)) may benefit from such prophylactic treatment.

Skilled practitioners will appreciate that a patient can be diagnosed by a physician (or veterinarian, as appropriate for the patient being diagnosed) as suffering from or at risk for cancer using the methods described herein, optionally using additional methods, e.g., assessing a patient's medical history, performing other diagnostic tests and/or by employing imaging techniques.

One strategy for treating patients suffering from or at risk for cancer is to modulate Wnt/FZD signaling in the patient. The goal is to increase signaling where signaling is too low and to decrease signaling where signaling is too high. Modulation of Wnt/FZD signaling falls into two basic categories: decreasing (i.e., reducing, e.g., eliminating) Wnt/FZD signaling and increasing (i.e., supplementing or providing) Wnt/FZD signaling where there is insufficient or no activity. Whether Wnt/FZD signaling should be inhibited or increased depends upon the intended application. Wnt/FZD signaling can be modulated using the active compounds (e.g., anti-Wnt antibodies, siRNAs, candidate compounds and/or anti-cancer agents) described herein. Compounds that decrease Wnt/FZD signaling activity, e.g., by decreasing expression of FZD 7 and/or Wnt3 and/or interfering with an interaction between FZD 7 and its ligand (e.g., Wnt 3, 8b and/or 11) can be used, e.g., as treatments for cancer, e.g., liver cancer. Compounds that increase activity, e.g., by increasing expression of FZD 8 can also be used, e.g., as treatments for cancer, e.g., liver cancer.

Decreasing Wnt/FZD Signaling

Art-known methods for decreasing the expression of a particular protein in a patient can be used to decrease Wnt/FZD signaling. For example, an antisense nucleic acid effective to inhibit expression of an endogenous FZD or Wnt gene, e.g., FZD 7 or Wnt3 gene, can be utilized. As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA.

Antisense molecules are designed so as to interfere with transcription or translation of a target gene (e.g., a gene encoding FZD 7 or Wnt 3, 8b or 11) upon hybridization with the target gene or transcript. The antisense nucleic acid can include a nucleotide sequence complementary to an entire FZD or Wnt RNA or only a portion of the RNA. On one hand, the antisense nucleic acid needs to be long enough to hybridize effectively with FZD or Wnt RNA. Therefore, the minimum length is approximately 12 to 25 nucleotides. On the other hand, as length increases beyond about 150 nucleotides, effectiveness at inhibiting translation may increase only marginally, while difficulty in introducing the antisense nucleic acid into target cells may increase significantly. Accordingly, an appropriate length for the antisense nucleic acid may be from about 15 to about 150 nucleotides, e.g., 20, 25, 30, 35, 40, 45, 50, 60, 70, or 80 nucleotides. The antisense nucleic acid can be complementary to a coding region of FZD or Wnt mRNA or a 5' or 3' non-coding region of a FZD or Wnt mRNA, or both. One approach is to design the antisense nucleic acid to be complementary to a region on both sides of the translation start site of the FZD or Wnt mRNA.

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides complementary to and spanning the length of a FZD or Wnt mRNA can be prepared, followed by testing for inhibition of FZD or Wnt expression. Optionally, gaps of 5-10 nucleotides can be left between the oligonucleotides to reduce the number of oligonucleotides synthesized and tested.

The antisense nucleic acid can be chemically synthesized, e.g., using a commercial nucleic acid synthesizer according to the vendor's instructions. Alternatively, the antisense nucleic acids can be produced using recombinant DNA techniques. An antisense nucleic acid can incorporate only naturally occurring nucleotides. Alternatively, it can incorporate variously modified nucleotides or nucleotide analogs to increase its in vivo half-life or to increase the stability of the duplex formed between the antisense molecule and its target RNA. Examples of nucleotide analogs include phosphorothioate derivatives and acridine-substituted nucleotides. Given the description of the targets and sequences, the design and production of suitable antisense molecules is within ordinary skill in the art. For guidance concerning antisense nucleic acids, see, e.g., Goodchild, "Inhibition of Gene Expression by Oligonucleotides," in *Topics in Molecular and Structural Biology, Vol. 12: Oligodeoxynucleotides* (Cohen, ed.), MacMillan Press, London, pp. 53-77 (1989).

Delivery of antisense oligonucleotides can be accomplished by any method known to those of skill in the art. For example, delivery of antisense oligonucleotides for cell culture and/or ex vivo work can be performed by standard methods such as the liposome method or simply by addition of membrane-permeable oligonucleotides.

Delivery of antisense oligonucleotides for in vivo applications can be accomplished, for example, via local injection of the antisense oligonucleotides at a selected site, e.g., a liver. This method has previously been demonstrated for psoriasis growth inhibition and for cytomegalovirus inhibition. See, for example, Wraight et al., (2001). *Pharmacol Ther.* 90(1):89-104; Anderson et al., (1996) *Antimicrob Agents Chemother* 40: 2004-2011; and Crooke et al., (1996) *J Pharmacol Exp Ther* 277: 923-937.

Similarly, RNA interference (RNAi) techniques can be used to inhibit FZD or Wnt expression, in addition or as an alternative to the use of antisense techniques. For example, small interfering RNA (siRNA) duplexes directed against FZD or Wnt nucleic acids could be synthesized and used to prevent expression of the encoded protein(s). Exemplary Wnt3 siRNAs are described in the Examples section, below.

Another approach to inhibiting Wnt/FZD signaling involves administering to a patient a compound, e.g., a candidate compound or anti-cancer agent, that binds to FZD polypeptides (e.g., FZD 7 polypeptides) and/or their binding partners (e.g., Wnt 3, 8b and/or 11), thereby preventing interaction between the two. Such compounds and agents may, for example, bind to the FZD polypeptide (e.g., to the CRD domain of the FZD polypeptide) and/or to the Wnt polypeptide (e.g., to a binding domain of the Wnt polypeptide) in such a way that interaction between the proteins is prevented. Such candidate compounds and anti-cancer agents can be identified using screening methods described herein. Examples of compounds that can bind to a Wnt polypeptide, e.g., Wnt 3, 8b and/or 11, are a FZD 7 receptor or truncated form thereof, and an anti-Wnt antibody (or FZD-binding fragment thereof), e.g., the anti-Wnt3 antibody described in the Examples section, below.

Yet another approach to inhibiting Wnt/FZD signaling involves administering to a patient a vector (e.g., a gene therapy vector) that encodes a mutated (e.g., truncated) form of a FZD receptor, e.g., a FZD 7 receptor. Expression of the mutated form of the receptor by the patient's cells that incorporate the construct can interfere with Wnt/FZD signaling in the cells. For example, a construct that encodes a secreted and soluble form of a FZD receptor (e.g., a FZD 7 receptor) can be used. Expression of such a construct by target cells would cause the cells to secrete a soluble form of the FZD receptor that would bind Wnt polypeptides, rendering them unable to bind to intact FZD receptors on the cell surface. Alternatively or in addition, a construct that encodes a membrane bound but inactive form of a FZD receptor (i.e., a mutant FZD receptor unable to perform some function performed by a counterpart wild-type FZD receptor) can be used. Expression of such a construct by target cells may bind up Wnt polypeptides or interfere with Wnt/FZD signaling via an internal mechanism not involving Wnt polypeptides. Still another approach to inhibiting Wnt/FZD signaling involves administering to a patient a vector (e.g., a gene therapy vector) that encodes a Wnt11 polypeptide, which is a suppressor of the canonical Wnt pathway in HCC. The vector can be derived from a non-replicating linear or circular DNA or RNA vector, or from an autonomously replicating plasmid or viral vector. Methods for constructing suitable expression vectors are known in the art, and useful materials are commercially available.

Increasing Wnt/FZD Signaling

New or supplemental Wnt/FZD signaling can be provided in vivo by increasing expression of FZD polypeptides (e.g., FZD 8 polypeptides) and/or Wnt polypeptides (e.g., Wnt3 polypeptides) in the patient. For example, a FZD or Wnt polypeptide can be generated directly within an organism, e.g., a human, by expressing within the cells of the organism a nucleic acid construct containing a nucleotide sequence encoding a FZD polypeptide (e.g., a FZD 8 polypeptide) and/or Wnt polypeptide (e.g., Wnt3 polypeptide). Any appropriate expression vector suitable for transfecting the cells of the organism of interest can be used for such purposes.

VII. Transgenic Animals

The present invention also features transgenic animals that develop liver cancer and overexpress FZD 7 in their liver cells. Such animals represent model systems for the study of liver cancer and for the development of therapeutic agents that can modulate Wnt/FZD signaling and treat cancer.

Transgenic animals can be, for example, farm animals (pigs, goats, sheep, cows, horses, rabbits, and the like), rodents (such as rats, guinea pigs, and mice), non-human primates (for example, baboons, monkeys, and chimpanzees), and domestic animals (for example, dogs and cats).

Any technique known in the art can be used to introduce transgenes into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983). Especially useful are the methods described in Yang et al. (*Proc. Natl. Acac. Sci. USA* 94:3004-3009, 1997).

For a review of techniques that can be used to generate and assess transgenic animals, skilled artisans can consult Gordon (*Intl. Rev. Cytol.* 115:171-229, 1989), and may obtain additional guidance from, for example: Hogan et al. *Manipulating the Mouse Embryo*, Cold Spring Harbor Press, Cold Spring Harbor, N.Y., 1986); Krimpenfort et al. (*Bio/Technology* 9:86, 1991), Palmiter et al. (*Cell* 41:343, 1985), Kraemer et al. (*Genetic Manipulation of the Early Mammalian Embryo*, Cold Spring Harbor Press, Cold Spring Harbor, N.Y., 1985), Hammer et al. (*Nature* 315:680, 1985), Purcel et al. (*Science*, 244:1281, 1986), Wagner et al. (U.S. Pat. No. 5,175,385), and Krimpenfort et al. (U.S. Pat. No. 5,175,384).

EXAMPLES

The invention is illustrated in part by the following examples, which are not to be taken as limiting the invention in any way.

Example 1

Identification of Natural Wnt Ligands for Inhibition of HCC Growth

Methods

Preparation of Cell Surface HSPG and Fractionation by Heparin-Agarose Chromatography.

Huh7 cells were grown to 70% confluency in 10% FBS (Sigma, St. Louis, Mo.) MEM (Mediatech, Herndon, Va., USA). The media were changed to 0% FBS MEM 24 hrs after incubation, and the cells were treated with or without heparin (50 ug/ml) in 0.1% FBS MEM for 12 hrs. Cells were washed 5 times with ice-cold PBS and cell layers were incubated with crystallized trypsin (20 ug/ml) in Tris-buffered saline/EDTA for 10 min on ice. Trypsin activity was stopped by the addition of soybean trypsin inhibitor at a final concentration of 100 ug/ml. Contaminated cells were removed by centrifugation at 400×g for 5 min at 4° C. from trypsinate.

The trypsinate was subjected to heparin-agarose chromatography. In brief, trypsinate was incubated with heparin (4%) agarose beads for overnight at 4° C. and beads were collected by centrifugation at 2000×g for 4 min, washed beads with 20 volumes of 0.1 M NaCl in PBS. Eluted fractions were collected with 0.25, 0.5, 0.75, and 1.0 M NaCl in PBS.

Two-Dimensional Gel Electrophoresis, In-Gel Digestion and Peptide Mapping.

Fractionated samples from heparin-agarose chromatography were prepared by precipitation and rehydration with IPG buffer for isoelectric focusing (IEF). IEF was carried out using ZOOM IPGRunner (Invitrogen™, Carlsbad, Calif.), according to the manufacturer's protocol. ZOOM strips (pH 3-10) were rehydrated with samples for overnight, then a step voltage ramping method was applied as follows: 200 V for 20 min, 450 V for 15 min, 750 V for 15 min, and 2000 V for 120 min. Focused gels were subjected to SDS-PAGE using ZOOM gels (Invitrogen) as second dimensional electrophoresis. Following electrophoresis, gels were stained using SilverQuest Silver Staining kit (Invitrogen).

Protein spots excised from silver-stained gels were destained and dried before enzymatic digestion with sequence grade modified trypsin (Promega, Madison, Wis.). Tryptic peptides were desalted and concentrated with Zip-Tip$_{C18}$ (Millipore, Bedford, Mass.). The concentrated tryptic peptides were applied to SEND ProteinChip and performed peptide mapping using PBSII (Ciphergen, Fremont, Calif.). Peptide mass fingerprinting was conducted with the database search tool MS-fit in the program Protein Prospector, available at http://prospector.ucsf.edu. A number of restrictions were applied to the initial search based on localization of the spot in the 2-D gel: species=*homo sapiens*, pI range=6-9.5, mass range=35-50 kDa.

RT-PCR Analysis.

Total cellular RNA was extracted by using TRIzol® Reagent (Invitrogen) from HepG2, Hep3B, Huh7 and Focus cell lines. First-strand cDNA was synthesized from 250 ng of total RNA with random hexamers and AMV RT using First Strand cDNA Synthesis Kit for RT-PCR (AMV) (Roche Diagnostics, Indianapolis, Ind.) in 20 µl of the reaction mixture. PCR was performed in a thermocycler (MJ Research Inc., Waltham, Mass.) using 50 ng of cDNA and High Fidelity PCR Master (Roche Diagnostics). The primer pairs for each Wnt ligand are listed in Table 1, below. The final concentration of each primer was 250 nM. After initial denaturation at 94° C. for 4 min, reactions were subjected to 35 cycles of the following thermal program: 94° C. for 30 s, 55° C. for 30 s, and 72° C. for 1 min, followed by a final elongation step at 72° C. for 10 min. The amplified products were analyzed on ethidium bromide-stained 2% agarose gel.

qRT-PCR Assay.

Extraction of total RNA and RT reaction from the liver tissues and HCC cell lines were conducted as described above. To determine the mRNA expression levels of Wnt3, Wnt11 and FZD7, qRT-PCR was performed using iCycler iQ Multi-Color Real Time PCR Detection System (Bio-Rad, Hercules, Calif.) with a mixture composed of SYBR Green PCR Master Mix (Applied Biosystems, Foster City, Calif.), 400 nM of each primer and 5 ng of cDNA (equivalent total RNA) from unknown samples. The thermal cycling conditions comprised an initial step at 95° C. for 10 min, followed by 40 cycles at 95° C. for 15 s, 60° C. for 30 s, and 72° C. for 30 s. The primer sequences for Wnt3, Wnt11, FZD7 and 18SrRNA were as follows:
(1) Wnt-3,5'-ACTTCGGCGTGTTAGTGTCC-3' (forward) (SEQ ID NO:68) and 5'-CATTTGAGGTGCATGTGGTC-3' (reverse) (SEQ ID NO: 69);
(2) Wnt11, 5'-TTCCGATGCTCCTATGAAGG-3' (forward) (SEQ ID NO:70) and 5'-AGACACCCCATGGCACTTAC-3' (reverse) (SEQ ID NO:71);
(3) FZD7,5'-GCCGCTTCTACCACAGACT-3' (forward) (SEQ ID NO:72) and 5'-TTCATACCGCAGTCTCCCC-3' (reverse) (SEQ ID NO:73);
(4) 18SrRNA, 5'-GGACACGGACAGGATTGACA-3' (forward) (SEQ ID NO:74) and
5'-ACCCACGGAATCGAGAAAGA-3' (reverse) (SEQ ID NO:75). The sizes of amplicons were 130 bp for Wnt3, 133 bp for Wnt11, 54 bp for FZD7 and 50 bp for 18SrRNA. After visualization of the PCR products by 1.5% agarose gel electrophoresis and ethidium bromide, PCR products were excised and cloned into the pCR 2.1 Vector (Invitrogen). Sequencing was performed in both directions using T7 forward and M13 reverse primers. After confirmation of the nucleotide sequences, standards for the real-time PCR were prepared with 10-fold dilutions of the each PCR products cloned into the pCR 2.1 Vector. The copy numbers of Wnt3, Wnt11 and FZD7 mRNAs were quantified in unknown samples by measuring the Ct values followed by normalization to 18SrRNA after comparison with standard curves for each gene. Experiments were performed in duplicate.

Preparation of Plasmids and Anti-Wnt3 Ab.

Because 22 amino acids from the C-terminal end of the human Wnt3 plasmid were missing in the original plasmid (22), it was extended to the full-length sequence using three runs of PCR amplification based on the sequence of human Wnt3, which was cloned into pcDNA™ 3.1/myc-His A (Invitrogen) via HindIII and EcoRI restriction enzyme sites. The sequences of primers were (SEQ ID NO: 76)
5'-TAGTTAAGCTTACCATGGAGCCCCACCTGCTC-3'
(forward), (SEQ ID NO: 77)
5'-GCAGCTGACGTAGCAGCACCAGTGGAAGATGCAGTG-3'
(reverse-1), (SEQ ID NO: 78)
5'-GTAGATGCGAATACACTCCTGGCAGCTGACGTAGCA-3'
(reverse-2), (SEQ ID NO: 79)
5'-TGCTTGAATTCCTTGCAGGTGTGCACGTCGTAGATGCGAATACA-3'
(reverse 3).

Rabbit polyclonal antibodies were prepared against a synthetic peptide corresponding to amino acids 259-274 of human Wnt3 ($^{259}$LRAKYSLFKPPTERDL$^{274}$) (SEQ ID NO:80). The peptide sequence did not share significant homology with other members of Wnt family or other known proteins. The specificity of antibody was verified by Western blot analysis using HCC cell lines transfected with myc-tagged Wnt3 plasmid.

Cell Culture

Hep3B, Huh7 and Focus cell lines were grown in MEM, supplemented with 10% FBS and 1× minimum essential medium nonessential amino acid solution (Sigma). HepG2 cells were excluded because of the deletion mutation in the β-catenin gene (31). Transfection experiments were performed at 70% confluency using LipofectAMINE 2000 (Invitrogen) or TransIT-LT1 (Mirus, Madison, Wis.) according to the manufacture's instructions. Tcf transcriptional activity was analyzed using Luciferase Assay System (Promega, Madison, Wis.) after transfecting cells with pSUPER8xTOPFLASH or pSUPER8xFOPFLASH (32). Raw data for luciferase activity were normalized using β-galactosidase activity as a transfection control. Experiments were carried out in triplicate and repeated three times to verify results.

Effects of Wnt3 Overexpression in HCC Cells.

The HCC cells were transfected with pcDNA3.1/myc-His A (control plasmid) or Wnt3 plasmids, pSUPER8xTOPFLASH or pSUPER8xFOPFLASH, and β-galactosidase plasmid. Twenty-four hours after transfection, the cells were incubated with 0% FBS MEM for 24 h, and then stimulated with 1% FBS MEM. The cells were harvested at 2 h and 24 h after the stimulation, and subjected to the luciferase assay and Western blot analysis for Wnt3 and β-catenin.

Effects of Anti-Wnt3 Antibodies.

For blocking experiments, cells were seeded in 12-well plates and transfected with pSUPER8xTOPFLASH or pSUPER8xFOPFLASH with β-galactosidase plasmid as described above. After serum-deprivation for 24 h, the cells were incubated with 1% FBS MEM containing either anti-Wnt3 Ab or control Ab (10 µg/ml), and harvested 24 h after incubation. Normal rabbit IgG (Upstate, Waltham, Mass.) was used as a control antibody.

Effects of siRNA.

Control siRNA and Wnt3 siRNAs (WNT3-1: 5'-GGAAAAAUGCCACUGCAUC-3' (SEQ ID NO:81), WNT3-2: 5'-GGAGUGUAUUCGCAUCUAC-3' (SEQ ID NO:82), WNT3-3: 5'-GGCUUAUCUUUGCACAUGU-3' (SEQ ID NO:83)) were purchased from Ambion (Austin, Tex.) and transfected into HCC cells at a concentration of 10 or 100 nM with pSUPER8xTOPFLASH or pSUPER8xFOPFLASH, and β-galactosidase plasmid using TransIT-LT1 or DharmaFECT 4 (Dharmacon, Chicago, Ill.).

Forty-eight hours after transfection, the mRNA expression levels of Wnt3 and Tcf transcriptional activity were measured by qRT-PCR and luciferase assay, respectively.

Effect of Blocking Anti-Wnt3 Ab on Wound Healing.

Focus cells were plated in a 6-well plate. Confluent monolayer cells were wounded with sterile plastic 200 µl micropipette tips. The cells were then treated with media with either anti-Wnt3 Ab or rabbit IgG, and photographed at different time points.

Western Blot Analysis

For total protein extraction, the cells were homogenized in lysis buffer (30 mM Tris, pH 7.5, 150 mM sodium chloride, 1% NP-40, 0.5% sodium deoxycholate, 0.1% SDS, 10% glycerol, and 2 mM EDTA) with proteinase inhibitors (Roche Diagnostics) and sonicated. Protein concentration was determined using the BCA Protein Assay Kit (Pierce, Rockford, Ill.) with BSA as standard. Equal amounts of proteins (150 µg) were separated using 12-15% SDS-PAGE and transferred to PVDF membranes (PerkinElmer, Wellesley, Mass.). The membranes were blocked with 5% BSA in Tris-buffered saline containing 0.1% Tween 20 and then incubated overnight at 4° C. with a mouse monoclonal anti-myc Ab diluted at 1:1,000 (Santa Cruz Biotechnology Inc., Santa Cruz, Calif.), a rabbit polyclonal anti-Wnt3 Ab diluted at 1:200, a mouse monoclonal anti-β-catenin Ab diluted at 1:1,000 (Transduction Laboratories, San Diego, Calif.), or a rabbit polyclonal anti-hsp90 Ab diluted at 1:2,000 (Santa Cruz Biotechnology Inc.). After washing with Tris-buffered saline containing 0.1% Tween 20, the membrane was incubated for 1.5 hour at room temperature with a secondary HRP antibody diluted 1:10,000 and visualized using the chemiluminescence imaging Western Lightning (PerkinElmer).

Human HCC Tissues.

Seventeen pairs of HCC and matched, uninvolved, peritumoral liver tissues were obtained from South Korea and South Africa. Twelve pairs of samples were from Korean patients who underwent surgical resection. Nine of the 12 patients were males and the median age was 52 (range, 22-67). Eleven patients were positive for hepatitis B surface antigen (HBsAg) and the etiology was unknown in the remaining 1 patient. Seven patients (58%) had underlying liver cirrhosis. Five liver tissues, obtained from the Korean patients who underwent hepatic resection for single metastasis of colorectal cancers to the liver, served as the controls for normal liver tissues. Four patients were males and the median age was 46 (range 37-57). Histologic examination did not show any pathology in the surrounding, peritumoral liver tissues.

Immunohistochemistry for β-Catenin.

Formalin-fixed, paraffin-embedded sections were deparaffinized in xylene and rehydrated by decreasing concentrations of ethanol. Sections were immersed in 10 mM sodium citrate buffer (pH 6.0), boiled in a microwave oven for 10 min, and cooled to room temperature for epitope retrieval. Slides were then processed using a Universal DakoCytomation LSAB®+Kit, Peroxidase (DAKO Corp., Carpinteria, Calif.) according to the manufacturer's instructions. Endogenous peroxidase, avidin and biotin activities were blocked by incubation with 3% hydrogen peroxide and Endogenous Avidin/Biotin Blocking Kit (Zymed Laboratories Inc., South San Francisco, Calif.). Sections were incubated at 4° C. overnight with a 1:500 dilution of anti-human β-catenin monoclonal Ab. For negative controls, the primary antibody was replaced with PBS. The β-catenin expression patterns were classified into two groups according to the presence of nuclear staining. Cytoplasmic staining in tumor tissues was also compared to that in peritumoral tissues.

Mutational Analysis for Exon-3 of the β-Catenin Gene.

Exon 3 mutation of β-catenin gene was analyzed by the method of Wong et al. (11) with some modifications. Briefly, a 218-bp fragment of exon 3 of the β-catenin gene was amplified from cDNA (50 ng) from HCCs and surrounding peritumoral liver tissues using Expand High Fidelity PCR System (Roche Diagnostics). The sequences of primers were 5'-GATTTGATGGAGTTGGACATGG-3' (forward) (SEQ ID NO:84) and 5'-TGTTCTTGAGTGAAGGACTGAG-3' (reverse) (SEQ ID NO:85). The thermal cycling conditions comprised an initial denaturating step at 94° C. for 3 min, followed by 35 cycles at 95° C. for 30 s, 58° C. for 30 s, and 72° C. for 30 s. After visualization of the PCR products, PCR products were cloned into the pCR 2.1 Vector (Invitrogen) and subsequently sequenced using T7 forward and M13 reverse primers. At least 5 clones from each PCR product were analyzed for the sequencing.

Results

Identification of Wnt Ligands in HCC Cell Lines.

Figure 1C:
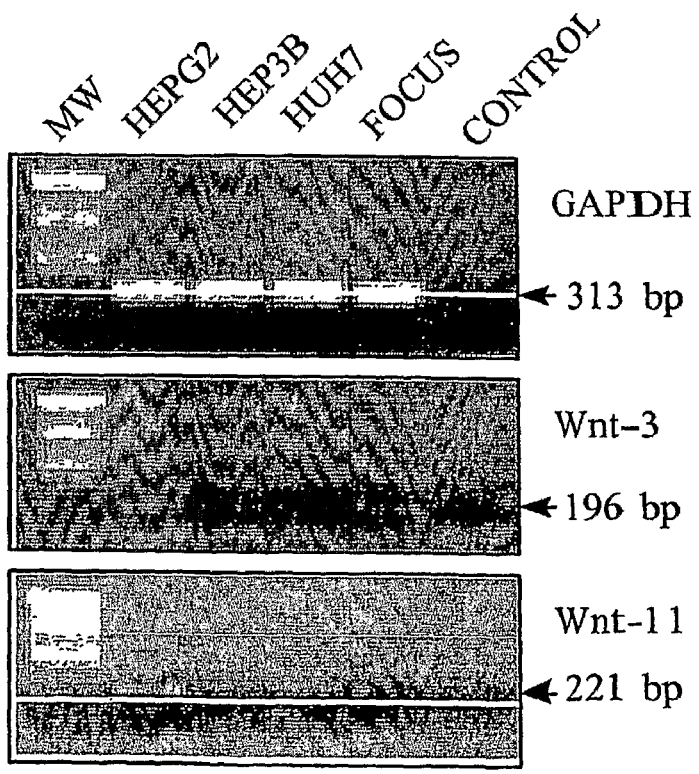
FIG. 1C are pictures of agarose gels that illustrate the detection of Wnt ligand mRNA in various hepatocellular carcinoma cell lines using RT-PCR. Wnt-3 mRNA was detected in all HCC cell lines and Wnt-11 mRNA was detected in 3 HCC lines but not Focus cells. No other Wnt mRNAs were detectable by RT-PCR.
Figure 1B:
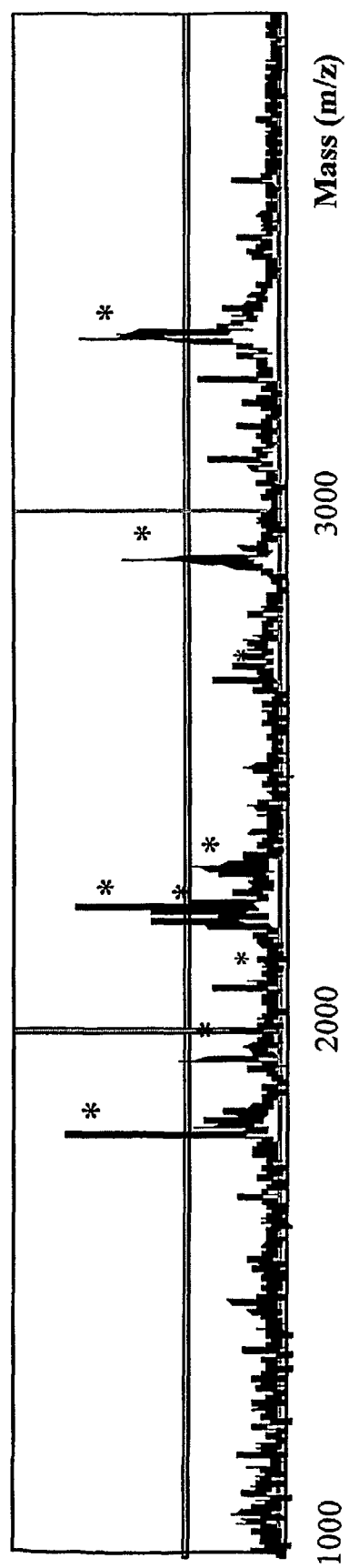
FIG. 1B is a mass-spectrum of tryptic peptides obtained from spot 1. Spot 1 was excised, destained, and digested with trypsin. The peptide masses were analyzed on a PBSII instrument. The marked peaks (*) represent peptides that matched the calculated masses of human Wnt-11 peptides.
Figure 2A:
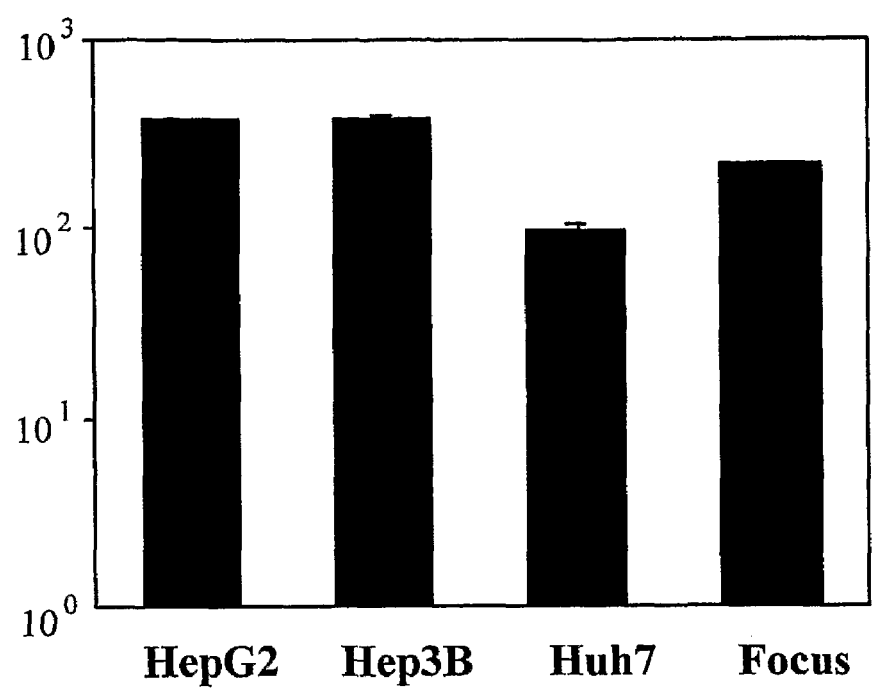
FIG. 2A is a bar graph illustrating Wnt3 mRNA levels as determined by qRT-PCR in HCC cell lines. 18SrRNA levels were used as internal controls, and Wnt3 and Wnt11 mRNA levels were expressed as copy numbers per $10^9$ 18SrRNA. The expression levels (mean±SE) of Wnt3 mRNA in HCC cell lines were 370.0±10.3 in HepG2, 381.3±12.7 in Hep3B, 95.2±6.3 in Huh7 and 210.4±9.5 copies per $10^9$ 18SrRNA.
Figure 2B:
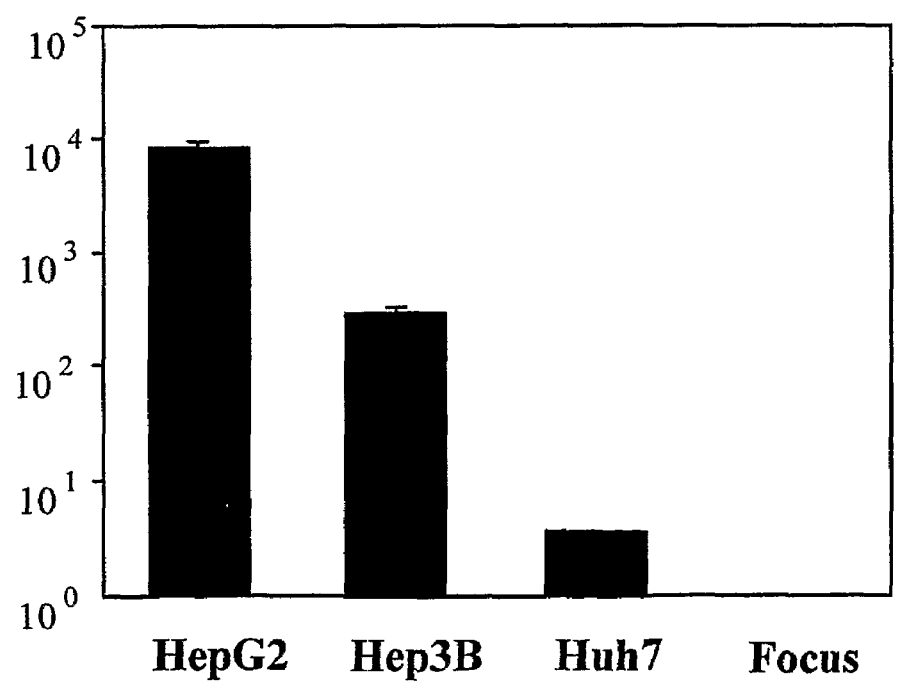
FIG. 2B is a bar graph illustrating Wnt11 mRNA levels as determined by qRT-PCR in HCC cell lines. 18SrRNA levels were used as internal controls, and Wnt11 mRNA levels were expressed as copy numbers per $10^9$ 18SrRNA. Wnt11 mRNA expression levels were 8,499.3±845.0 in HepG2, 290.9±40.1 in Hep3B and 3.57±0.2 copies per $10^9$ 18SrRNA in Huh7 cells. Wnt11 mRNA could not be detected in focus cells with qRT-PCR, consistent with the result of conventional RT-PCR.

Since Wnt proteins are mainly associated with ECM in cell surface, an attempt was made to purify cell surface HSPG including Wnt protein(s) as an associated form in Huh7. Huh7-HSPG prepared by trypsin was subjected to heparin-agarose affinity resin for pre-fractionation. Eluted fractions were applied to SDS-PAGE and compared the protein bands between heparin-treated and non-treated samples. From a 0.25 M NaCl eluted fraction, an approximately 45 kDa protein band was distinguishable in the heparin-untreated fraction (data not shown). As the estimated molecular weight of Wnt proteins is in the range of 35-45 kDa, this protein band was considered to potentially include Wnt proteins. To define this protein band, two-dimensional electrophoresis was performed. As shown in FIG. 1A, there were several silver-stained protein spots showing different levels of protein expression between heparin-treated and untreated samples. Protein spots of 35-55 kDa and pI 5-9.5 were considered candidates for Wnt ligand proteins. Two up-regulated protein spots in heparin-untreated samples were investigated since Wnt proteins can be released by heparin treatment. Excised protein spots from silver-stained two-dimensional gels were subjected to in-gel digestion, followed by peptide mapping by mass spectrometry. Data analysis revealed that nine peptides matched human Wnt11 protein, as shown in FIG. 1B. To further corroborate this finding, Wnt mRNA expression was examined by RT-PCR in HCC cell lines using 19 pairs of primers specific for all the known human Wnt ligands. As shown in FIG. 1C, only Wnt3 and Wnt11 mRNA, among all 19 Wnt genes examined, were expressed in HCC cell lines. None of other known Wnt mRNAs were detected by RT-PCR. After Wnt3 and Wnt11 were identified in HCC cell lines, the mRNA expression levels were examined using quantitative real-time RT-PCR (qRT-PCR) assay in HCC cell lines. The expression levels (mean±SE) of Wnt3 mRNA in HCC cell lines were 370.0±10.3 in HepG2, 381.3±12.7 in Hep3B, 95.2±6.3 in Huh7 and 210.4±9.5 copies per $10^9$ 18S ribosomal RNA (18SrRNA). The Wnt11 mRNA expression levels were 8,499.3±845.0 in HepG2, 290.9±40.1 in Hep3B and 3.57±0.2 copies per $10^9$ 18SrRNA in Huh7 cells. Wnt11 mRNA could not be detected in Focus cells with real-time RT-PCR, consistent with the result of conventional RT-PCR (FIG. 2B).

Expression of Wnt3, Wnt11 and FZD7 mRNAs in Human HCC Tissues.

Figure 3A:
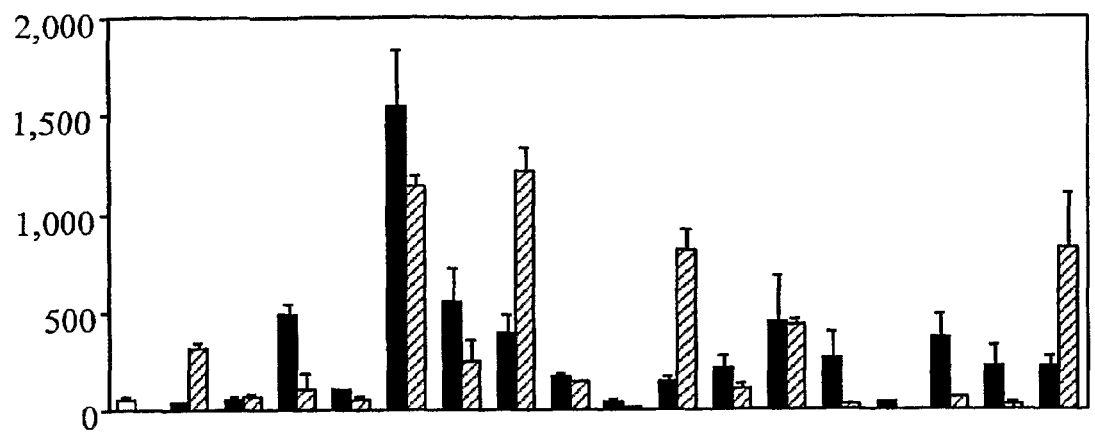
FIG. 3A is a bar graph illustrating expression of Wnt3 mRNA in human HCC tissues. The mRNA levels were measured by qRT-PCR. White bars represent mRNA levels in normal liver tissues. Black bars represent mRNA levels in HCC tissues. Gray bars represent mRNA levels in corresponding peritumoral tissues. Experiments were performed in duplicate and data are expressed as mean±SD. Seventy-seven percent of HCCs and 59% of peritumoral tissues showed increased Wnt3 mRNA expression levels above the value of mean±3 SD in normal liver tissues. Seventy-one percent of HCC tissues had increased Wnt3 mRNA expression levels compared to those in the corresponding peritumoral tissues.
Figure 3B:
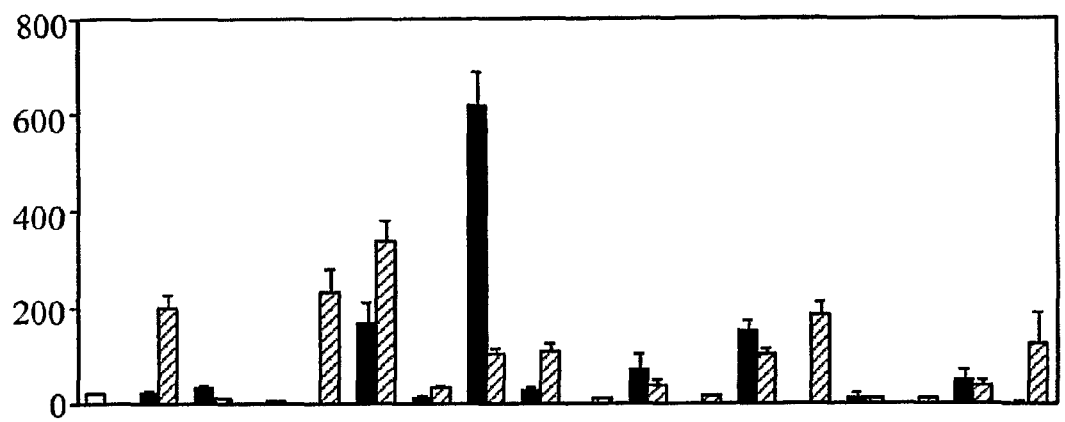
FIG. 3B is a bar graph illustrating expression of Wnt11 mRNA in human HCC tissues. The mRNA levels were measured by qRT-PCR. White bars represent mRNA levels in normal liver tissues. Black bars represent mRNA levels in HCC tissues. Gray bars represent mRNA levels in corresponding peritumoral tissues. Experiments were performed in duplicate and data are expressed as mean±SD. Forty-one percent of HCC tissues showed decreased expression even below the lower cut-off level of normal liver tissues, while none did in peritumoral tissues (P=0.0036 by Fischer's exact test). Sixty-five percent of paired samples also showed decreased expression of Wnt11 mRNA in tumors compared with corresponding peritumoral tissues.
Figure 3C:
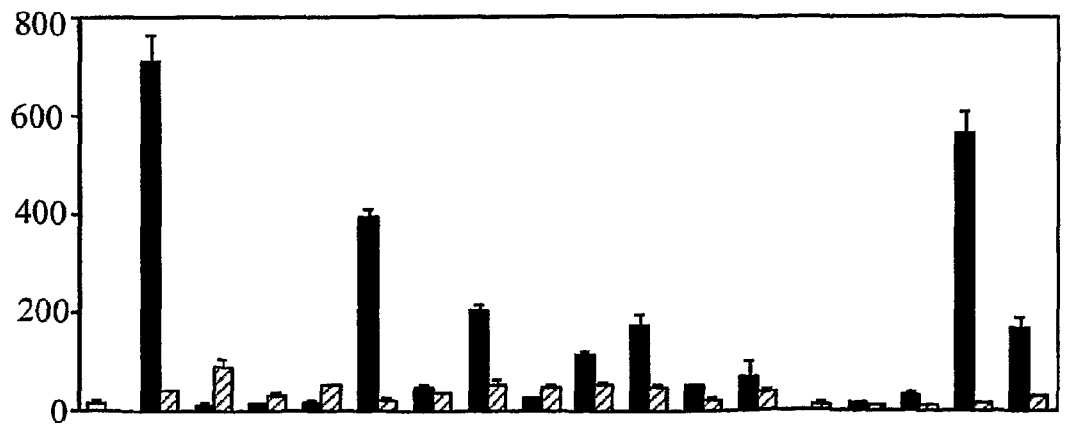
FIG. 3C is a bar graph illustrating expression of FZD7 mRNA in human HCC tissues. The mRNA levels were measured by qRT-PCR. White bars represent mRNA levels in normal liver tissues. Black bars represent mRNA levels in HCC tissues. Gray bars represent mRNA levels in corresponding peritumoral tissues. Experiments were performed in duplicate and data are expressed as mean±SD. Fifty-nine percent of both HCC and peritumoral tissues showed increased FZD7 mRNA expressions compared to those in normal liver tissues. Seventy-one percent of paired samples showed increased expression of FZD7 mRNA in tumors compared with corresponding, peritumoral tissues (P=0.031 by Wilcoxon signed-ranks test).
Figure 4A:
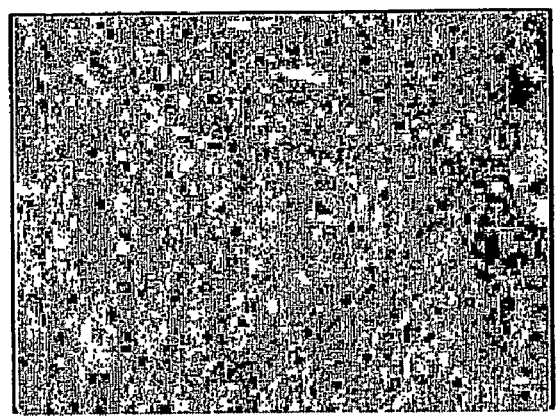
FIGS. 4A-4D are pictures of immunohistochemically stained human HCC and peritumoral tissues (magnification ×400).
Figure 4B:
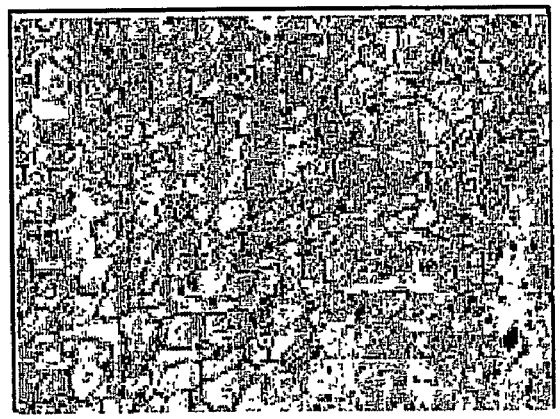
Figure 4C:
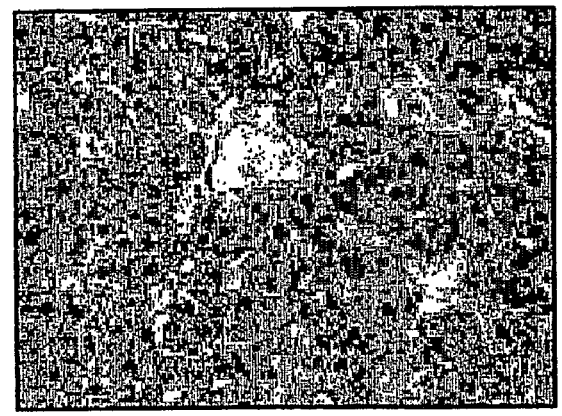
Figure 4D:
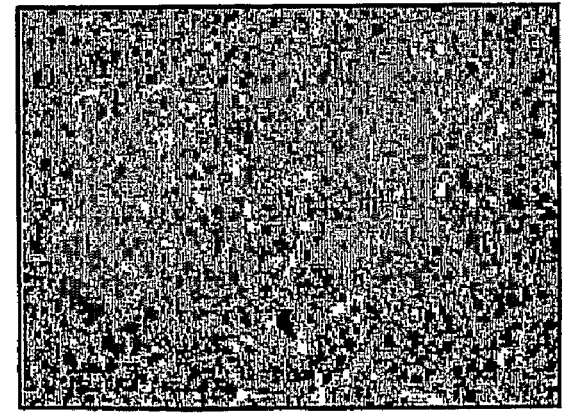

Thirteen of 17 (76.5%) HCC and 10 of 17 (58.8%) peritumoral tissues showed increased Wnt3 mRNA expression levels compared with those in normal controls, when the cut-off level was defined as a value of mean±3 SD in normal liver tissues. Only 1 peritumoral tissue showed decreased expression compared with normal liver tissues. Among 17 paired samples, 12 (70.6%) showed increased Wnt3 mRNA expression in tumors compared with corresponding, peritumoral tissues, but it was not statistically significant (P=0.435 by Wilcoxon signed-ranks test) (FIG. 3A). In contrast to Wnt3, 11 of 17 (64.7%) paired samples showed decreased expression of Wnt11 mRNA in tumors compared with corresponding, peritumoral tissues, which was not still statistically significant (P=0.227 by Wilcoxon signed-ranks test). However, 7 of 17 tumor tissues (41.2%) showed decreased expression even below the lower cut-off level of normal liver tissues, while none did in peritumoral tissues (P=0.0036 by Fischer's exact test). Five of 17 (29.4%) tumor tissues showed increased expression of Wnt11 mRNA compared with normal liver tissues, while 9 of 17 (52.9%) peritumoral tissues did. Both HCC and peritumoral tissues showed increased FZD7 mRNA expression in 10 of 17 (58.8%) samples compared with normal liver tissues (FIG. 3B). Twelve of 17 (70.6%) paired samples showed increased expression of FZD7 mRNA in tumors compared with corresponding peritumoral tissues, and this difference was statistically significant (P=0.031 by Wilcoxon signed-ranks test) (FIG. 3C).

Nuclear Accumulation of β-Catenin.

Immunohistochemical staining showed nuclear accumulation of β-catenin in 7 of 17 (41%) HCC tissues. There was no nuclear accumulation of β-catenin in surrounding, peritumoral tissues (FIG. 4). All of the 7 samples with nuclear accumulation of β-catenin also showed increased staining for β-catenin in the cytoplasm. Among the 10 tumor tissues without the nuclear accumulation of β-catenin, 1 sample showed increased cytoplasmic staining for β-catenin, compared to its corresponding peritumoral tissue.

By sequencing analysis, mutations on exon 3 of β-catenin gene were found in 4 of 17 (23.5%) HCC samples, while none in surrounding, peritumoral tissues. They were all single missense mutations affecting codons 35, 37 and 45 (two I35S, one S37C, and one S45F). Three of the 7 (42.9%) samples that showed nuclear accumulation of β-catenin by immunohistochemical staining had mutations at the region responsible for phosphorylation and ubiquitination of β-catenin. One sample that had a mutation in β-catenin gene (I35S) but did not have nuclear accumulation of β-catenin had increased cytoplasmic staining in immunohistochemical staining. All of the 4 remaining samples that had nuclear accumulation of β-catenin but did not have any mutation in β-catenin gene had increased FZD7 mRNA levels compared with paired peritumoral tissues. The FZD7 mRNA levels were also increased by 7-74 folds compared with the mean value of normal liver tissues. However, the mRNA expression levels of Wnt3 and/or Wnt11 were not related with β-catenin nuclear accumulation.

Effects of Wnt3 Overexpression in HCC Cell Lines.

Figure 5A:
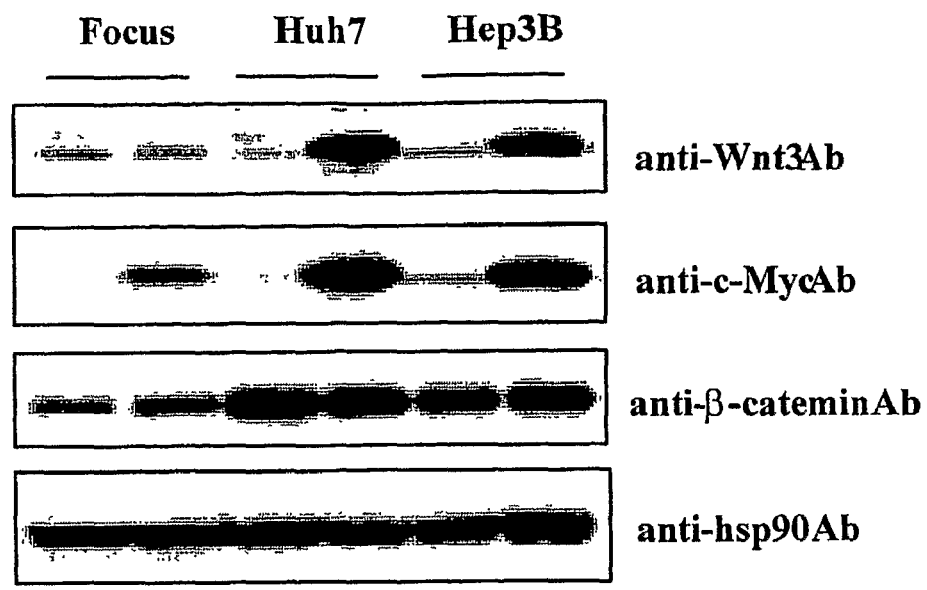
FIG. 5A is a composite picture of Western blots illustrating the effect of Wnt3 plasmid transfection on T-cell factor (Tcf) transcriptional activities in HCC cell lines. Focus, Huh7 and Hep3B cells were cotransfected with myc-tagged Wnt3 plasmid or pcDNA3.1/myc-His A plasmid, pSUPER8xTOPFLASH or pSUPER8xFOPFLASH, and β-galactosidase plasmid. Twenty-four hours after transfection, the cells were serum-starved for 24 h, and then stimulated with 1% FBS MEM. The cells were harvested at 2 h and 24 h after the stimulation and subjected to a luciferase assay and Western blot analysis for Wnt3 and β-catenin. Western blot analyses with rabbit polyclonal anti-Wnt3 antibody showed an increase of Wnt3 protein after transfection. Specificity of the polyclonal anti-Wnt3 antibody was verified with monoclonal anti-myc antibody. Note the increase of cellular β-catenin levels in Focus cells. Hsp90 protein was used as internal loading controls.
Figure 5B:
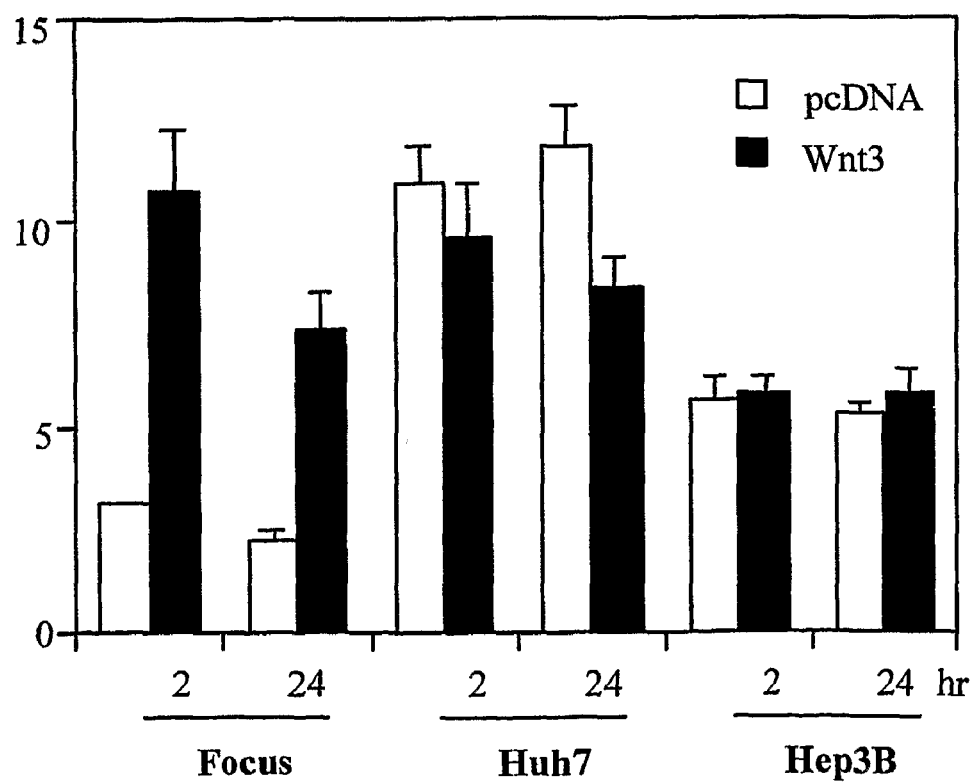
FIG. 5B is a bar graph illustrating changes in Tcf transcriptional activity in HCC cell lines after transfection with Wnt3 plasmid. The Tcf transcriptional activities were increased 3 fold in Focus cells following transfection, as compared to those in Focus cells transfected with control plasmid. Tcf transcriptional activities were slightly decreased in Huh7 cells and not changed in Hep3B cells following transfection. White bars denote cells transfected with the control plasmid (pcDNA) and black bars denote cells transfected with Wnt3 plasmid.

To determine the effect of Wnt3 on the canonical Wnt pathway in HCC, changes of T-cell factor (Tcf) transcriptional activity were examined after transfection with Wnt3 plasmid. Transfection with Wnt3 plasmid resulted in marked increases of both mRNA (data not shown) and protein expression levels, as demonstrated in FIG. 5A. The Tcf transcriptional activities also showed about 3-fold increases in Focus cells, compared to those of controls, which was statistically significant (P<0.01). However, the Tcf transcriptional activities were not changed in Hep3B cells, and even decreased in Huh7 cells, especially 24 h after stimulation (FIG. 5B). Consistent with these results, the cellular β-catenin level was increased in Focus cells after transfection with Wnt3 plasmid, while not changed or decreased in Hep3B or Huh7 cells, as demonstrated by Western blot analysis (FIG. 5A).

Antagonizing Wnt Signaling by Anti-Wnt3 Ab or Wnt3 siRNAs.

Figure 6A:
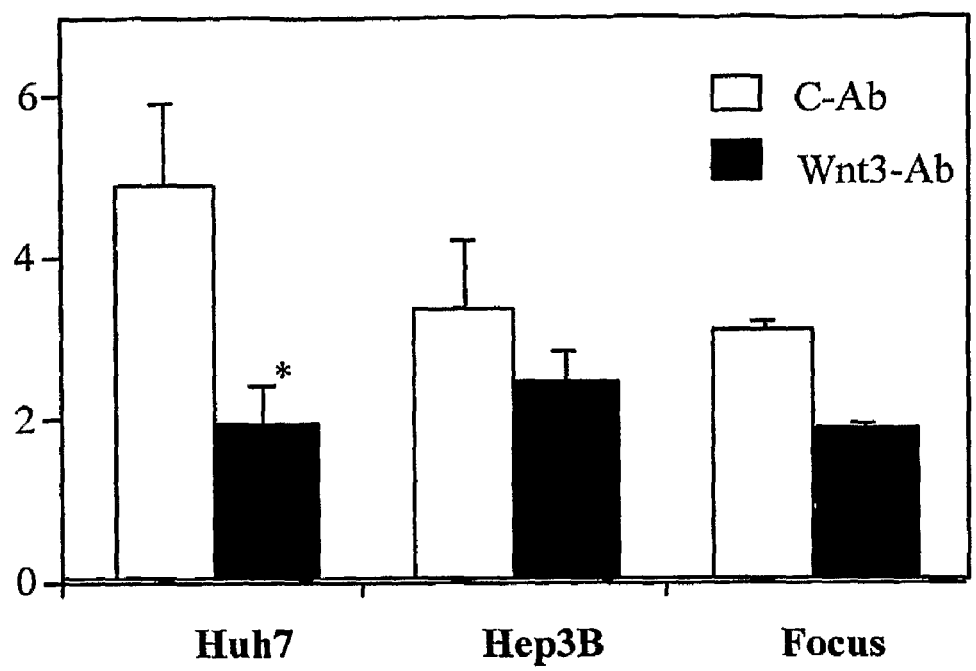
FIG. 6A is a bar graph illustrating the effects of anti-Wnt3 antibodies on Tcf transcriptional activities in HCC cell lines. HCC cells were seeded in 12-well plates and transfected with pSUPER8xTOPFLASH or pSUPER8xFOPFLASH with β-galactosidase plasmid. Cells were deprived of serum for 24 h and the cells were subsequently incubated with 1% FBS MEM containing either anti-Wnt3 antibodies (Wnt3-Ab; black bars) or control antibodies (10 μg/ml), and harvested 24 h after incubation. Normal rabbit IgG was used as a control antibody (C-Ab; white bars). Tcf transcriptional activities were decreased by 60% in Huh7, 26% in Hep3B, and 40% in Focus cells with polyclonal anti-Wnt3 antibody treatment.
Figure 6B:
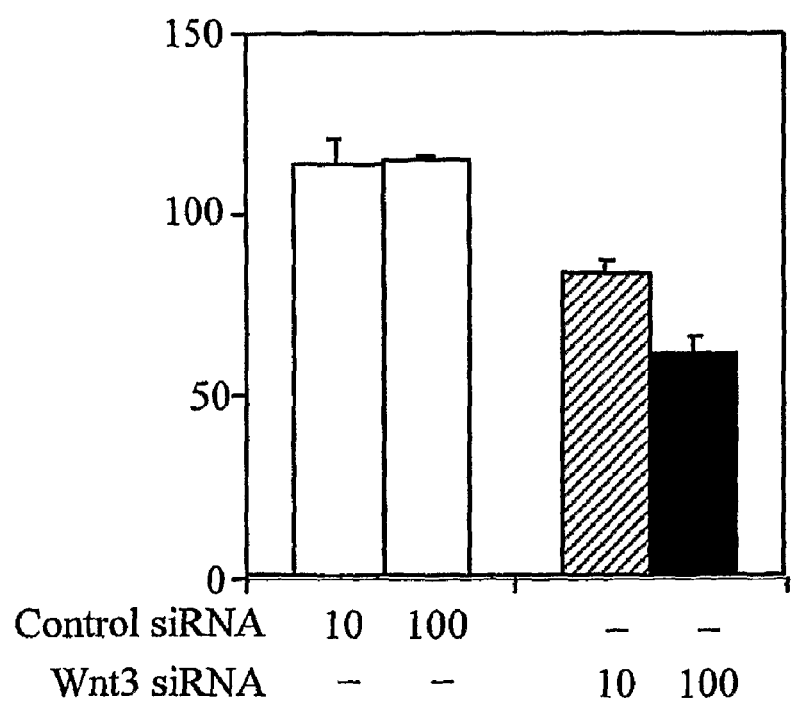
FIG. 6B is a bar graph illustrating the effect of siRNAs on endogenous Wnt3 mRNA expression. Control siRNA and Wnt3 siRNA (WNT3-3) at a concentration of 10 or 100 nM were transfected into HCC cells. Forty-eight hours after transfection, cells were harvested and Wnt3 mRNA expression levels were measured using qRT-PCR. siRNA Wnt3-3 caused a decrease of mRNA levels by 50-60% on average at a concentration of 100 nM in all of the 3 cell lines.
Figure 6C:
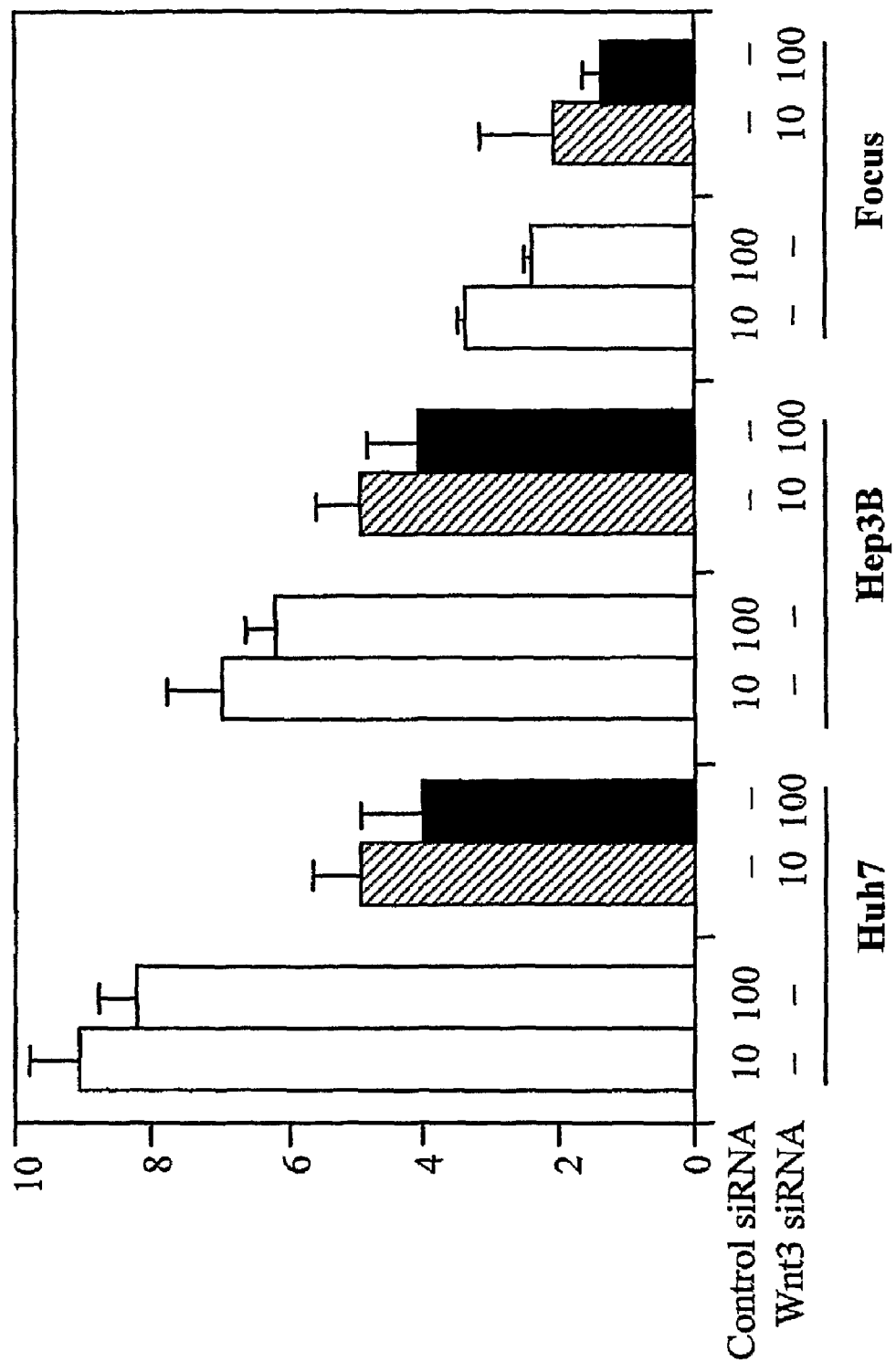
FIG. 6C is a bar graph illustrating the effects of Wnt3 siRNA on the Tcf transcriptional activities or HCC cell lines. Wnt3 siRNA or control siRNA was co-transfected in the presence of Tcf reporter at the indicated concentrations (nM). The Tcf transcriptional activities were decreased by 48.5% in Huh7, 33% in Hep3B, and 43.5% in Focus cells.

Next, the effects of inhibition by anti-Wnt3 Ab or siRNAs on the canonical pathway in HCC cell lines was examined, because the baseline Tcf transcriptional activities and cellular β-catenin levels were already high in Huh7 and Hep3B cells, compared to Focus cells (FIG. 5). Incubation with polyclonal anti-Wnt3 Ab resulted in decreases of luciferase activities by 60% in Huh7, 26% in Hep3B, and 40% in Focus cells (FIG. 6A). To confirm this inhibitory effect on the canonical pathway, siRNAs for Wnt3 were used. First, the inhibition efficiencies of 3 different kinds of siRNAs were evaluated in Huh7 and Hep3B cells using qRT-PCR assay. It was found that siRNA Wnt3-3 was the most efficient (data not shown) with an average decrease of mRNA levels by 50-60% at a concentration of 100 nM (FIG. 6B). Consistent with these reductions of mRNAs, the Tcf transcriptional activities were also decreased by 48.5% in Huh7, 33% in Hep3B, and 43.5% in Focus cells (FIG. 6C). Therefore, it was concluded that inhibition of Wnt3 could result in suppression of the canonical pathway in HCC cell lines.

Effects of Anti-Wnt3 Ab Treatment on Wound Healing in HCC Cells.

Figure 7:
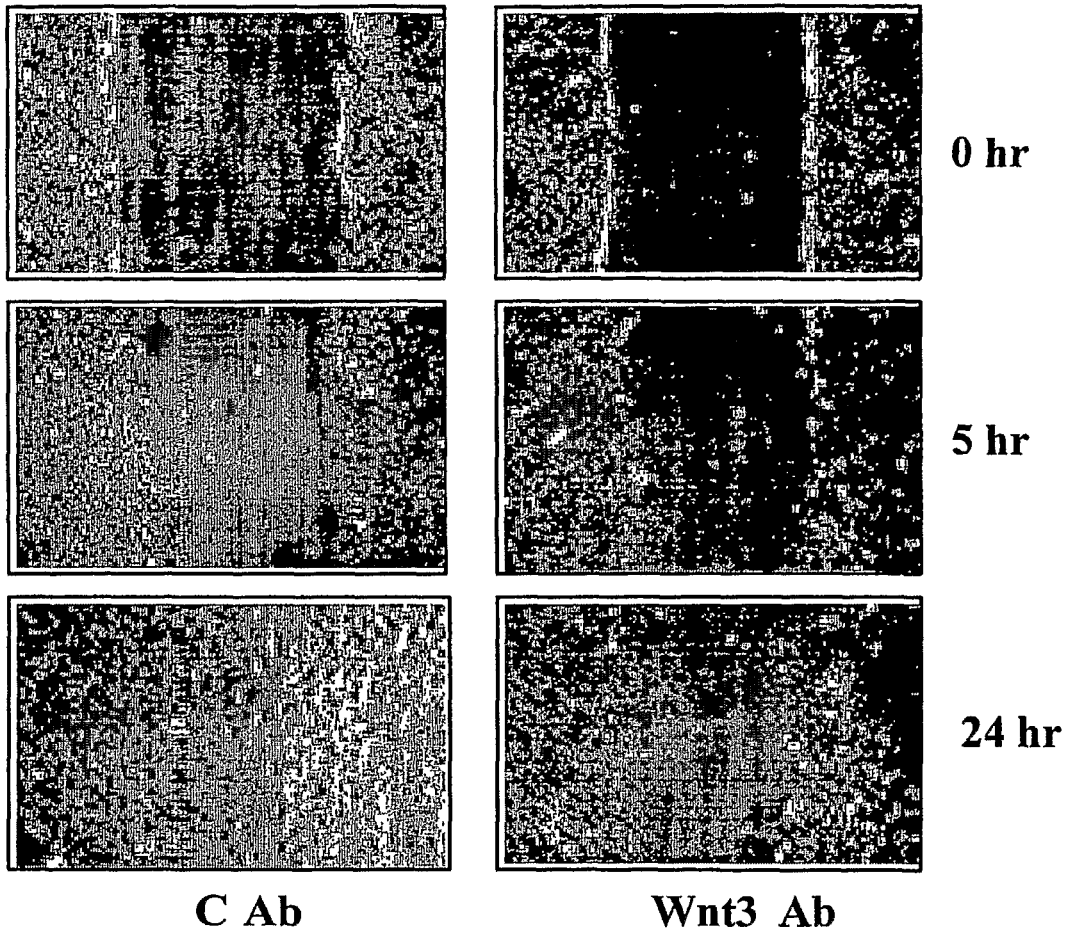
FIG. 7 are pictures of cell cultures illustrating delayed wound healing in Focus cells treated with anti-Wnt3 antibodies. Focus cells were plated in a 6-well plate. Confluent monolayer cells were wounded with sterile plastic 200 μl micropipette tips. The cells were then treated with media with either anti-Wnt3 Ab or rabbit IgG (control antibodies (C Ab); 10 μg/ml), and photographed at different time points. Focus cells treated with anti-Wnt3 Ab showed delayed wound healing. This effect was most prominent at 24 h. At 24 h, most of the wound was covered with migrating and/or proliferating cells in cells treated with C Ab, while it persisted in those treated with anti-Wnt3 Ab.

Whether inhibition of Tcf transcriptional activity could lead to functional changes of HCC cell behavior was also investigated. Wound healing assay using Focus cells showed delayed wound healing in cells treated with anti-Wnt3 Ab, and these changes were most prominent at 24 h. At 24 h, most of the wound was covered with migrating and/or proliferating cells in Focus cells treated with control Ab, while it persisted in cells treated with anti-Wnt3 Ab (FIG. 7).

This study analyzed the expression pattern of Wnt ligands in the liver and HCCs. mRNAs of Wnt3 and Wnt11 were found to be expressed in most of the HCC cell lines tested using conventional RT-PCR and qRT-PCR methods. Wnt11 expression at its protein level was also demonstrated using proteomics technology. Consistent with these observations in HCC cell lines, Wnt3 and Wnt11 mRNA expression was also confirmed in human liver tissues that included HCCs.

The expression patterns of Wnt3, Wnt11, and FZD7 was determined in human liver tissues including HCC and corresponding peritumoral tissues. mRNA levels of FZD7 in tumor tissues were more elevated than those in corresponding peritumoral tissues and normal liver tissues. Although there was no statistically significant difference in Wnt3 mRNA expression between HCC and peritumoral tissues, 71% of HCCs showed increased Wnt3 expression compared to their corresponding peritumoral tissues. Furthermore, 77% of HCCs and 59% of peritumoral tissues showed increased Wnt3 mRNA expression levels above the value of mean±3 SD in normal liver tissues. These findings suggest that upregulation of Wnt3 might be an early event during hepatocarcinogenesis and/or play an important role in hepatocyte regeneration during hepatic inflammation and necrosis.

Further, 65% of paired HCC samples showed decreased expression of Wnt11 mRNA in tumors compared with corresponding peritumoral tissues. 41% of tumor tissues showed decreased expression levels of Wnt11 even below the lower cut-off level of normal liver tissues. These findings were compatible with Wnt11's role as a suppressor of the canonical pathway.

Wnt3 overexpression was also found to activate the canonical Wnt pathway in Focus cells, as evidenced by a 3-fold increase of Tcf transcriptional activity and increased cellular β-catenin levels. However, the Tcf transcriptional activities were not changed in Hep3B cells and even decreased slightly in Huh7 cells, even though the Wnt3 mRNA and protein expressions were markedly increased after transfection.

Inhibition of Wnt3 by polyclonal anti-Wnt3 Ab or siRNAs decreased the Tcf transcriptional activities in all 3 HCC cell lines. These changes were most prominent in Huh7 cells that had the highest baseline Tcf transcriptional activities. Further, treatment of Focus cells with anti-Wnt3 Ab inhibited wound healing, suggesting that the functional consequence of this inhibition was decreased cell migration and proliferation.

Nuclear and/or cytoplasmic accumulation of β-catenin was observed in 8 of 17 (47%) HCC tissues and half of these cases had β-catenin gene mutations. The remaining 4 cases with β-catenin accumulation but without mutations had marked elevated levels of FZD7 in tumors, suggesting that FZD7 upregulation is directly related with the activation of the canonical Wnt signaling pathway in these tumors. The expression levels of Wnt3 or Wnt11 were related neither with the β-catenin accumulation nor with that of FZD7.

In conclusion, Wnt3 and Wnt11 was identified in HCC cell lines and in human liver tissues including HCC tissues. Wnt3 mRNA expression levels were upregulated in both HCC and peritumoral tissues compared to those in the normal liver tissues. Wnt11 mRNA expression was downregulated in HCC tissues. Inhibition of Wnt3 by anti-Wnt3 Ab or siRNA resulted in a decrease of the canonical Wnt signaling pathway and diminished wound healing, while Wnt3 stimulation increased the Tcf transcriptional activity in Focus cells. These findings suggest that Wnt3 is the natural Wnt ligand related to overexpression of FZD7 and activation of the canonical Wnt signaling pathway without β-catenin mutations during hepatocarcinogenesis.

REFERENCES

1. Davila, J. A., Morgan, R. O., Shaib, Y., McGlynn, K. A., and El-Serag, H. B. 2004. Hepatitis C infection and the increasing incidence of hepatocellular carcinoma: a population-based study. *Gastroenterology* 127:1372-1380.
2. Du, S. J., Purcell, S. M., Christian, J. L., McGrew, L. L., and Moon, R. T. 1995. Identification of distinct classes and functional domains of Wnts through expression of wild-type and chimeric proteins in *Xenopus* embryos. *Mol Cell Biol* 15:2625-2634.
3. Liang, H., Chen, Q., Coles, A. H., Anderson, S. J., Pihan, G., Bradley, A., Gerstein, R., Jurecic, R., and Jones, S. N. 2003. Wnt5a inhibits B cell proliferation and functions as a tumor suppressor in hematopoietic tissue. *Cancer Cell* 4:349-360.
4. Maye, P., Zheng, J., Li, L., and Wu, D. 2004. Multiple mechanisms for Wnt11-mediated repression of the canonical Wnt signaling pathway. *J Biol Chem* 279:24659-24665.
5. Iozzo, R. V., Eichstetter, I., and Danielson, K. G. 1995. Aberrant expression of the growth factor Wnt-5A in human malignancy. *Cancer Res* 55:3495-3499.
6. Lejeune, S., Huguet, E. L., Hamby, A., Poulsom, R., and Harris, A. L. 1995. Wnt5a cloning, expression, and up-regulation in human primary breast cancers. *Clin Cancer Res* 1:215-222.
7. Weeraratna, A. T., Jiang, Y., Hostetter, G., Rosenblatt, K., Duray, P., Bittner, M., and Trent, J. M. 2002. Wnt5a signaling directly affects cell motility and invasion of metastatic melanoma. *Cancer Cell* 1:279-288.
8. Kinzler, K. W., and Vogelstein, B. 1996. Lessons from hereditary colorectal cancer. *Cell* 87:159-170.
9. Devereux, T. R., Stem, M. C., Flake, G. P., Yu, M. C., Zhang, Z. Q., London, S. J., and Taylor, J. A. 2001. CTNNB1 mutations and beta-catenin protein accumulation in human hepatocellular carcinomas associated with high exposure to aflatoxin B1. *Mol Carcinog* 31:68-73.
10. Hsu, H. C., Jeng, Y. M., Mao, T. L., Chu, J. S., Lai, P. L., and Peng, S. Y. 2000. Beta-catenin mutations are associated with a subset of low-stage hepatocellular carcinoma negative for hepatitis B virus and with favorable prognosis. *Am J Pathol* 157:763-770.
11. Wong, C. M., Fan, S. T., and Ng, I. O. 2001. beta-Catenin mutation and overexpression in hepatocellular carcinoma: clinicopathologic and prognostic significance. *Cancer* 92:136-145.
12. Huang, H., Fujii, H., Sankila, A., Mahler-Araujo, B. M., Matsuda, M., Cathomas, G., and Ohgaki, H.1999. Beta-catenin mutations are frequent in human hepatocellular carcinomas associated with hepatitis C virus infection. *Am J Pathol* 155:1795-1801.
13. Laurent-Puig, P., Legoix, P., Bluteau, O., Belghiti, J., Franco, D., Binot, F., Monges, G., Thomas, G., Bioulac-Sage, P., and Zucman-Rossi, J. 2001. Genetic alterations associated with hepatocellular carcinomas define distinct pathways of hepatocarcinogenesis. *Gastroenterology* 120: 1763-1773.
14. Satoh, S., Daigo, Y., Furukawa, Y., Kato, T., Miwa, N., Nishiwaki, T., Kawasoe, T., Ishiguro, H., Fujita, M., Tokino, T., et al. 2000. AXIN1 mutations in hepatocellular carcinomas, and growth suppression in cancer cells by virus-mediated transfer of AXIN1. *Nat Genet*. 24:245-250.
15. Merle, P., de la Monte, S., Kim, M., Herrmann, M., Tanaka, S., Von Dem Bussche, A., Kew, M. C., Trepo, C., and Wands, J. R. 2004. Functional consequences of frizzled-7 receptor overexpression in human hepatocellular carcinoma. *Gastroenterology* 127:1110-1122.
16. Merle, P., Kim, M., Herrmann, M., Gupte, A., Lefrancois, L., Califano, S., Trepo, C., Tanaka, S., Vitvitski, L., Monte, S. D., et al. 2005. Oncogenic role of the frizzled-7/beta-catenin pathway in hepatocellular carcinoma. *J Hepatol*.
17. Lin, X., and Perrimon, N. 1999. Dally cooperates with *Drosophila* Frizzled 2 to transduce Wingless signalling. *Nature* 400:281-284.
18. Willert, K., Brown, J. D., Danenberg, E., Duncan, A. W., Weissman, I. L., Reya, T., Yates, J. R., 3rd, and Nusse, R. 2003. Wnt proteins are lipid-modified and can act as stem cell growth factors. *Nature* 423:448-452.
19. Bradley, R. S., and Brown, A. M. 1990. The proto-oncogene int-1 encodes a secreted protein associated with the extracellular matrix. *Embo J* 9:1569-1575.
20. Reichsman, F., Smith, L., and Cumberledge, S. 1996. Glycosaminoglycans can modulate extracellular localization of the wingless protein and promote signal transduction. *J Cell Biol* 135:819-827.
21. Dhoot, G. K., Gustafsson, M. K., Ai, X., Sun, W., Standiford, D. M., and Emerson, C. P., Jr. 2001. Regulation of Wnt signaling and embryo patterning by an extracellular sulfatase. *Science* 293:1663-1666.
22. Roelink, H., Wang, J., Black, D. M., Solomon, E., and Nusse, R. 1993. Molecular cloning and chromosomal localization to 17q21 of the human WNT3 gene. *Genomics* 17:790-792.
23. Shimizu, H., Julius, M. A., Giarre, M., Zheng, Z., Brown, A. M., and Kitajewski, J. 1997. Transformation by Wnt family proteins correlates with regulation of beta-catenin. *Cell Growth Differ* 8:1349-1358.
24. Katoh, M. 2001. Molecular cloning and characterization of human WNT3. *Int J Oncol* 19:977-982.

25. Gregorieff, A., Pinto, D., Begthel, H., Destree, O., Kielman, M., and Clevers, H. 2005. Expression pattern of Wnt signaling components in the adult intestine. *Gastroenterology* 129:626-638.
26. Kirikoshi, H., Sekihara, H., and Katoh, M. 2001. Molecular cloning and characterization of human WNT11. *Int J Mol Med* 8:651-656.
27. Zhu, H., Mazor, M., Kawano, Y., Walker, M. M., Leung, H. Y., Armstrong, K., Waxman, J., and Kypta, R. M. 2004. Analysis of Wnt gene expression in prostate cancer: mutual inhibition by WNT11 and the androgen receptor. *Cancer Res* 64:7918-7926.
28. Smolich, B. D., McMahon, J. A., McMahon, A. P., and Papkoff, J. 1993. Wnt family proteins are secreted and associated with the cell surface. *Mol Biol Cell* 4:1267-1275.
29. Cha, M. Y., Kim, C. M., Park, Y. M., and Ryu, W. S. 2004. Hepatitis B virus X protein is essential for the activation of Wnt/beta-catenin signaling in hepatoma cells. *Hepatology* 39:1683-1693.
30. Veeman, M. T., Slusarski, D. C., Kaykas, A., Louie, S. H., and Moon, R. T. 2003. Zebrafish prickle, a modulator of noncanonical Wnt/Fz signaling, regulates gastrulation movements. *Curr Biol* 13:680-685.
31. Carruba, G., Cervello, M., Miceli, M. D., Farruggio, R., Notarbartolo, M., Virruso, L., Giannitrapani, L., Gambino, R., Montalto, G., and Castagnetta, L. 1999. Truncated form of beta-catenin and reduced expression of wild-type catenins feature HepG2 human liver cancer cells. *Ann N Y Acad Sci* 886:212-216.
32. Korinek, V., Barker, N., Morin, P. J., van Wichen, D., de Weger, R., Kinzler, K. W., Vogelstein, B., and Clevers, H.1997. Constitutive transcriptional activation by a beta-catenin-Tcf complex in APC−/− colon carcinoma. *Science* 275:1784-1787.

TABLE 1

Primer Pairs Used for the Detection of Wnt Ligand mRNA

| Wnt | Sequence | SEQ ID NO |
|---|---|---|
| GAPDH | Sense:<br>5'-GAAATCCCATCACCATCTTCCAG-3' | 28 |
|  | Anti-sense:<br>5'-ATGAGTCCTTCCACGATACCAAAG-3' | 29 |
| Wnt1 | Sense:<br>5'-TGTTGCCTGGCTGGGTTTC-3' | 30 |
|  | Anti-sense:<br>5'-CTGTAAGCAGGTTCGTGGAG-3' | 31 |
| Wnt2 | Sense:<br>5'-GTGGATGCAAAGGAAAGGAA-3' | 32 |
|  | Anti-sense:<br>5'-AGCCAGCATGTCCTGAGAGT-3' | 33 |
| Wnt2b | Sense:<br>5'-ACCCAAGATGGTGCCAACTTC-3' | 34 |
|  | Anti-sense:<br>5'-CACAACCGTCTGTTCCTTTTGATG-3' | 35 |
| Wnt3 | Sense:<br>5'-GGAGTGTATTCGCATCTACGACG-3' | 36 |
|  | Anti-sense:<br>5'-CGAGTTGGGTCTGGGTCATTTAC-3' | 37 |
| Wnt3a | Sense:<br>5'-CCCCACTCGGATACTTCTTACTCC-3' | 38 |
|  | Anti-sense:<br>5'-CTCCTGGATGCCAATCTTGATG-3' | 39 |

TABLE 1-continued

Primer Pairs Used for the Detection of Wnt Ligand mRNA

| Wnt | Sequence | SEQ ID NO |
|---|---|---|
| Wnt4 | Sense:<br>5'-TTTGTGGATGTGCGGGAGAG-3' | 40 |
|  | Anti-sense:<br>5'-ATCTGTGTGCGGCTTGAACTG-3' | 41 |
| Wnt5a | Sense:<br>5'-ACACCTCTTTCCAAACAGGCC-3' | 42 |
|  | Anti-sense:<br>5'-GGATTGTTAAACTCAACTCTC-3' | 43 |
| Wnt5b | Sense:<br>5'-GGAGCGAGAGAAGAACTTTGCC-3' | 44 |
|  | Anti-sense:<br>5'-GAAGCAGCACCAGTGGAACTTG-3' | 45 |
| Wnt6 | Sense:<br>5'-CTTGGTTATGGACCCTACCCAGGCATC-3' | 46 |
|  | Anti-sense:<br>5'-CACTGCAGCAGCTCGCCCATAGAA-3' | 47 |
| Wnt7a | Sense:<br>5'-GCTGCCTGGGCCACCTCTTTCTCA-3' | 48 |
|  | Anti-sense:<br>5'-CCCGGTGGTACAGGCCTTGCTTCT-3' | 49 |
| Wnt7b | Sense:<br>5'-TCAACGAGTGCCAGTACCAG-3' | 50 |
|  | Anti-sense:<br>5'-CCCTCGGCTTGGTTGTAGTA-3' | 51 |
| Wnt8a | Sense:<br>5'-TCCAGTTTGCTTGGGAACGC-3' | 52 |
|  | Anti-sense:<br>5'-CCATCACAGCCACAGTTTTCG-3' | 53 |
| Wnt8b | Sense:<br>5'-CATCTGTCTTTTCACCTGTGTCCTC-3' | 54 |
|  | Anti-sense:<br>5'-AATGCTGTCTCCCGATTGGC-3' | 55 |
| Wnt10a | Sense:<br>5'-TCTGGGTGCTCCTGTTCTTCCTAC-3' | 56 |
|  | Anti-sense:<br>5'-ATTGGTGTTGGCATTCGTGG-3' | 57 |
| Wnt10b | Sense:<br>5'-ACTGTCCCGAGGCAAGAGTTTC-3' | 58 |
|  | Anti-sense:<br>5'-GCATTTCCGCTTCAGGTTTTC-3' | 59 |
| Wnt11 | Sense:<br>3'-TGCTGACCTCAAGACCCGATAC-3' | 60 |
|  | Anti-sense:<br>3'-TGTCGCTTCCGTTGGATGTC-3' | 61 |

TABLE 1-continued

Primer Pairs Used for the Detection of Wnt Ligand mRNA

| Wnt | Sequence | SEQ ID NO |
|---|---|---|
| Wnt14 | Sense:<br>5'-TGCCAGTTCCAGTTCCGCTTTG-3'<br>Anti-sense:<br>5'-TTCACACCCACGAGGTTGTTG-3' | 62<br><br>63 |
| Wnt15 | Sense:<br>5'-TGAGTGCCAGTTTCAGTTCCG-3'<br>Anti-sense:<br>5'-CTTGTTTCCTCTCTTGGACCCC-3' | 64<br><br>65 |
| Wnt16 | Sense:<br>5'-CTGCTCCGATGATGTCCAGTATG-3'<br>Anti-sense:<br>5'-CATTCTCTGCCTTGTGTCCCTG-3' | 66<br><br>67 |

A number of embodiments of the invention have been described. Nevertheless, it will be understood that various modifications may be made without departing from the spirit and scope of the invention. Accordingly, other embodiments are within the scope of the following claims.

What is claimed is:

1. An isolated monoclonal antibody that binds specifically to the amino acid sequence LRAKYSLFKPPTERDL (SEQ ID NO:80).

2. A pharmaceutical composition comprising the antibody of claim 1 and a pharmaceutically acceptable carrier.

3. An isolated chimeric antibody that binds specifically to the amino acid sequence LRAKYSLFKPPTERDL (SEQ ID NO:80).

4. A pharmaceutical composition comprising the antibody of claim 3 and a pharmaceutically acceptable carrier.

5. An isolated humanized antibody that binds specifically to the amino acid sequence LRAKYSLFKPPTERDL (SEQ ID NO:80).

6. A pharmaceutical composition comprising the antibody of claim 5 and a pharmaceutically acceptable carrier.

7. An isolated single chain antibody that binds specifically to the amino acid sequence LRAKYSLFKPPTERDL (SEQ ID NO:80).

8. A pharmaceutical composition comprising the antibody of claim 7 and a pharmaceutically acceptable carrier.

9. An isolated Fab fragment that binds specifically to the amino acid sequence LRAKYSLFKPPTERDL (SEQ ID NO:80).

10. A pharmaceutical composition comprising the fragment of claim 9 and a pharmaceutically acceptable carrier.

11. An isolated F(ab')$_2$ fragment that binds specifically to the amino acid sequence LRAKYSLFKPPTERDL (SEQ ID NO:80).

12. A pharmaceutical composition comprising the fragment of claim 11 and a pharmaceutically acceptable carrier.

* * * * *

UNITED STATES PATENT AND TRADEMARK OFFICE
CERTIFICATE OF CORRECTION

PATENT NO. : 8,158,761 B2
APPLICATION NO. : 11/909308
DATED : April 17, 2012
INVENTOR(S) : Jack R. Wands and Miran Kim It is certified that error appears in the above-identified patent and that said Letters Patent is hereby corrected as shown below:

On the Title page, item (73) Assignee:

delete "Rhode Island Hospital" and replace with

-- Rhode Island Hospital, A Lifespan-Partner --.

Signed and Sealed this
Twelfth Day of June, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,158,761 B2 | Page 1 of 1 |
| APPLICATION NO. | : 11/909308 | |
| DATED | : April 17, 2012 | |
| INVENTOR(S) | : Jack R. Wands | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 572 days.

Signed and Sealed this
Fourth Day of September, 2012

David J. Kappos
*Director of the United States Patent and Trademark Office*